US008226681B2

(12) United States Patent
Clark et al.

(10) Patent No.: US 8,226,681 B2
(45) Date of Patent: Jul. 24, 2012

(54) METHODS, DEVICES, AND APPARATUS FOR MANAGING ACCESS THROUGH TISSUE

(75) Inventors: Ian J. Clark, West Bloomfield, MI (US); Wouter Roorda, Palo Alto, CA (US)

(73) Assignee: Abbott Laboratories, Abbott Park, IL (US)

( * ) Notice: Subject to any disclaimer, the term of this patent is extended or adjusted under 35 U.S.C. 154(b) by 350 days.

(21) Appl. No.: 11/767,818

(22) Filed: Jun. 25, 2007

(65) Prior Publication Data

US 2008/0319475 A1    Dec. 25, 2008

(51) Int. Cl.
*A61B 17/08*    (2006.01)
(52) U.S. Cl. .................................................... 606/213
(58) Field of Classification Search .................. 606/213
See application file for complete search history.

(56) References Cited

U.S. PATENT DOCUMENTS

| 287,046 | A | 10/1883 | Norton |
| 438,400 | A | 10/1890 | Brennen |
| 1,088,393 | A | 2/1914 | Backus |
| 1,331,401 | A | 2/1920 | Summers |
| 1,596,004 | A | 8/1926 | De Bengoa |
| 1,647,958 | A | 11/1927 | Ciarlante |
| 1,880,569 | A | 10/1932 | Weis |
| 2,087,074 | A | 7/1937 | Tucker |
| 2,254,620 | A | 9/1941 | Miller |
| 2,316,297 | A | 4/1943 | Southerland et al. |
| 2,371,978 | A | 3/1945 | Perham |
| 2,453,227 | A | 11/1948 | James |
| 2,583,625 | A | 1/1952 | Bergan |
| 2,684,070 | A | 7/1954 | Kelsey |
| 2,910,067 | A | 10/1959 | White |
| 2,944,311 | A | 7/1960 | Schneckenberger |
| 2,951,482 | A | 9/1960 | Sullivan |
| 2,969,887 | A | 1/1961 | Darmstadt et al. |
| 3,015,403 | A | 1/1962 | Fuller |
| 3,113,379 | A | 12/1963 | Frank |

(Continued)

FOREIGN PATENT DOCUMENTS

AU    2003297432    7/2004

(Continued)

OTHER PUBLICATIONS

U.S. Appl. No. 10/147,774, Jun. 8, 2010, Office Action.

(Continued)

*Primary Examiner* — Melanie Tyson
*Assistant Examiner* — Son Dang
(74) *Attorney, Agent, or Firm* — Workman Nydegger; Randy Shen

(57) ABSTRACT

Devices and methods for managing access through tissue is disclosed. The device includes a body. The body is movable from a pre-deployed configuration towards a deployed configuration. The device includes a plurality of tissue engaging portions that extend from the body. At least a portion of the tissue engaging portions are obtuse. At least two of the tissue engaging portions are separated by a first distance in the deployed configuration and a second distance in the pre-deployed configuration. The first distance is smaller than the second distance. The method includes deploying a closure element to tissue adjacent a tissue opening to substantially close the opening following a first procedure. The method also includes selectively opening the opening in the tissue by advancing a distal end of a medical device through the deployed closure element as a part of or before a second procedure.

14 Claims, 22 Drawing Sheets

U.S. PATENT DOCUMENTS

| | | |
|---|---|---|
| 3,120,230 A | 2/1964 | Skold |
| 3,142,878 A | 8/1964 | Santora |
| 3,209,754 A | 10/1965 | Brown |
| 3,482,428 A | 12/1969 | Kapitanov et al. |
| 3,494,533 A | 2/1970 | Green et al. |
| 3,510,923 A | 5/1970 | Blake |
| 3,523,351 A | 8/1970 | Filia |
| 3,586,002 A | 6/1971 | Wood |
| 3,604,425 A | 9/1971 | Le Roy |
| 3,618,447 A | 11/1971 | Goins |
| 3,677,243 A | 7/1972 | Nerz |
| 3,757,629 A | 9/1973 | Schneider |
| 3,805,337 A | 4/1974 | Branstetter |
| 3,823,719 A | 7/1974 | Cummings |
| 3,828,791 A | 8/1974 | Santos |
| 3,856,016 A | 12/1974 | Davis |
| 3,874,388 A | 4/1975 | King et al. |
| 3,908,662 A | 9/1975 | Razgulov et al. |
| 3,926,194 A | 12/1975 | Greenberg et al. |
| 3,939,820 A | 2/1976 | Grayzel |
| 3,944,114 A | 3/1976 | Coppens |
| 3,960,147 A | 6/1976 | Murray |
| 3,985,138 A | 10/1976 | Jarvik |
| 4,014,492 A | 3/1977 | Rothfuss |
| 4,018,228 A | 4/1977 | Goosen |
| 4,064,881 A | 12/1977 | Meredith |
| 4,112,944 A | 9/1978 | Williams |
| 4,153,321 A | 5/1979 | Pombrol |
| 4,162,673 A | 7/1979 | Patel |
| 4,169,476 A | 10/1979 | Hiltebrandt |
| 4,192,315 A | 3/1980 | Hilzinger et al. |
| 4,201,215 A | 5/1980 | Crossett et al. |
| 4,204,541 A | 5/1980 | Kapitanov |
| 4,207,870 A | 6/1980 | Eldridge |
| 4,214,587 A | 7/1980 | Sakura, Jr. |
| 4,215,699 A | 8/1980 | Patel |
| 4,217,902 A | 8/1980 | March |
| 4,273,129 A | 6/1981 | Boebel |
| 4,274,415 A | 6/1981 | Kanamoto et al. |
| 4,278,091 A | 7/1981 | Borzone |
| 4,317,445 A | 3/1982 | Robinson |
| 4,318,401 A | 3/1982 | Zimmerman |
| 4,327,485 A | 5/1982 | Rix |
| 4,345,606 A | 8/1982 | Littleford |
| 4,368,736 A | 1/1983 | Kaster |
| 4,396,139 A | 8/1983 | Hall et al. |
| 4,411,654 A | 10/1983 | Boarini et al. |
| 4,412,832 A | 11/1983 | Kling et al. |
| 4,428,376 A | 1/1984 | Mericle |
| 4,440,170 A | 4/1984 | Golden et al. |
| 4,449,531 A | 5/1984 | Cerwin et al. |
| 4,475,544 A | 10/1984 | Reis |
| 4,480,356 A | 11/1984 | Martin |
| 4,485,816 A | 12/1984 | Krumme |
| RE31,855 E | 3/1985 | Osborne |
| 4,505,273 A | 3/1985 | Braun et al. |
| 4,505,274 A | 3/1985 | Speelman |
| 4,523,591 A | 6/1985 | Kaplan et al. |
| 4,523,695 A | 6/1985 | Braun et al. |
| 4,525,157 A | 6/1985 | Vaillancourt |
| 4,526,174 A | 7/1985 | Froehlich |
| 4,586,503 A | 5/1986 | Kirsch et al. |
| 4,592,498 A | 6/1986 | Braun et al. |
| 4,596,559 A | 6/1986 | Fleischhacker |
| 4,607,638 A | 8/1986 | Crainich |
| 4,610,251 A | 9/1986 | Kumar |
| 4,610,252 A | 9/1986 | Catalano |
| 4,635,634 A | 1/1987 | Santos |
| 4,651,737 A | 3/1987 | Deniega |
| 4,664,305 A | 5/1987 | Blake, III et al. |
| 4,665,906 A | 5/1987 | Jervis |
| 4,687,469 A | 8/1987 | Osypka |
| 4,693,249 A | 9/1987 | Schenck et al. |
| 4,719,917 A | 1/1988 | Barrows et al. |
| 4,724,840 A | 2/1988 | McVay et al. |
| 4,738,658 A | 4/1988 | Magro et al. |
| 4,744,364 A | 5/1988 | Kensey |
| 4,747,407 A | 5/1988 | Liu et al. |
| 4,759,364 A | 7/1988 | Boebel |
| 4,771,782 A | 9/1988 | Millar |
| 4,772,266 A | 9/1988 | Groshong |
| 4,777,950 A | 10/1988 | Kees, Jr. |
| 4,789,090 A | 12/1988 | Blake, III |
| 4,832,688 A | 5/1989 | Sagae et al. |
| 4,836,204 A | 6/1989 | Landymore et al. |
| 4,852,568 A | 8/1989 | Kensey |
| 4,860,746 A | 8/1989 | Yoon |
| 4,865,026 A | 9/1989 | Barrett |
| 4,874,122 A | 10/1989 | Froelich et al. |
| 4,878,915 A | 11/1989 | Brantigan |
| 4,887,601 A | 12/1989 | Richards |
| 4,890,612 A | 1/1990 | Kensey |
| 4,902,508 A | 2/1990 | Badylak et al. |
| 4,917,087 A | 4/1990 | Walsh et al. |
| 4,917,089 A | 4/1990 | Sideris |
| 4,929,240 A | 5/1990 | Kirsch et al. |
| 4,934,364 A | 6/1990 | Green |
| 4,950,258 A | 8/1990 | Kawai et al. |
| 4,957,499 A | 9/1990 | Lipatov et al. |
| 4,961,729 A | 10/1990 | Vaillancourt |
| 4,976,721 A | 12/1990 | Blasnik et al. |
| 4,983,176 A | 1/1991 | Cushman et al. |
| 4,997,436 A | 3/1991 | Oberlander |
| 4,997,439 A | 3/1991 | Chen |
| 5,002,562 A | 3/1991 | Oberlander |
| 5,007,921 A | 4/1991 | Brown |
| 5,015,247 A | 5/1991 | Michelson |
| 5,021,059 A | 6/1991 | Kensey et al. |
| 5,026,390 A | 6/1991 | Brown |
| 5,030,226 A | 7/1991 | Green et al. |
| 5,032,127 A | 7/1991 | Frazee et al. |
| 5,047,047 A | 9/1991 | Yoon |
| 5,053,008 A | 10/1991 | Bajaj |
| 5,059,201 A | 10/1991 | Asnis |
| 5,061,274 A | 10/1991 | Kensey |
| 5,078,731 A | 1/1992 | Hayhurst |
| 5,092,941 A | 3/1992 | Miura |
| 5,100,418 A | 3/1992 | Yoon et al. |
| 5,100,422 A | 3/1992 | Berguer et al. |
| 5,108,420 A | 4/1992 | Marks |
| 5,108,421 A | 4/1992 | Fowler |
| 5,114,032 A | 5/1992 | Laidlaw |
| 5,114,065 A | 5/1992 | Storace |
| 5,116,349 A | 5/1992 | Aranyi |
| 5,122,122 A | 6/1992 | Allgood |
| 5,122,156 A | 6/1992 | Granger et al. |
| 5,131,379 A | 7/1992 | Sewell, Jr. |
| 5,147,381 A | 9/1992 | Heimerl et al. |
| 5,156,609 A | 10/1992 | Nakao et al. |
| 5,167,634 A | 12/1992 | Corrigan, Jr. et al. |
| 5,167,643 A | 12/1992 | Lynn |
| 5,171,249 A | 12/1992 | Stefanchik et al. |
| 5,171,250 A | 12/1992 | Yoon |
| 5,176,648 A | 1/1993 | Holmes et al. |
| 5,192,288 A | 3/1993 | Thompson et al. |
| 5,192,300 A | 3/1993 | Fowler |
| 5,192,301 A | 3/1993 | Kamiya et al. |
| 5,192,302 A | 3/1993 | Kensey et al. |
| 5,192,602 A | 3/1993 | Spencer et al. |
| 5,209,756 A | 5/1993 | Seedhom et al. |
| 5,217,024 A | 6/1993 | Dorsey et al. |
| 5,222,974 A | 6/1993 | Kensey et al. |
| 5,226,908 A | 7/1993 | Yoon |
| 5,236,435 A | 8/1993 | Sewell, Jr. |
| 5,242,456 A | 9/1993 | Nash et al. |
| 5,242,457 A | 9/1993 | Akopov et al. |
| 5,242,459 A | 9/1993 | Buelna |
| 5,243,857 A | 9/1993 | Velez |
| 5,246,156 A | 9/1993 | Rothfuss et al. |
| 5,246,443 A | 9/1993 | Mai |
| 5,250,058 A | 10/1993 | Miller et al. |
| 5,254,105 A | 10/1993 | Haaga |
| 5,269,792 A | 12/1993 | Kovac et al. |
| 5,275,616 A | 1/1994 | Fowler |
| 5,281,422 A | 1/1994 | Badylak et al. |
| 5,282,808 A | 2/1994 | Kovac et al. |
| 5,282,827 A | 2/1994 | Kensey et al. |

| Patent No. | Date | Inventor |
|---|---|---|
| 5,289,963 A | 3/1994 | McGarry et al. |
| 5,290,243 A | 3/1994 | Chodorow et al. |
| 5,290,310 A | 3/1994 | Makower et al. |
| 5,292,309 A | 3/1994 | Van Tassel et al. |
| 5,292,332 A | 3/1994 | Lee |
| 5,304,183 A | 4/1994 | Gourlay et al. |
| 5,304,184 A | 4/1994 | Hathaway et al. |
| 5,304,204 A | 4/1994 | Bregen |
| 5,306,254 A | 4/1994 | Nash et al. |
| 5,309,927 A | 5/1994 | Welch |
| 5,318,542 A | 6/1994 | Hirsch et al. |
| 5,320,639 A | 6/1994 | Rudnick |
| 5,327,908 A | 7/1994 | Gerry |
| 5,330,445 A | 7/1994 | Haaga |
| 5,334,216 A | 8/1994 | Vidal et al. |
| 5,334,217 A | 8/1994 | Das |
| 5,335,680 A | 8/1994 | Moore |
| 5,340,360 A | 8/1994 | Stefanchik |
| 5,350,399 A | 9/1994 | Erlebacher et al. |
| 5,352,229 A | 10/1994 | Goble et al. |
| 5,364,406 A | 11/1994 | Sewell, Jr. |
| 5,364,408 A | 11/1994 | Gordon |
| 5,366,458 A | 11/1994 | Korthoff et al. |
| 5,366,479 A | 11/1994 | McGarry et al. |
| 5,383,896 A | 1/1995 | Gershony et al. |
| RE34,866 E | 2/1995 | Kensey et al. |
| 5,392,978 A | 2/1995 | Velez et al. |
| 5,395,030 A | 3/1995 | Kuramoto et al. |
| 5,411,520 A | 5/1995 | Nash et al. |
| 5,413,571 A | 5/1995 | Katsaros et al. |
| 5,413,584 A | 5/1995 | Schulze |
| 5,416,584 A | 5/1995 | Kay |
| 5,417,699 A | 5/1995 | Klein et al. |
| 5,419,777 A | 5/1995 | Hofling |
| 5,423,857 A | 6/1995 | Rosenman et al. |
| 5,425,489 A | 6/1995 | Shichman et al. |
| 5,425,740 A | 6/1995 | Hutchinson, Jr. |
| 5,431,639 A * | 7/1995 | Shaw ............................ 604/264 |
| 5,431,667 A | 7/1995 | Thompson et al. |
| 5,433,721 A | 7/1995 | Hooven et al. |
| 5,437,631 A | 8/1995 | Janzen |
| 5,439,479 A | 8/1995 | Shichman et al. |
| 5,443,477 A | 8/1995 | Marin et al. |
| 5,443,481 A | 8/1995 | Lee |
| 5,445,167 A | 8/1995 | Yoon et al. |
| 5,449,359 A | 9/1995 | Groiso |
| 5,456,400 A | 10/1995 | Shichman et al. |
| 5,462,561 A | 10/1995 | Voda |
| 5,464,413 A | 11/1995 | Siska, Jr. et al. |
| 5,466,241 A | 11/1995 | Leroy et al. |
| 5,470,010 A | 11/1995 | Rothfuss et al. |
| 5,474,557 A | 12/1995 | Mai |
| 5,474,569 A | 12/1995 | Zinreich et al. |
| 5,476,505 A | 12/1995 | Limon |
| 5,478,352 A | 12/1995 | Fowler |
| 5,478,353 A | 12/1995 | Yoon |
| 5,478,354 A | 12/1995 | Tovey et al. |
| 5,486,195 A | 1/1996 | Myers et al. |
| 5,497,933 A | 3/1996 | DeFonzo et al. |
| 5,507,744 A | 4/1996 | Tay et al. |
| 5,507,755 A | 4/1996 | Gresl et al. |
| 5,522,840 A | 6/1996 | Krajicek |
| 5,527,322 A | 6/1996 | Klein et al. |
| 5,536,251 A | 7/1996 | Evard et al. |
| 5,540,712 A | 7/1996 | Kleshinski et al. |
| 5,540,716 A | 7/1996 | Hlavacek |
| 5,544,802 A | 8/1996 | Crainich |
| 5,547,474 A | 8/1996 | Kloeckl et al. |
| 5,560,532 A | 10/1996 | DeFonzo et al. |
| 5,571,120 A | 11/1996 | Yoon |
| 5,573,784 A | 11/1996 | Badylak et al. |
| 5,575,771 A | 11/1996 | Walinsky |
| 5,584,879 A | 12/1996 | Reimold et al. |
| 5,591,205 A | 1/1997 | Fowler |
| 5,593,412 A | 1/1997 | Martinez et al. |
| 5,601,602 A | 2/1997 | Fowler |
| 5,609,597 A | 3/1997 | Lehrer |
| 5,613,974 A | 3/1997 | Andreas et al. |
| 5,618,291 A | 4/1997 | Thompson et al. |
| 5,620,452 A | 4/1997 | Yoon |
| 5,620,461 A | 4/1997 | Muijs et al. |
| 5,643,318 A | 7/1997 | Tsukernik et al. |
| 5,645,565 A | 7/1997 | Rudd et al. |
| 5,645,566 A | 7/1997 | Brenneman et al. |
| 5,645,567 A | 7/1997 | Crainich |
| 5,649,959 A | 7/1997 | Hannam et al. |
| D383,539 S | 9/1997 | Croley |
| 5,674,231 A | 10/1997 | Green et al. |
| 5,676,689 A | 10/1997 | Kensey et al. |
| 5,676,974 A | 10/1997 | Valdes et al. |
| 5,681,334 A | 10/1997 | Evans et al. |
| 5,683,405 A | 11/1997 | Yacoubian et al. |
| 5,690,674 A | 11/1997 | Diaz |
| 5,695,504 A | 12/1997 | Gifford, III et al. |
| 5,695,505 A | 12/1997 | Yoon |
| 5,695,524 A | 12/1997 | Kelley et al. |
| 5,700,273 A | 12/1997 | Buelna et al. |
| 5,713,899 A | 2/1998 | Marnay et al. |
| 5,716,375 A | 2/1998 | Fowler |
| 5,720,755 A | 2/1998 | Dakov |
| 5,725,498 A | 3/1998 | Janzen et al. |
| 5,725,552 A | 3/1998 | Kotula et al. |
| 5,725,554 A | 3/1998 | Simon et al. |
| 5,728,110 A | 3/1998 | Vidal et al. |
| 5,728,114 A | 3/1998 | Evans et al. |
| 5,728,122 A | 3/1998 | Leschinsky et al. |
| 5,728,132 A | 3/1998 | Van Tassel et al. |
| 5,732,872 A | 3/1998 | Bolduc et al. |
| 5,735,873 A | 4/1998 | MacLean |
| 5,752,966 A | 5/1998 | Chang |
| 5,755,726 A | 5/1998 | Pratt et al. |
| 5,755,778 A | 5/1998 | Kleshinski |
| 5,766,217 A | 6/1998 | Christy |
| 5,766,246 A | 6/1998 | Mulhauser et al. |
| 5,769,870 A | 6/1998 | Salahieh et al. |
| 5,776,147 A | 7/1998 | Dolendo |
| 5,779,707 A | 7/1998 | Bertholet et al. |
| 5,782,844 A | 7/1998 | Yoon et al. |
| 5,782,860 A | 7/1998 | Epstein et al. |
| 5,782,861 A | 7/1998 | Cragg et al. |
| 5,795,958 A | 8/1998 | Rao et al. |
| 5,797,928 A | 8/1998 | Kogasaka |
| 5,797,931 A | 8/1998 | Bito et al. |
| 5,797,933 A | 8/1998 | Snow et al. |
| 5,797,958 A | 8/1998 | Yoon |
| 5,810,776 A | 9/1998 | Bacich et al. |
| 5,810,846 A | 9/1998 | Virnich et al. |
| 5,810,851 A | 9/1998 | Yoon |
| 5,817,113 A | 10/1998 | Gifford, III et al. |
| 5,820,631 A | 10/1998 | Nobles |
| 5,827,298 A | 10/1998 | Hart et al. |
| 5,830,125 A | 11/1998 | Scribner et al. |
| 5,833,698 A | 11/1998 | Hinchliffe et al. |
| 5,843,167 A | 12/1998 | Dwyer et al. |
| 5,853,421 A | 12/1998 | Leschinsky et al. |
| 5,853,422 A | 12/1998 | Huebsch et al. |
| 5,855,312 A | 1/1999 | Toledano |
| 5,858,082 A | 1/1999 | Cruz et al. |
| 5,860,991 A | 1/1999 | Klein et al. |
| 5,861,005 A | 1/1999 | Kontos |
| 5,868,755 A | 2/1999 | Kanner et al. |
| 5,868,763 A | 2/1999 | Spence et al. |
| 5,871,474 A | 2/1999 | Hermann et al. |
| 5,871,501 A | 2/1999 | Leschinsky et al. |
| 5,871,525 A | 2/1999 | Edwards et al. |
| 5,873,876 A | 2/1999 | Christy |
| 5,879,366 A | 3/1999 | Shaw et al. |
| 5,891,088 A | 4/1999 | Thompson et al. |
| 5,897,487 A | 4/1999 | Ouchi |
| 5,902,310 A | 5/1999 | Foerster et al. |
| 5,904,697 A | 5/1999 | Gifford, III et al. |
| 5,906,631 A | 5/1999 | Imran |
| 5,907,893 A | 6/1999 | Zadno-Azizi et al. |
| 5,910,155 A | 6/1999 | Ratcliff et al. |
| 5,919,207 A | 7/1999 | Taheri |
| 5,922,009 A | 7/1999 | Epstein et al. |
| 5,928,231 A | 7/1999 | Klein et al. |
| 5,928,251 A | 7/1999 | Aranyi et al. |

| | | | | | | |
|---|---|---|---|---|---|---|
| 5,935,147 | A | 8/1999 | Kensey et al. | 6,267,773 B1 | 7/2001 | Gadberry et al. |
| 5,938,667 | A | 8/1999 | Peyser et al. | 6,273,903 B1 | 8/2001 | Wilk |
| 5,941,890 | A | 8/1999 | Voegele et al. | 6,277,140 B2 | 8/2001 | Ginn et al. |
| 5,947,999 | A | 9/1999 | Groiso | 6,280,460 B1 | 8/2001 | Bolduc et al. |
| 5,951,518 | A | 9/1999 | Licata et al. | 6,287,322 B1 | 9/2001 | Zhu et al. |
| 5,951,576 | A | 9/1999 | Wakabayashi | 6,296,657 B1 | 10/2001 | Brucker |
| 5,951,589 | A | 9/1999 | Epstein et al. | 6,305,891 B1 | 10/2001 | Burlingame |
| 5,957,936 | A | 9/1999 | Yoon et al. | 6,319,258 B1 | 11/2001 | McAllen, III et al. |
| 5,957,938 | A | 9/1999 | Zhu et al. | 6,322,580 B1 | 11/2001 | Kanner |
| 5,957,940 | A | 9/1999 | Tanner et al. | 6,328,727 B1 | 12/2001 | Frazier et al. |
| 5,964,782 | A | 10/1999 | Lafontaine et al. | 6,329,386 B1 | 12/2001 | Mollison |
| 5,976,161 | A | 11/1999 | Kirsch et al. | 6,334,865 B1 | 1/2002 | Redmond et al. |
| 5,984,934 | A | 11/1999 | Ashby et al. | 6,348,064 B1 | 2/2002 | Kanner |
| 5,984,949 | A | 11/1999 | Levin | 6,358,258 B1 | 3/2002 | Arcia et al. |
| 5,993,468 | A | 11/1999 | Rygaard | 6,375,671 B1 | 4/2002 | Kobayashi et al. |
| 5,993,476 | A | 11/1999 | Groiso | D457,958 S | 5/2002 | Dycus |
| 6,001,110 | A | 12/1999 | Adams | 6,383,208 B1 | 5/2002 | Sancoff et al. |
| 6,004,341 | A | 12/1999 | Zhu et al. | 6,391,048 B1 | 5/2002 | Ginn et al. |
| 6,007,563 | A | 12/1999 | Nash et al. | 6,395,015 B1 | 5/2002 | Borst et al. |
| 6,010,517 | A | 1/2000 | Baccaro | 6,398,752 B1 | 6/2002 | Sweezer et al. |
| 6,013,084 | A | 1/2000 | Ken et al. | 6,402,765 B1 | 6/2002 | Monassevitch et al. |
| 6,015,815 | A | 1/2000 | Mollison | 6,409,739 B1 | 6/2002 | Nobles et al. |
| 6,019,779 | A | 2/2000 | Thorud et al. | 6,419,669 B1 | 7/2002 | Frazier et al. |
| 6,022,372 | A | 2/2000 | Kontos | 6,423,054 B1 | 7/2002 | Ouchi |
| 6,024,750 | A | 2/2000 | Mastri | 6,425,911 B1 | 7/2002 | Akerfeldt et al. |
| 6,030,364 | A | 2/2000 | Durgin et al. | 6,428,472 B1 | 8/2002 | Haas |
| 6,030,413 | A | 2/2000 | Lazarus | 6,428,548 B1 | 8/2002 | Durgin et al. |
| 6,033,427 | A | 3/2000 | Lee | 6,443,158 B1 | 9/2002 | Lafontaine et al. |
| 6,036,703 | A | 3/2000 | Evans et al. | 6,443,963 B1 | 9/2002 | Baldwin et al. |
| 6,036,720 | A | 3/2000 | Abrams et al. | 6,447,540 B1 | 9/2002 | Fontaine et al. |
| 6,045,570 | A | 4/2000 | Epstein et al. | 6,450,391 B1 | 9/2002 | Kayan et al. |
| 6,048,358 | A | 4/2000 | Barak | 6,458,130 B1 | 10/2002 | Frazier et al. |
| 6,056,768 | A | 5/2000 | Cates et al. | 6,461,364 B1 | 10/2002 | Ginn et al. |
| 6,056,769 | A | 5/2000 | Epstein et al. | 6,482,224 B1 | 11/2002 | Michler et al. |
| 6,056,770 | A | 5/2000 | Epstein et al. | 6,488,692 B1 | 12/2002 | Spence et al. |
| 6,059,800 | A | 5/2000 | Hart et al. | 6,500,115 B2 | 12/2002 | Krattiger et al. |
| 6,059,825 | A | 5/2000 | Hobbs et al. | 6,506,210 B1 | 1/2003 | Kanner |
| 6,063,085 | A | 5/2000 | Tay et al. | 6,508,828 B1 | 1/2003 | Akerfeldt et al. |
| 6,063,114 | A | 5/2000 | Nash et al. | 6,517,569 B2 | 2/2003 | Mikus et al. |
| 6,071,300 | A | 6/2000 | Brenneman et al. | 6,533,762 B2 | 3/2003 | Kanner et al. |
| 6,077,281 | A | 6/2000 | Das | 6,533,812 B2 | 3/2003 | Swanson et al. |
| 6,077,291 | A | 6/2000 | Das | 6,537,288 B2 | 3/2003 | Vargas et al. |
| 6,080,182 | A | 6/2000 | Shaw et al. | 6,547,806 B1 | 4/2003 | Ding |
| 6,080,183 | A | 6/2000 | Tsugita et al. | 6,551,319 B2 | 4/2003 | Lieberman |
| 6,083,242 | A | 7/2000 | Cook | 6,569,173 B1 | 5/2003 | Blatter et al. |
| 6,090,130 | A | 7/2000 | Nash et al. | 6,569,185 B2 | 5/2003 | Ungs |
| 6,102,271 | A | 8/2000 | Longo et al. | 6,572,629 B2 | 6/2003 | Kalloo et al. |
| 6,110,184 | A | 8/2000 | Weadock | 6,582,452 B2 | 6/2003 | Coleman et al. |
| 6,113,612 | A | 9/2000 | Swanson et al. | 6,582,482 B2 | 6/2003 | Gillman et al. |
| 6,117,125 | A | 9/2000 | Rothbarth et al. | 6,596,012 B2 | 7/2003 | Akerfeldt et al. |
| 6,117,148 | A | 9/2000 | Ravo | 6,599,303 B1 | 7/2003 | Peterson et al. |
| 6,117,157 | A | 9/2000 | Tekulve | 6,602,263 B1 | 8/2003 | Swanson et al. |
| 6,120,524 | A | 9/2000 | Taheri | 6,610,072 B1 | 8/2003 | Christy et al. |
| 6,126,675 | A | 10/2000 | Schervinsky et al. | 6,613,059 B2 | 9/2003 | Schaller et al. |
| 6,136,010 | A | 10/2000 | Modesitt et al. | 6,616,686 B2 | 9/2003 | Coleman et al. |
| 6,149,660 | A | 11/2000 | Laufer et al. | 6,623,509 B2 | 9/2003 | Ginn |
| 6,149,667 | A | 11/2000 | Hovland et al. | 6,623,510 B2 | 9/2003 | Carley et al. |
| 6,152,144 | A | 11/2000 | Lesh et al. | 6,626,918 B1 | 9/2003 | Ginn et al. |
| 6,152,936 | A | 11/2000 | Christy et al. | 6,626,920 B2 | 9/2003 | Whayne |
| 6,152,937 | A | 11/2000 | Peterson et al. | 6,632,238 B2 | 10/2003 | Ginn et al. |
| 6,165,204 | A | 12/2000 | Levinson et al. | 6,634,537 B2 | 10/2003 | Chen |
| 6,171,277 | B1 | 1/2001 | Ponzi | 6,645,205 B2 | 11/2003 | Ginn |
| 6,171,329 | B1 | 1/2001 | Shaw et al. | 6,652,538 B2 | 11/2003 | Kayan et al. |
| 6,179,849 | B1 | 1/2001 | Yencho et al. | 6,652,556 B1 | 11/2003 | VanTassel et al. |
| 6,193,708 | B1 | 2/2001 | Ken et al. | 6,663,655 B2 | 12/2003 | Ginn et al. |
| 6,193,734 | B1 | 2/2001 | Bolduc et al. | 6,669,714 B2 | 12/2003 | Coleman et al. |
| 6,197,042 | B1 | 3/2001 | Ginn et al. | 6,673,083 B1 | 1/2004 | Kayan et al. |
| 6,198,974 | B1 | 3/2001 | Webster, Jr. | 6,676,671 B2 | 1/2004 | Robertson et al. |
| 6,200,329 | B1 | 3/2001 | Fung et al. | 6,676,685 B2 | 1/2004 | Pedros et al. |
| 6,206,895 | B1 | 3/2001 | Levinson | 6,679,904 B2 | 1/2004 | Gleeson et al. |
| 6,206,913 | B1 | 3/2001 | Yencho et al. | 6,689,147 B1 | 2/2004 | Koster, Jr. |
| 6,206,931 | B1 | 3/2001 | Cook et al. | 6,695,867 B2 | 2/2004 | Ginn et al. |
| 6,210,407 | B1 | 4/2001 | Webster | 6,699,256 B1 | 3/2004 | Logan et al. |
| 6,220,248 | B1 | 4/2001 | Voegele et al. | 6,702,826 B2 | 3/2004 | Liddicoat et al. |
| 6,221,102 | B1 | 4/2001 | Baker et al. | 6,712,836 B1 | 3/2004 | Berg et al. |
| 6,245,079 | B1 | 6/2001 | Nobles et al. | 6,712,837 B2 | 3/2004 | Akerfeldt et al. |
| 6,248,124 | B1 | 6/2001 | Pedros et al. | 6,719,777 B2 | 4/2004 | Ginn et al. |
| 6,254,617 | B1 | 7/2001 | Spence et al. | 6,726,704 B1 | 4/2004 | Loshakove et al. |
| 6,254,642 | B1 | 7/2001 | Taylor | 6,743,195 B2 | 6/2004 | Zucker |

| | | | | | |
|---|---|---|---|---|---|
| 6,743,243 B1 * | 6/2004 | Roy et al. ............... 606/153 | 2003/0009180 A1 | 1/2003 | Hinchliffe et al. |
| 6,743,259 B2 | 6/2004 | Ginn | 2003/0032981 A1 | 2/2003 | Kanner et al. |
| 6,749,621 B2 | 6/2004 | Pantages et al. | 2003/0045893 A1 | 3/2003 | Ginn |
| 6,749,622 B2 | 6/2004 | McGuckin et al. | 2003/0055455 A1 | 3/2003 | Yang et al. |
| 6,755,842 B2 | 6/2004 | Kanner et al. | 2003/0065358 A1 | 4/2003 | Frecker et al. |
| 6,767,356 B2 | 7/2004 | Kanner et al. | 2003/0078598 A1 | 4/2003 | Ginn et al. |
| 6,776,785 B1 | 8/2004 | Yencho et al. | 2003/0083679 A1 | 5/2003 | Grudem et al. |
| 6,780,197 B2 | 8/2004 | Roe et al. | 2003/0093096 A1 | 5/2003 | McGuckin et al. |
| 6,786,915 B2 | 9/2004 | Akerfeldt et al. | 2003/0097140 A1 | 5/2003 | Kanner |
| 6,790,218 B2 | 9/2004 | Jayaraman | 2003/0109890 A1 | 6/2003 | Kanner et al. |
| 6,790,220 B2 | 9/2004 | Morris et al. | 2003/0125766 A1 | 7/2003 | Ding |
| 6,837,906 B2 | 1/2005 | Ginn | 2003/0144695 A1 | 7/2003 | McGuckin, Jr. et al. |
| 6,846,319 B2 | 1/2005 | Ginn et al. | 2003/0158577 A1 | 8/2003 | Pantages et al. |
| 6,860,895 B1 | 3/2005 | Akerfeldt et al. | 2003/0158578 A1 | 8/2003 | Pantages et al. |
| 6,890,343 B2 | 5/2005 | Ginn et al. | 2003/0195504 A1 | 10/2003 | Tallarida et al. |
| 6,896,687 B2 | 5/2005 | Dakov | 2003/0195561 A1 | 10/2003 | Carley et al. |
| 6,896,692 B2 | 5/2005 | Ginn et al. | 2003/0233095 A1 | 12/2003 | Urbanski et al. |
| 6,926,723 B1 | 8/2005 | Mulhauser et al. | 2004/0009205 A1 | 1/2004 | Sawhney |
| 6,926,731 B2 | 8/2005 | Coleman et al. | 2004/0009289 A1 | 1/2004 | Carley et al. |
| 6,929,634 B2 | 8/2005 | Dorros et al. | 2004/0059376 A1 | 3/2004 | Breuniger |
| 6,942,674 B2 | 9/2005 | Belef et al. | 2004/0068273 A1 | 4/2004 | Fariss et al. |
| 6,942,691 B1 | 9/2005 | Chuter | 2004/0073236 A1 | 4/2004 | Carley et al. |
| 6,964,668 B2 | 11/2005 | Modesitt et al. | 2004/0073255 A1 | 4/2004 | Ginn et al. |
| 6,969,397 B2 | 11/2005 | Ginn | 2004/0082906 A1 | 4/2004 | Tallarida et al. |
| 6,989,003 B2 | 1/2006 | Wing et al. | 2004/0087985 A1 | 5/2004 | Loshakove et al. |
| 6,989,016 B2 | 1/2006 | Tallarida et al. | 2004/0092964 A1 | 5/2004 | Modesitt et al. |
| 7,001,398 B2 | 2/2006 | Carley et al. | 2004/0092968 A1 | 5/2004 | Caro et al. |
| 7,001,400 B1 | 2/2006 | Modesitt et al. | 2004/0093024 A1 | 5/2004 | Lousararian et al. |
| 7,008,435 B2 | 3/2006 | Cummins | 2004/0093027 A1 | 5/2004 | Fabisiak et al. |
| 7,008,439 B1 | 3/2006 | Janzen et al. | 2004/0097978 A1 | 5/2004 | Modesitt et al. |
| 7,033,379 B2 | 4/2006 | Peterson | 2004/0127940 A1 | 7/2004 | Ginn et al. |
| 7,060,084 B1 | 6/2006 | Loshakove et al. | 2004/0143290 A1 | 7/2004 | Brightbill |
| 7,063,711 B1 | 6/2006 | Loshakove et al. | 2004/0153122 A1 | 8/2004 | Palermo |
| 7,083,635 B2 | 8/2006 | Ginn | 2004/0153123 A1 | 8/2004 | Palermo et al. |
| 7,108,709 B2 | 9/2006 | Cummins | 2004/0158127 A1 | 8/2004 | Okada |
| 7,111,768 B2 | 9/2006 | Cummins et al. | 2004/0158287 A1 | 8/2004 | Cragg et al. |
| 7,112,225 B2 | 9/2006 | Ginn | 2004/0158309 A1 | 8/2004 | Wachter et al. |
| 7,144,411 B2 | 12/2006 | Ginn et al. | 2004/0167511 A1 | 8/2004 | Buehlmann et al. |
| 7,163,551 B2 | 1/2007 | Anthony et al. | 2004/0167570 A1 | 8/2004 | Pantages |
| 7,169,158 B2 | 1/2007 | Sniffin et al. | 2004/0191277 A1 | 9/2004 | Sawhney et al. |
| 7,169,164 B2 | 1/2007 | Borillo et al. | 2004/0215232 A1 | 10/2004 | Belhe et al. |
| 7,211,101 B2 | 5/2007 | Carley et al. | 2004/0249412 A1 | 12/2004 | Snow et al. |
| 7,311,720 B2 | 12/2007 | Mueller et al. | 2004/0254591 A1 | 12/2004 | Kanner et al. |
| 7,316,704 B2 | 1/2008 | Bagaoisan et al. | 2004/0267193 A1 | 12/2004 | Bagaoisan et al. |
| 7,322,995 B2 | 1/2008 | Buckman et al. | 2004/0267308 A1 | 12/2004 | Bagaoisan et al. |
| 7,326,230 B2 | 2/2008 | Ravikumar | 2004/0267312 A1 | 12/2004 | Kanner et al. |
| 7,331,979 B2 | 2/2008 | Khosravi et al. | 2005/0038460 A1 | 2/2005 | Jayaraman |
| 7,335,220 B2 | 2/2008 | Khosravi et al. | 2005/0038500 A1 | 2/2005 | Boylan et al. |
| D566,272 S | 4/2008 | Walburg et al. | 2005/0059982 A1 | 3/2005 | Zung et al. |
| 7,361,183 B2 | 4/2008 | Ginn | 2005/0075665 A1 | 4/2005 | Brenzel et al. |
| 7,361,185 B2 | 4/2008 | O'Malley et al. | 2005/0085851 A1 | 4/2005 | Fiehler et al. |
| 7,393,363 B2 | 7/2008 | Ginn | 2005/0085854 A1 | 4/2005 | Ginn |
| 7,396,359 B1 | 7/2008 | Derowe et al. | 2005/0085855 A1 | 4/2005 | Forsberg |
| 7,431,727 B2 | 10/2008 | Cole et al. | 2005/0090859 A1 | 4/2005 | Ravikumar |
| 7,533,790 B1 | 5/2009 | Knodel et al. | 2005/0119695 A1 | 6/2005 | Carley et al. |
| 7,597,706 B2 | 10/2009 | Kanner et al. | 2005/0121042 A1 | 6/2005 | Belhe et al. |
| D611,144 S | 3/2010 | Reynolds | 2005/0149117 A1 | 7/2005 | Khosravi et al. |
| 7,819,895 B2 | 10/2010 | Ginn et al. | 2005/0152949 A1 | 7/2005 | Hotchkiss et al. |
| 2001/0007077 A1 | 7/2001 | Ginn et al. | 2005/0165357 A1 | 7/2005 | McGuckin et al. |
| 2001/0031972 A1 | 10/2001 | Robertson et al. | 2005/0169974 A1 | 8/2005 | Tenerz et al. |
| 2001/0046518 A1 | 11/2001 | Sawhney | 2005/0177189 A1 | 8/2005 | Ginn et al. |
| 2001/0047180 A1 | 11/2001 | Grudem et al. | 2005/0187564 A1 | 8/2005 | Jayaraman |
| 2002/0026215 A1 | 2/2002 | Redmond et al. | 2005/0216057 A1 | 9/2005 | Coleman et al. |
| 2002/0038127 A1 | 3/2002 | Blatter et al. | 2005/0222614 A1 | 10/2005 | Ginn et al. |
| 2002/0042622 A1 | 4/2002 | Vargas et al. | 2005/0234508 A1 | 10/2005 | Cummins et al. |
| 2002/0049427 A1 | 4/2002 | Wiener et al. | 2005/0245876 A1 | 11/2005 | Khosravi et al. |
| 2002/0058960 A1 | 5/2002 | Hudson et al. | 2005/0267528 A1 | 12/2005 | Ginn et al. |
| 2002/0072768 A1 | 6/2002 | Ginn | 2005/0267530 A1 | 12/2005 | Cummins et al. |
| 2002/0077657 A1 | 6/2002 | Ginn et al. | 2005/0273136 A1 | 12/2005 | Belef et al. |
| 2002/0082641 A1 | 6/2002 | Ginn et al. | 2005/0273137 A1 | 12/2005 | Ginn |
| 2002/0099389 A1 | 7/2002 | Michler et al. | 2005/0274768 A1 | 12/2005 | Cummins et al. |
| 2002/0106409 A1 | 8/2002 | Sawhney et al. | 2005/0283188 A1 | 12/2005 | Loshakove et al. |
| 2002/0107542 A1 | 8/2002 | Kanner et al. | 2006/0020270 A1 | 1/2006 | Jabba et al. |
| 2002/0133193 A1 | 9/2002 | Ginn et al. | 2006/0030867 A1 | 2/2006 | Zadno |
| 2002/0151921 A1 | 10/2002 | Kanner et al. | 2006/0034930 A1 | 2/2006 | Khosravi et al. |
| 2002/0183786 A1 | 12/2002 | Girton | 2006/0047313 A1 | 3/2006 | Khanna et al. |
| 2002/0188318 A1 * | 12/2002 | Carley et al. ............... 606/213 | 2006/0100664 A1 | 5/2006 | Pai et al. |
| 2002/0198589 A1 | 12/2002 | Leong | 2006/0135989 A1 | 6/2006 | Carley et al. |
| 2003/0004543 A1 | 1/2003 | Gleeson et al. | 2006/0144479 A1 | 7/2006 | Carley et al. |

| | | |
|---|---|---|
| 2006/0167484 A1 | 7/2006 | Carley et al. |
| 2006/0190014 A1 | 8/2006 | Ginn et al. |
| 2006/0190037 A1 | 8/2006 | Ginn et al. |
| 2006/0190038 A1 | 8/2006 | Carley et al. |
| 2006/0195123 A1 | 8/2006 | Ginn et al. |
| 2006/0195124 A1 | 8/2006 | Ginn et al. |
| 2006/0206146 A1 | 9/2006 | Tenerz |
| 2006/0253037 A1 | 11/2006 | Ginn et al. |
| 2006/0253072 A1 | 11/2006 | Pai et al. |
| 2006/0259049 A1 | 11/2006 | Harada et al. |
| 2006/0287674 A1 | 12/2006 | Ginn et al. |
| 2006/0293698 A1 | 12/2006 | Douk |
| 2007/0010853 A1 | 1/2007 | Ginn et al. |
| 2007/0010854 A1 | 1/2007 | Cummins et al. |
| 2007/0021778 A1 | 1/2007 | Carly |
| 2007/0049967 A1 | 3/2007 | Sibbitt, Jr. et al. |
| 2007/0049968 A1 | 3/2007 | Sibbitt, Jr. et al. |
| 2007/0060895 A1 | 3/2007 | Sibbitt, Jr. et al. |
| 2007/0060950 A1 | 3/2007 | Khosravi et al. |
| 2007/0083230 A1 | 4/2007 | Javois |
| 2007/0112304 A1 | 5/2007 | Voss |
| 2007/0112365 A1 | 5/2007 | Hilal et al. |
| 2007/0123817 A1 | 5/2007 | Khosravi et al. |
| 2007/0179527 A1 | 8/2007 | Eskuri et al. |
| 2007/0203506 A1 | 8/2007 | Sibbitt, Jr. et al. |
| 2007/0203507 A1 | 8/2007 | McLaughlin et al. |
| 2007/0225755 A1 | 9/2007 | Preinitz et al. |
| 2007/0225756 A1 | 9/2007 | Preinitz et al. |
| 2007/0225757 A1 | 9/2007 | Preinitz et al. |
| 2007/0225758 A1 | 9/2007 | Preinitz et al. |
| 2007/0239209 A1 | 10/2007 | Fallman |
| 2007/0250080 A1 | 10/2007 | Jones et al. |
| 2007/0265658 A1 | 11/2007 | Nelson et al. |
| 2007/0270904 A1 | 11/2007 | Ginn |
| 2007/0276416 A1 | 11/2007 | Ginn et al. |
| 2007/0276488 A1 | 11/2007 | Wachter et al. |
| 2007/0282352 A1 | 12/2007 | Carley et al. |
| 2008/0004636 A1 | 1/2008 | Walberg |
| 2008/0004640 A1 | 1/2008 | Ellingwood |
| 2008/0009794 A1 | 1/2008 | Bagaoisan et al. |
| 2008/0058839 A1* | 3/2008 | Nobles et al. ............... 606/148 |
| 2008/0065151 A1 | 3/2008 | Ginn |
| 2008/0065152 A1 | 3/2008 | Carley |
| 2008/0086075 A1* | 4/2008 | Isik et al. ................. 604/27 |
| 2008/0093414 A1 | 4/2008 | Bender et al. |
| 2008/0114395 A1 | 5/2008 | Mathisen et al. |
| 2008/0210737 A1 | 9/2008 | Ginn et al. |
| 2008/0221616 A1 | 9/2008 | Ginn et al. |
| 2008/0243148 A1 | 10/2008 | Mikkaichi et al. |
| 2008/0269801 A1 | 10/2008 | Coleman et al. |
| 2008/0269802 A1 | 10/2008 | Coleman et al. |
| 2008/0272173 A1 | 11/2008 | Coleman et al. |
| 2008/0300628 A1 | 12/2008 | Ellingwood |
| 2008/0312666 A1 | 12/2008 | Ellingwood et al. |
| 2008/0312686 A1 | 12/2008 | Ellingwood |
| 2008/0312740 A1 | 12/2008 | Wachter et al. |
| 2009/0112306 A1 | 4/2009 | Bonsignore et al. |
| 2009/0137900 A1 | 5/2009 | Bonner et al. |
| 2009/0157101 A1 | 6/2009 | Reyes et al. |
| 2009/0157102 A1 | 6/2009 | Reynolds et al. |
| 2009/0157103 A1 | 6/2009 | Walberg et al. |
| 2009/0177212 A1 | 7/2009 | Carley et al. |
| 2009/0177213 A1 | 7/2009 | Carley et al. |
| 2009/0187215 A1 | 7/2009 | Mackiewicz et al. |
| 2009/0216267 A1 | 8/2009 | Willard et al. |
| 2009/0230168 A1 | 9/2009 | Coleman et al. |
| 2009/0254119 A1 | 10/2009 | Sibbitt, Jr. et al. |
| 2009/0287244 A1 | 11/2009 | Kokish |
| 2010/0114156 A1 | 5/2010 | Mehl |
| 2010/0114159 A1 | 5/2010 | Roorda et al. |
| 2010/0130965 A1 | 5/2010 | Sibbitt, Jr. |
| 2010/0179567 A1 | 7/2010 | Voss et al. |
| 2010/0179571 A1 | 7/2010 | Voss |
| 2010/0179572 A1 | 7/2010 | Voss et al. |
| 2010/0179589 A1 | 7/2010 | Roorda et al. |
| 2010/0179590 A1 | 7/2010 | Fortson et al. |
| 2010/0185234 A1 | 7/2010 | Fortson et al. |

FOREIGN PATENT DOCUMENTS

| | | |
|---|---|---|
| CA | 2 339 060 | 2/2000 |
| DE | 197 11 288 | 10/1998 |
| DE | 29723736 U1 | 4/1999 |
| DE | 19859952 | 2/2000 |
| DE | 102006056283 | 6/2008 |
| EP | 0 386 361 | 9/1990 |
| EP | 0 534 696 | 3/1993 |
| EP | 0 756 851 | 2/1997 |
| EP | 0 774 237 | 5/1997 |
| EP | 0 858 776 | 8/1998 |
| EP | 0 941 697 | 9/1999 |
| EP | 1 867 287 | 12/2007 |
| FR | 2 443 238 | 7/1980 |
| FR | 2 715 290 | 7/1995 |
| FR | 2 722 975 | 2/1996 |
| FR | 2 768 324 | 3/1999 |
| GB | 1 358 466 | 7/1974 |
| GB | 2 075 144 | 11/1981 |
| GB | 2 397 240 | 7/2004 |
| IE | S2000/0722 | 10/2001 |
| IE | S2000/0724 | 10/2001 |
| IE | S2001/0547 | 7/2002 |
| IE | S2001/0815 | 7/2002 |
| IE | S2001/0748 | 8/2002 |
| IE | S2001/0749 | 8/2002 |
| IE | S2002/0452 | 12/2002 |
| IE | S2002/0664 | 2/2003 |
| IE | S2002/0665 | 2/2003 |
| IE | S2002/0451 | 7/2003 |
| IE | S2002/0552 | 7/2003 |
| IE | S2003/0424 | 12/2003 |
| IE | S2003/0490 | 1/2004 |
| IE | S2004/0368 | 11/2005 |
| IE | S2005/0342 | 11/2005 |
| JP | 58-181006 | 12/1983 |
| JP | 12 74750 | 11/1989 |
| JP | 11500642 | 8/1997 |
| JP | 2000102546 | 4/2000 |
| NL | 9302140 | 7/1995 |
| PL | 171425 | 4/1997 |
| RU | 2086192 | 8/1997 |
| SU | 495067 | 12/1975 |
| SU | 912155 | 3/1982 |
| SU | 1243708 | 7/1986 |
| SU | 1324650 | 7/1987 |
| SU | 1405828 | 6/1988 |
| SU | 1456109 | 2/1989 |
| SU | 1560133 | 4/1990 |
| WO | WO 96/24291 | 8/1996 |
| WO | WO 97/07741 | 3/1997 |
| WO | WO 97/20505 | 6/1997 |
| WO | WO 97/27897 | 8/1997 |
| WO | WO 98/06346 | 2/1998 |
| WO | WO 98/06448 | 2/1998 |
| WO | WO 98/16161 | 4/1998 |
| WO | WO 98/17179 | 4/1998 |
| WO | WO 98/18389 | 5/1998 |
| WO | WO 98/24374 | 6/1998 |
| WO | WO 98/25508 | 6/1998 |
| WO | WO 98/58591 | 12/1998 |
| WO | WO 99/21491 | 5/1999 |
| WO | WO 99/40849 | 8/1999 |
| WO | WO 99/60941 | 12/1999 |
| WO | WO 99/62408 | 12/1999 |
| WO | WO 99/62415 | 12/1999 |
| WO | WO 00/06029 | 2/2000 |
| WO | WO 00/07505 | 2/2000 |
| WO | WO 00/07640 | 2/2000 |
| WO | WO 00/27311 | 5/2000 |
| WO | WO 00/27313 | 5/2000 |
| WO | WO 00/56223 | 9/2000 |
| WO | WO 00/56227 | 9/2000 |
| WO | WO 00/56228 | 9/2000 |
| WO | WO 00/71032 | 11/2000 |
| WO | WO 01/21058 | 3/2001 |
| WO | WO 01/35832 | 5/2001 |
| WO | WO 01/47594 | 7/2001 |
| WO | WO 01/49186 | 7/2001 |

| | | |
|---|---|---|
| WO | WO 01/91628 | 12/2001 |
| WO | WO 02/19915 | 3/2002 |
| WO | WO 02/19920 | 3/2002 |
| WO | WO 02/19922 | 3/2002 |
| WO | WO 02/19924 | 3/2002 |
| WO | WO 02/28286 | 4/2002 |
| WO | WO 02/38055 | 5/2002 |
| WO | WO 02/45593 | 6/2002 |
| WO | WO 02/45594 | 6/2002 |
| WO | WO 02/062234 | 8/2002 |
| WO | WO 02/098302 | 12/2002 |
| WO | WO 03/013363 | 2/2003 |
| WO | WO 03/013364 | 2/2003 |
| WO | WO 03/047434 | 6/2003 |
| WO | WO 03/071955 | 9/2003 |
| WO | WO 03/071956 | 9/2003 |
| WO | WO 03/071957 | 9/2003 |
| WO | WO 03/094748 | 11/2003 |
| WO | WO 03/101310 | 12/2003 |
| WO | WO 2004/004578 | 1/2004 |
| WO | WO 2004/012602 | 2/2004 |
| WO | WO 2004/060169 | 7/2004 |
| WO | WO 2004/069054 | 8/2004 |
| WO | WO 2005/000126 | 1/2005 |
| WO | WO 2005/006990 | 1/2005 |
| WO | WO 2005/041782 | 5/2005 |
| WO | WO 2005/063129 | 7/2005 |
| WO | WO 2005/082256 | 9/2005 |
| WO | WO 2005/092204 | 10/2005 |
| WO | WO 2005/110240 | 11/2005 |
| WO | WO 2005/112782 | 12/2005 |
| WO | WO 2005/115251 | 12/2005 |
| WO | WO 2005/115521 | 12/2005 |
| WO | WO 2006/000514 | 1/2006 |
| WO | WO 2006/026116 | 3/2006 |
| WO | WO 2006/052611 | 5/2006 |
| WO | WO 2006/052612 | 5/2006 |
| WO | WO 2006/078578 | 7/2006 |
| WO | WO 2006/083889 | 8/2006 |
| WO | WO 2006/115901 | 11/2006 |
| WO | WO 2006/115904 | 11/2006 |
| WO | WO 2006/118877 | 11/2006 |
| WO | WO 2007/005585 | 1/2007 |
| WO | WO 2007/025014 | 3/2007 |
| WO | WO 2007/025017 | 3/2007 |
| WO | WO 2007/025018 | 3/2007 |
| WO | WO 2007/025019 | 3/2007 |
| WO | WO 2007/081836 | 7/2007 |
| WO | WO 2007/088069 | 8/2007 |
| WO | WO 2008/031102 | 3/2008 |
| WO | WO 2008/036384 | 3/2008 |
| WO | WO 2008/074027 | 6/2008 |
| WO | WO 2008/150915 | 12/2008 |
| WO | WO 2009/079091 | 6/2009 |
| WO | WO 2010/031050 | 3/2010 |
| WO | WO 2010/062693 | 6/2010 |
| WO | WO 2010/081101 | 7/2010 |
| WO | WO 2010/081102 | 7/2010 |
| WO | WO 2010/081103 | 7/2010 |
| WO | WO 2010/081106 | 7/2010 |
| ZA | 200100527 | 1/2001 |
| ZA | 200100528 | 1/2001 |

OTHER PUBLICATIONS

U.S. Appl. No. 10/264,306, Jun. 15, 2010, Office Action.
U.S. Appl. No. 10/435,104, Jul. 23, 2009, Notice of Allowance.
U.S. Appl. No. 10/435,104, Jun. 2, 2010, Office Action.
U.S. Appl. No. 10/667,144, Jun. 22, 2010, Office Action.
U.S. Appl. No. 10/669,313, Oct. 31, 2005, Office Action.
U.S. Appl. No. 11/048,503, Jul. 30, 2010, Notice of Allowance.
U.S. Appl. No. 11/113,549, Jul. 6, 2010, Office Action.
U.S. Appl. No. 11/198,811, Jun. 29, 2010, Notice of Allowance.
U.S. Appl. No. 11/390,586, Jul. 6, 2010, Office Action.
U.S. Appl. No. 11/396,731, Jun. 29, 2010, Office Action.
U.S. Appl. No. 11/852,190, Jun. 24, 2010, Office Action.
U.S. Appl. No. 11/959,334, Jul. 23, 2010, Notice of Allowance.
U.S. Appl. No. 12/113,851, Jun. 24, 2010, Office Action.
U.S. Appl. No. 12/403,277, Jul. 8, 2010, Office Action.
U.S. Appl. No. 60/693,531, filed Jun. 24, 2005, Carly.
U.S. Appl. No. 60/696,069, filed Jul. 1, 2005, Pantages et al.
U.S. Appl. No. 60/711,279, filed Aug. 24, 2005, Sibbitt Jr. et al.
U.S. Appl. No. 60/726,985, filed Oct. 14, 2005, Sibbitt Jr. et al.
U.S. Appl. No. 60/793,444, filed Apr. 20, 2006, Jones et al.
U.S. Appl. No. 60/843,325, filed Sep. 8, 2006, Carly.
U.S. Appl. No. 60/946,026, filed Jun. 25, 2007, Ellingwood.
U.S. Appl. No. 60/946,030, filed Jun. 25, 2007, Voss et al.
U.S. Appl. No. 60/946,042, filed Jun. 25, 2007, Ellingwood et al.
U.S. Appl. No. 61/097,072, filed Sep. 15, 2008, Sibbitt Jr. et al.
U.S. Appl. No. 61/139,995, filed Dec. 22, 2008, Clark.
U.S. Appl. No. 61/141,597, filed Dec. 30, 2008, Clark.
U.S. Appl. No. 12/113,092, filed Apr. 30, 2008, Ginn et al.
U.S. Appl. No. 12/393,877, filed Feb. 26, 2009, Ellingwood et al.
U.S. Appl. No. 12/481,377, filed Jun. 9, 2009, Clark.
U.S. Appl. No. 12/642,319, filed Dec. 18, 2009, Clark.
"Hand tool for forming telephone connections—comprises pliers with reciprocably driven ram crimping clip around conductors against anvil".
Database WPI; Section PQ, Week 200120; Derwent Publications Ltd., London GB; AN2001-203165; XP002199926 & ZA 200 100 528 A (Anthony T), Feb. 28, 2001 abstract.
Deepak Mital et al, Renal Transplantation Without Sutures Using the Vascular Clipping System for Renal Artery and Vein Anastomosis—A New Technique, Transplantation Issue, Oct. 1996, pp. 1171-1173, vol. 62—No. 8, Section of Transplantation Surgery, Department of General Surgery, Rush-Presbyterian/St. Luke's Medical Center, Chigago, IL.
DL Wessel et al, Outpatient closure of the patent ductus arteriosus, Circulation, May 1988, pp. 1068-1071, vol. 77—No. 5, Department of Anesthesia, Children's Hospital, Boston, MA.
E Pikoulis et al, Arterial reconstruction with vascular clips is safe and quicker than sutured repair, Cardiovascular Surgery, Dec. 1998, pp. 573-578(6), vol. 6—No. 6, Department of Surgery, Uniformed Services University of the Health Sciences, Bethesda, MD.
G Gershony et al, Novel vascular sealing device for closure of percutaneous vascular access sites, Cathet. Cardiovasc. Diagn., Jan. 1998, pp. 82-88, vol. 45.
H De Swart et al, A new hemostatic puncture closure device for the immediate sealing of arterial puncture sites, American journal of cardiology, Aug. 1993, pp. 445-449, vol. 72—No. 5, Department of Cardiology, Academic Hospital Maastricht, The Netherlands.
Harrith M. Hasson M.D. , Laparoscopic Cannula Cone with Means for Cannula Stabilization and Wound Closure, The Journal of the American Association of Gynecologic Laparoscopists, May 1998, pp. 183-185, vol. 5—No. 2, Division of Obstetrics and Gynecology, University of Chicago, Chigago, IL.
J. Findlay et al, Carotid Arteriotomy Closure Using a Vascular Clip System, Neurosurgery, Mar. 1998, pp. 550-554, vol. 42—No. 3, Division of Neurosurgery, University of Alberta, Edmonton, Canada.
Jeremy L Gilbert Phd, Wound Closure Biomaterials and Devices, Shock., Mar. 1999, p. 226, vol. 11—No. 3, Institution Northwestern University (editorial review).
Jochen T. Cremer, MD, et al, Different approaches for minimally invasive closure of atrial septal defects, Ann. Thorac. Surg., Nov. 1998, pp. 1648-1652, vol. 67, a Division of Thoracic and Cardiovascular Surgery, Surgical Center, Hannover Medical School. Hannover, Germany.
K Narayanan et al, Simultaneous primary closure of four fasciotomy wounds in a single setting using the Sure-Closure device, Injury, Jul. 1996, pp. 449-451, vol. 27—No. 6, Department of Surgery, Mercy Hospital of Pittsburgh, PA.
Marshall A.C., Lock J.E., Structural and Compliant Anatomy of the Patent Foramen Ovale in Patients Undergoing Transcatheter Closure, Am Heart J Aug. 2000; 140(2); pp. 303-307.
MD Gonze et al, Complications associated with percutaneous closure devices, Conference: Annual Meeting of the Society for Clinical Vascular Surgery, The American journal of surgery, Mar. 1999, pp. 209-211, vol. 178, No. 3, Department of Surgery, Section of Vascular Surgery, Ochsner Medical Institutions, New Orleans, LA.

MD Hellinger et al, Effective peritoneal and fascial closure of abdominal trocar sites utilizing the Endo-Judge, J Laparoendosc Surg., Oct. 1996, pp. 329-332, vol. 6—No. 5, Orlando Regional Medical Center, FL.

Michael Gianturco, A Play on Catheterization, Forbes, Dec. 1996, p. 146, vol. 158—No. 15.

OM Elashry et al, Comparative clinical study of port-closure techniques following laparoscopic surgery, Department of Surgery, Mallickrodt Institute of Radiography, J Am Coll Surg., Oct. 1996, pp. 335-344, vol. 183—No. 4.

P M N Werker, et al, Review of facilitated approaches to vascular anastomosis surgery, Conference: Utrecht MICABG Workshop 2, The Annals of thoracic surgery, Apr. 1996, pp. S122-S127, vol. 63—No. 6, Department of Plastic, Reconstructive and Hand surgery, University Hospital Utrecht Netherlands Departments of Cardiology and Cardiopulmonary Surgery, Heart Lung Institute, Utrecht Netherlands.; Utrect University Hospital Utrecht Netherlands.

Peter Rhee MD et al, Use of Titanium Vascular Staples in Trauma, Journal of Trauma-Injury Infection & Critical Care, Dec. 1998, pp. 1097-1099, vol. 45—No. 6, Institution from the Department of Surgery, Washington Hospital Center, Washington DC, and Uniformed Services University of the Health Sciences, Bethesda, Maryland.

ProstarXL—Percutaneous Vascular Surgical Device, www.Archive. org, Jun. 1998, Original Publisher: http://prostar.com, may also be found at http://web.archive.org/web/19980630040429/www.perclose.com/html/prstrxl.html.

SA Beyer-Enke et al, Immediate sealing of arterial puncture site following femoropopliteal angioplasty: A prospective randomized trial, Cardiovascular and Interventional Radiology 1996, Nov.-Dec. 1996, pp. 406-410, vol. 19—No. 6, Gen Hosp North, Dept Dianost & Intervent Radiol, Nurnberg, Germany (Reprint).

Scott Hensley, Closing Wounds. New Devices seal arterial punctures in double time, Modern Healthcare (United States), Mar. 23, 2008, p. 48.

Sigmund Silber et al, A novel vascular device for closure of percutaneous arterial access sites, The American Journal of Cardiology, Apr. 1999, pp. 1248-1252, vol. 83—No. 8.

Simonetta Blengino et al, A Randomized Study of the 8 French Hemostatic Puncture Closure Device vs Manual Compression After Coronary Interventions, Journal of the American College of Cardiology, Feb. 1995, p. 262A, vol. 25.—No. 2, Supplement 1.

Stretch Comb by Scunci, retrieved via internet at www.scunci.com/productdetail by examiner on Oct. 9, 2007, publication date unavailable.

Swee Lian Tan, MD, Phd, FACS, Explanation of Infected Hemostatic Puncture Closure Devices—A Case Report, Vascular and Endovascular Surgery, 1999, pp. 507-510, vol. 33—No. 5, Parkland Medical Center, Derry, New Hampshire.

SY Nakada et al, Comparison of newer laparoscopic port closure techniques in the porcine model, J Endourol, Oct. 1995, pp. 397-401, vol. 9—No. 5, Department of Surgery/Urology, University of Wisconsin Medical School, Madison.

Taber's Cyclopedic Medical Dictionary, 18th Ed. 1997, pp. 747 and 1420.

Thomas P. Baum RPA-C et al, Delayed Primary Closure Using Silastic Vessel Loops and Skin Staples: Description of the Technique and Case Reports, Annals of Plastic Surgery, Mar. 1999, pp. 337-340, vol. 42—No. 3, Institution Department of Plastic and Reconstructive Surgery, Albert Einstein College of Medicine and Montefiore Medical Center, Bronx, NY.

Tomoaki Hinohara, Percutaneous vascular surgery (Prostar® Plus and Techstar® for femoral artery site closure), Interventional Cardiology Newsletter, May-Jul. 1997, pp. 19-28, vol. 5—No. 3-4.

UT Aker et al, Immediate arterial hemostasis after cardiac catheterization: initial experience with a new puncture closure device, Cathet Cardiovasc Diagn, Mar. 1994, pp. 228-232, vol. 33—No. 3, Missouri Baptist Medical Center, St. Louis.

Wei Qu et al, An absorbable pinned-ring device for microvascular anastomosis of vein grafts: Experimental studies, Microsurgery 1999, Mar. 1999, pp. 128-134, vol. 19—No. 3, Department of Orthopaedic Surgery, Hiroshima University School of Medicine, Hiroshima, Japan.

William G. Kussmaul III MD, et al., Rapid arterial hemostasis and decreased access site complications after cardiac catheterization and angioplasty: Results of a randomized trial of a novel hemostatic device, Journal of the American College of Cardiology, Jun. 1995, pp. 1685-1692, vol. 25—No. 7.

U.S. Appl. No. 09/478,179, Nov. 6, 2000, Notice of Allowance.
U.S. Appl. No. 09/478,179, Feb. 15, 2001, Issue Notification.
U.S. Appl. No. 09/546,998, May 6, 2002, Notice of Allowance.
U.S. Appl. No. 09/546,998, Sep. 19, 2002, Issue Notification.
U.S. Appl. No. 09/610,238, Mar. 26, 2001, Notice of Allowance.
U.S. Appl. No. 09/610,238, Sep. 5, 2001, Office Action.
U.S. Appl. No. 09/610,238, Feb. 11, 2002, Notice of Allowance.
U.S. Appl. No. 09/610,238, May 3, 2002, Issue Notification.
U.S. Appl. No. 09/680,837, Jul. 9, 2002, Office Action.
U.S. Appl. No. 09/680,837, Nov. 6, 2002, Office Action.
U.S. Appl. No. 09/680,837, Mar. 25, 2003, Office Action.
U.S. Appl. No. 09/680,837, Jun. 16, 2003, Notice of Allowance.
U.S. Appl. No. 09/680,837, Sep. 11, 2003, Issue Notification.
U.S. Appl. No. 09/732,178, Aug. 1, 2002, Office Action.
U.S. Appl. No. 09/732,178, Dec. 24, 2002, Office Action.
U.S. Appl. No. 09/732,178, Jun. 10, 2003, Office Action.
U.S. Appl. No. 09/732,178, Jul. 3, 2003, Office Action.
U.S. Appl. No. 09/732,178, Nov. 17, 2003, Notice of Allowance.
U.S. Appl. No. 09/732,178, Mar. 25, 2004, Issue Notification.
U.S. Appl. No. 09/732,835, Sep. 11, 2003, Office Action.
U.S. Appl. No. 09/732,835, Feb. 9, 2004, Office Action.
U.S. Appl. No. 09/732,835, Mar. 17, 2004, Notice of Allowance.
U.S. Appl. No. 09/764,813, Mar. 26, 2001, Office Action.
U.S. Appl. No. 09/764,813, Jun. 4, 2001, Notice of Allowance.
U.S. Appl. No. 09/764,813, Aug. 6, 2001, Issue Notification.
U.S. Appl. No. 09/933,299, Feb. 26, 2003, Office Action.
U.S. Appl. No. 09/933,299, Jun. 16, 2003, Notice of Allowance.
U.S. Appl. No. 09/933,299, Sep. 25, 2003, Issue Notification.
U.S. Appl. No. 09/948,813, Jan. 31, 2003, Notice of Allowance.
U.S. Appl. No. 09/948,813, Jun. 5, 2003, Issue Notification.
U.S. Appl. No. 09/949,398, Mar. 4, 2003, Office Action.
U.S. Appl. No. 09/949,398, Jul. 28, 2003, Notice of Allowance.
U.S. Appl. No. 09/949,398, Dec. 11, 2003, Issue Notification.
U.S. Appl. No. 09/949,438, Dec. 17, 2002, Office Action.
U.S. Appl. No. 09/949,438, Apr. 21, 2003, Notice of Allowance.
U.S. Appl. No. 09/949,438, Aug. 21, 2003, Issue Notification.
U.S. Appl. No. 10/006,400, Aug. 27, 2004, Office Action.
U.S. Appl. No. 10/006,400, Feb. 23, 2005, Office Action.
U.S. Appl. No. 10/006,400, Apr. 11, 2005, Office Action.
U.S. Appl. No. 10/006,400, Jul. 27, 2005, Office Action.
U.S. Appl. No. 10/006,400, Mar. 6, 2006, Office Action.
U.S. Appl. No. 10/006,400, May 24, 2006, Office Action.
U.S. Appl. No. 10/006,400, Oct. 26, 2006, Office Action.
U.S. Appl. No. 10/006,400, Apr. 19, 2007, Office Action.
U.S. Appl. No. 10/006,400, Apr. 2, 2008, Office Action.
U.S. Appl. No. 10/006,400, Jan. 2, 2009, Office Action.
U.S. Appl. No. 10/006,400, Jul. 9, 2009, Notice of Allowance.
U.S. Appl. No. 10/006,400, Jan. 13, 2010, Notice of Allowance.
U.S. Appl. No. 10/006,400, Apr. 27, 2010, Notice of Allowance.
U.S. Appl. No. 10/081,717, Sep. 29, 2003, Notice of Allowance.
U.S. Appl. No. 10/081,717, Feb. 5, 2004, Issue Notification.
U.S. Appl. No. 10/081,723, Sep. 29, 2004, Office Action.
U.S. Appl. No. 10/081,723, May 13, 2005, Notice of Allowance.
U.S. Appl. No. 10/081,725, Feb. 9, 2004, Notice of Allowance.
U.S. Appl. No. 10/081,725, Apr. 13, 2004, Office Action.
U.S. Appl. No. 10/081,725, May 27, 2004, Issue Notification.
U.S. Appl. No. 10/081,726, Apr. 11, 2003, Notice of Allowance.
U.S. Appl. No. 10/081,726, Jun. 9, 2003, Office Action.
U.S. Appl. No. 10/081,726, Sep. 4, 2003, Issue Notification.
U.S. Appl. No. 10/147,774, Nov. 4, 2004, Office Action.
U.S. Appl. No. 10/147,774, May 4, 2005, Office Action.
U.S. Appl. No. 10/147,774, Oct. 18, 2005, Office Action.
U.S. Appl. No. 10/147,774, Apr. 18, 2007, Notice of Allowance.
U.S. Appl. No. 10/147,774, Sep. 27, 2007, Notice of Allowance.
U.S. Appl. No. 10/147,774, Feb. 4, 2008, Notice of Allowance.
U.S. Appl. No. 10/147,774, Jun. 30, 2008, Office Action.
U.S. Appl. No. 10/147,774, Mar. 18, 2009, Office Action.
U.S. Appl. No. 10/147,774, Oct. 26, 2009, Office Action.

U.S. Appl. No. 10/240,183, Jul. 27, 2004, Office Action.
U.S. Appl. No. 10/240,183, Dec. 17, 2004, Office Action.
U.S. Appl. No. 10/240,183, Mar. 9, 2005, Notice of Allowance.
U.S. Appl. No. 10/240,183, Aug. 11, 2006, Response to 312.
U.S. Appl. No. 10/264,306 Feb. 9, 2005, Office Action.
U.S. Appl. No. 10/264,306, May 26, 2005, Office Action.
U.S. Appl. No. 10/264,306, Oct. 4, 2005, Office Action.
U.S. Appl. No. 10/264,306, May 10, 2006, Notice of Allowance.
U.S. Appl. No. 10/264,306, Jul. 2, 2007, Notice of Allowance.
U.S. Appl. No. 10/264,306, Feb. 4, 2008, Notice of Allowance.
U.S. Appl. No. 10/264,306, Jun. 27, 2008, Office Action.
U.S. Appl. No. 10/264,306, Feb. 26, 2009, Office Action.
U.S. Appl. No. 10/264,306, Aug. 13, 2009, Office Action.
U.S. Appl. No. 10/264,306, Jan. 27, 2010, Office Action.
U.S. Appl. No. 10/335,075, Aug. 10, 2005, Office Action.
U.S. Appl. No. 10/335,075, Dec. 19, 2005, Office Action.
U.S. Appl. No. 10/335,075, Apr. 21, 2006, Office Action.
U.S. Appl. No. 10/335,075, Dec. 27, 2006, Notice of Allowance.
U.S. Appl. No. 10/335,075, Apr. 11, 2007, Issue Notification.
U.S. Appl. No. 10/356,214, Nov. 30, 2005, Office Action.
U.S. Appl. No. 10/356,214, Aug. 23, 2006, Office Action.
U.S. Appl. No. 10/356,214, Feb. 13, 2007, Office Action.
U.S. Appl. No. 10/356,214, Sep. 12, 2007, Office Action.
U.S. Appl. No. 10/356,214, Mar. 6, 2008, Office Action.
U.S. Appl. No. 10/356,214, Nov. 4, 2008, Office Action.
U.S. Appl. No. 10/356,214, Apr. 29, 2009, Office Action.
U.S. Appl. No. 10/356,214, Jan. 13, 2010, Notice of Allowance.
U.S. Appl. No. 10/356,214, May 13, 2010, Notice of Allowance.
U.S. Appl. No. 10/435,104, Jun. 10, 2004, Office Action.
U.S. Appl. No. 10/435,104, Sep. 21, 2004, Office Action.
U.S. Appl. No. 10/435,104, Jan. 3, 2006, Examiner Amendment.
U.S. Appl. No. 10/435,104, Feb. 15, 2006, Issue Notification.
U.S. Appl. No. 10/435,104, May 16, 2006, Office Action.
U.S. Appl. No. 10/435,104, Dec. 28, 2006, Notice of Allowance.
U.S. Appl. No. 10/435,104, May 23, 2007, Issue Notification.
U.S. Appl. No. 10/435,104, Jul. 10, 2007, Notice of Allowance.
U.S. Appl. No. 10/435,104, Aug. 2, 2007, Notice of Allowance.
U.S. Appl. No. 10/435,104, Oct. 26, 2007, Notice of Allowance.
U.S. Appl. No. 10/435,104, Nov. 14, 2007, Supplemental Notice of Allowance.
U.S. Appl. No. 10/435,104, Apr. 4, 2008, Notice of Allowance.
U.S. Appl. No. 10/435,104, Sep. 26, 2008, Notice of Allowance.
U.S. Appl. No. 10/435,104, Dec. 22, 2008, Supplemental Notice of Allowance.
U.S. Appl. No. 10/435,104, Jan. 20, 2010, Notice of Allowance.
U.S. Appl. No. 10/455,768, Nov. 16, 2004, Office Action.
U.S. Appl. No. 10/455,768, Apr. 6, 2005, Notice of Allowance.
U.S. Appl. No. 10/486,067, Jan. 10, 2006, Office Action.
U.S. Appl. No. 10/486,067, Sep. 20, 2006, Notice of Allowance.
U.S. Appl. No. 10/486,067, Dec. 27, 2006, Issue Notification.
U.S. Appl. No. 10/486,070, Apr. 20, 2005, Office Action.
U.S. Appl. No. 10/486,070, Aug. 10, 2005, Office Action.
U.S. Appl. No. 10/486,070, Oct. 18, 2005, Notice of Allowance.
U.S. Appl. No. 10/517,004, Aug. 13, 2007, Office Action.
U.S. Appl. No. 10/517,004, Jan. 30, 2008, Office Action.
U.S. Appl. No. 10/517,004, Aug. 13, 2008, Notice of Allowance.
U.S. Appl. No. 10/517,004, Feb. 10, 2009, Notice of Allowance.
U.S. Appl. No. 10/517,004, Jun. 26, 2009, Notice of Allowance.
U.S. Appl. No. 10/517,004, Jan. 11, 2010, Notice of Allowance.
U.S. Appl. No. 10/517,004, Apr. 23, 2010, Notice of Allowance.
U.S. Appl. No. 10/519,778, Feb. 23, 2006, Office Action.
U.S. Appl. No. 10/519,778, May 31, 2006, Notice of Allowance.
U.S. Appl. No. 10/541,083, Oct. 16, 2007, Office Action.
U.S. Appl. No. 10/541,083, Oct. 31, 2007, Office Action.
U.S. Appl. No. 10/541,083, May 5, 2008, Office Action.
U.S. Appl. No. 10/541,083, Sep. 19, 2008, Notice of Allowance.
U.S. Appl. No. 10/541,083, Dec. 29, 2008, Notice of Allowance.
U.S. Appl. No. 10/541,083, Apr. 16, 2009, Notice of Allowance.
U.S. Appl. No. 10/541,083, Sep. 30, 2009, Notice of Allowance.
U.S. Appl. No. 10/541,083, Feb. 5, 2010, Notice of Allowance.
U.S. Appl. No. 10/541,083, May 10, 2010, Notice of Allowance.
U.S. Appl. No. 10/616,832, Jun. 30, 2006, Office Action.
U.S. Appl. No. 10/616,832, Oct. 20, 2006, Office Action.
U.S. Appl. No. 10/616,832, May 29, 2007, Office Action.
U.S. Appl. No. 10/616,832, Jan. 22, 2008, Office Action.
U.S. Appl. No. 10/616,832, Sep. 17, 2008, Office Action.
U.S. Appl. No. 10/616,832, Jul. 21, 2009, Office Action.
U.S. Appl. No. 10/616,832, Jan. 11, 2010, Notice of Allowance.
U.S. Appl. No. 10/616,832, May 12, 2010, Notice of Allowance.
U.S. Appl. No. 10/617,090, Mar. 22, 2005, Office Action.
U.S. Appl. No. 10/617,090, Jul. 6, 2005, Notice of Allowance.
U.S. Appl. No. 10/617,090, Oct. 5, 2005, Notice of Allowance.
U.S. Appl. No. 10/617,090, Feb. 1, 2006, Issue Notification.
U.S. Appl. No. 10/638,115, Sep. 22, 2006, Restriction Requirement.
U.S. Appl. No. 10/638,115, Jan. 31, 2007, Office Action.
U.S. Appl. No. 10/638,115, Sep. 18, 2007, Office Action.
U.S. Appl. No. 10/638,115, Feb. 7, 2008, Office Action.
U.S. Appl. No. 10/638,115, Oct. 29, 2008, Office Action.
U.S. Appl. No. 10/638,115, May 7, 2009, Notice of Allowance.
U.S. Appl. No. 10/638,115, Dec. 1, 2009, Notice of Allowance.
U.S. Appl. No. 10/638,115, Apr. 2, 2010, Notice of Allowance.
U.S. Appl. No. 10/667,144, Sep. 19, 2006, Office Action.
U.S. Appl. No. 10/667,144, May 2, 2007, Office Action.
U.S. Appl. No. 10/667,144, Nov. 19, 2007, Office Action.
U.S. Appl. No. 10/667,144, Dec. 5, 2007, Office Action.
U.S. Appl. No. 10/667,144, May 12, 2008, Office Action.
U.S. Appl. No. 10/667,144, Mar. 24, 2009, Office Action.
U.S. Appl. No. 10/667,144, Nov. 23, 2009, Office Action.
U.S. Appl. No. 10/669,313, Jan. 11, 2006, Notice of Allowance.
U.S. Appl. No. 10/669,313, Jun. 28, 2006, Notice of Allowance.
U.S. Appl. No. 10/669,313, Nov. 15, 2006, Issue Notification.
U.S. Appl. No. 10/682,459, Sep. 15, 2006, Office Action.
U.S. Appl. No. 10/682,459, Apr. 18, 2007, Office Action.
U.S. Appl. No. 10/682,459, Apr. 2, 2008, Office Action.
U.S. Appl. No. 10/682,459, Dec. 4, 2008, Office Action.
U.S. Appl. No. 10/682,459, Jun. 10, 2009, Office Action.
U.S. Appl. No. 10/682,459, Dec. 23, 2009, Office Action.
U.S. Appl. No. 10/682,459, Apr. 28, 2010, Office Action.
U.S. Appl. No. 10/786,444, Oct. 30, 2006, Office Action.
U.S. Appl. No. 10/786,444, Apr. 17, 2007, Office Action.
U.S. Appl. No. 10/786,444, Aug. 31, 2007, Office Action.
U.S. Appl. No. 10/786,444, Apr. 24, 2008, Office Action.
U.S. Appl. No. 10/786,444, Oct. 17, 2008, Office Action.
U.S. Appl. No. 10/786,444, Jun. 18, 2009, Office Action.
U.S. Appl. No. 10/786,444, Jan. 14, 2010, Office Action.
U.S. Appl. No. 10/787,073, Nov. 30, 2006, Office Action.
U.S. Appl. No. 10/787,073, Sep. 5, 2007, Office Action.
U.S. Appl. No. 10/787,073, Feb. 22, 2008, Office Action.
U.S. Appl. No. 10/787,073, Nov. 12, 2008, Office Action.
U.S. Appl. No. 10/787,073, Aug. 13, 2009, Office Action.
U.S. Appl. No. 10/787,073, Feb. 17, 2010, Notice of Allowance.
U.S. Appl. No. 10/908,721, Oct. 19, 2006, Office Action.
U.S. Appl. No. 10/908,721, Aug. 10, 2007, Office Action.
U.S. Appl. No. 10/908,721, Jan. 25, 2008, Office Action.
U.S. Appl. No. 10/908,721, Nov. 25, 2008, Office Action.
U.S. Appl. No. 10/908,721, Jun. 23, 2009, Office Action.
U.S. Appl. No. 10/908,721, Feb. 2, 2010, Office Action.
U.S. Appl. No. 11/048,503, Mar. 13, 2009, Office Action.
U.S. Appl. No. 11/048,503, Jun. 26, 2009, Office Action.
U.S. Appl. No. 11/048,503, Jan. 11, 2010, Notice of Allowance.
U.S. Appl. No. 11/048,503, Apr. 26, 2010, Notice of Allowance.
U.S. Appl. No. 11/113,549, Feb. 6, 2007, Office Action.
U.S. Appl. No. 11/113,549, May 30, 2007, Office Action.
U.S. Appl. No. 11/113,549, Nov. 9, 2007, Office Action.
U.S. Appl. No. 11/113,549, Apr. 16, 2008, Office Action.
U.S. Appl. No. 11/113,549, Jul. 21, 2009, Office Action.
U.S. Appl. No. 11/152,562, May 13, 2008, Office Action.
U.S. Appl. No. 11/152,562, Feb. 13, 2009, Office Action.
U.S. Appl. No. 11/152,562, Jul. 6, 2009, Office Action.
U.S. Appl. No. 11/152,562, Mar. 31, 2010, Office Action.
U.S. Appl. No. 11/198,811, Aug. 26, 2008, Office Action.
U.S. Appl. No. 11/198,811, Apr. 6, 2009, Office Action.
U.S. Appl. No. 11/198,811, Sep. 22, 2009, Office Action.
U.S. Appl. No. 11/316,775, Apr. 16, 2008, Restriction Requirement.
U.S. Appl. No. 11/316,775, Aug. 6, 2008, Office Action.
U.S. Appl. No. 11/344,793, Jan. 22, 2009, Office Action.

U.S. Appl. No. 11/344,868, Mar. 25, 2009, Office Action.
U.S. Appl. No. 11/344,891, Apr. 29, 2008, Office Action.
U.S. Appl. No. 11/344,891, Dec. 8, 2008, Office Action.
U.S. Appl. No. 11/344,891, Feb. 26, 2009, Office Action.
U.S. Appl. No. 11/344,891, Oct. 7, 2009, Office Action.
U.S. Appl. No. 11/344,891, May 7, 2010, Office Action.
U.S. Appl. No. 11/390,586, Jun. 24, 2009, Office Action.
U.S. Appl. No. 11/396,141, May 22, 2009, Restriction Requirement.
U.S. Appl. No. 11/396,141, Aug. 26, 2009, Office Action.
U.S. Appl. No. 11/396,141, May 4, 2010, Office Action.
U.S. Appl. No. 11/396,731, Feb. 13, 2009, Office Action.
U.S. Appl. No. 11/396,731, May 22, 2009, Office Action.
U.S. Appl. No. 11/406,203, May 14, 2007, Office Action.
U.S. Appl. No. 11/406,203, Jan. 29, 2008, Notice of Allowance.
U.S. Appl. No. 11/406,203, May 23, 2008, Notice of Allowance.
U.S. Appl. No. 11/406,203, Sep. 22, 2008, Notice of Allowance.
U.S. Appl. No. 11/406,203, Mar. 3, 2009, Office Action.
U.S. Appl. No. 11/406,203, Sep. 16, 2009, Office Action.
U.S. Appl. No. 11/406,203, Jun. 18, 2010, Notice of Allowance.
U.S. Appl. No. 11/411,925, Jun. 6, 2007, Office Action.
U.S. Appl. No. 11/411,925, Feb. 5, 2008, Office Action.
U.S. Appl. No. 11/411,925, Jan. 12, 2009, Office Action.
U.S. Appl. No. 11/411,925, Sep. 10, 2009, Office Action.
U.S. Appl. No. 11/427,297, Jan. 30, 2009, Office Action.
U.S. Appl. No. 11/427,297, Sep. 15, 2009, Office Action.
U.S. Appl. No. 11/455,993, Feb. 17, 2009, Office Action.
U.S. Appl. No. 11/455,993, Dec. 16, 2009, Office Action.
U.S. Appl. No. 11/508,656, Dec. 9, 2009, Restriction Requirement.
U.S. Appl. No. 11/508,656, Mar. 25, 2010, Office Action.
U.S. Appl. No. 11/508,662, Dec. 28, 2009, Restriction Requirement.
U.S. Appl. No. 11/508,662, Apr. 14, 2010, Office Action.
U.S. Appl. No. 11/508,715, Jan. 6, 2010, Restriction Requirement.
U.S. Appl. No. 11/508,715, Apr. 26, 2010, Office Action.
U.S. Appl. No. 11/532,325, Feb. 23, 2009, Office Action.
U.S. Appl. No. 11/532,325, Jun. 17, 2009, Office Action.
U.S. Appl. No. 11/532,325, Jan. 5, 2010, Office Action.
U.S. Appl. No. 11/532,576, Mar. 1, 2010, Restriction Requirement.
U.S. Appl. No. 11/532,576, Apr. 23, 2010, Office Action.
U.S. Appl. No. 11/674,930, Jan. 8, 2009, Office Action.
U.S. Appl. No. 11/674,930, Jun. 4, 2009, Office Action.
U.S. Appl. No. 11/674,930, Jan. 8, 2010, Office Action.
U.S. Appl. No. 11/675,462, Dec. 10, 2009, Office Action.
U.S. Appl. No. 11/744,089, Nov. 26, 2008, Office Action.
U.S. Appl. No. 11/744,089, Aug. 14, 2009, Office Action.
U.S. Appl. No. 11/958,295, Aug. 27, 2009, Office Action.
U.S. Appl. No. 11/958,295, May 25, 2010, Office Action.
U.S. Appl. No. 11/959,334, Aug. 19, 2009, Office Action.
U.S. Appl. No. 11/959,334, Jan. 12, 2010, Notice of Allowance.
U.S. Appl. No. 11/959,334, Apr. 14, 2010, Notice of Allowance.
U.S. Appl. No. 12/106,928, Jan. 23, 2009, Office Action.
U.S. Appl. No. 12/106,928, Oct. 5, 2009, Office Action.
U.S. Appl. No. 12/106,928, May 10, 2010, Office Action.
U.S. Appl. No. 12/106,937, Mar. 30, 2009, Office Action.
U.S. Appl. No. 12/106,937, Nov. 18, 2009, Office Action.
U.S. Appl. No. 12/113,851, Apr. 27, 2010, Restriction Requirement.
U.S. Appl. No. 12/402,398, Mar. 9, 2010, Restriction Requirement.
U.S. Appl. No. 12/402,398, May 20, 2010, Office Action.
U.S. Appl. No. 61/015,144, filed Dec. 19, 2007, Mackiewicz et al.
U.S. Appl. No. 61/109,822, filed Oct. 30, 2008, Mehl et al.
U.S. Appl. No. 61/143,748, filed Jan. 9, 2009, Mehl et al.
U.S. Appl. No. 61/143,751, filed Jan. 9, 2009, Voss et al.
U.S. Appl. No. 61/145,468, filed Jan. 16, 2009, Fortson, et al.
U.S. Appl. No. 09/610,128, filed Jul. 5, 2000, Kerievsky.
U.S. Appl. No. 09/866,551, May 25, 2001, Ginn.
U.S. Appl. No. 12/548,274, filed Aug. 26, 2009, Clark.
U.S. Appl. No. 12/724,304, filed Mar. 15, 2010, Fortson.
U.S. Appl. No. 12/848,642, Aug. 2, 2010, Fortson et al.
U.S. Appl. No. 10/006,400, Aug. 2, 2010, Notice of Allowance.
U.S. Appl. No. 10/517,004, Aug. 3, 2010, Notice of Allowance.
U.S. Appl. No. 10/541,083, Aug. 17, 2010, Notice of Allowance.
U.S. Appl. No. 10/638,115, Aug. 13, 2010, Notice of Allowance.
U.S. Appl. No. 10/787,073, Aug. 25, 2010, Notice of Allowance.
U.S. Appl. No. 11/427,309, May 28, 2008, Office Action.
U.S. Appl. No. 11/427,309, Jan. 2, 2009, Office Action.
U.S. Appl. No. 11/427,309, Apr. 20, 2009, Office Action.
U.S. Appl. No. 11/427,309, Nov. 6, 2009, Office Action.
U.S. Appl. No. 11/427,309, Apr. 26, 2010, Office Action.
U.S. Appl. No. 11/675,462, Aug. 31, 2010, Office Action.
U.S. Appl. No. 11/757,108, Nov. 25, 2009, Office Action.
U.S. Appl. No. 11/958,281, Sep. 2, 2010, Office Action.
U.S. Appl. No. 12/403,256, Aug. 19, 2010, Notice of Allowance.
U.S. Appl. No. 11/508,656, Aug. 30, 2010, Office Action.
U.S. Appl. No. 12/897,358, filed Oct. 4, 2010, Carley.
U.S. Appl. No. 12/941,809, filed Nov. 8, 2010, Ginn et al.
U.S. Appl. No. 12/950,628, filed Nov. 19, 2010, Walberg et al.
U.S. Appl. No. 12/955,859, filed Nov. 29, 2010, Ginn.
U.S. Appl. No. 12/961,331, filed Dec. 6, 2010, Voss.
U.S. Appl. No. 12/945,646, filed Nov. 12, 2010, Carley et al.
U.S. Appl. No. 12/966,923, filed Dec. 13, 2010, Cummins et al.
U.S. Appl. No. 12/973,204, filed Dec. 20, 2010, Jabba et al.
U.S. Appl. No. 12/987,792, filed Jan. 10, 2011, Palermo et al.
U.S. Appl. No. 11/427,297, Sep. 15, 2010, Office Action.
U.S. Appl. No. 11/427,309, Nov. 15, 2010, Office Action.
U.S. Appl. No. 11/532,576, Oct. 13, 2010, Notice of Allowance.
U.S. Appl. No. 11/852,190, Nov. 1, 2010, Office Action.
U.S. Appl. No. 11/958,281, Oct. 8, 2010, Office Action.
U.S. Appl. No. 11/959,334, Nov. 10, 2010, Issue Notification.
U.S. Appl. No. 12/106,928, Oct. 25, 2010, Office Action.
U.S. Appl. No. 12/113,851, Dec. 16, 2010, Office Action.
U.S. Appl. No. 12/114,031, Oct. 5, 2010, Restriction Requirement.
U.S. Appl. No. 12/114,031, Nov. 22, 2010, Office Action.
U.S. Appl. No. 12/114,091, Oct. 27, 2010, Restriction Requirement.
U.S. Appl. No. 12/114,091, Dec. 17, 2010, Office Action.
U.S. Appl. No. 12/402,398, Jan. 24, 2011, Office Action.
U.S. Appl. No. 12/403,256, Nov. 23, 2010, Issue Notification.
U.S. Appl. No. 12/403,277, Oct. 12, 2010, Office Action.
U.S. Appl. No. 12/945,646, Jan. 20, 2011, Office Action.
U.S. Appl. No. 10/616,832, Jan. 26, 2011, Issue Notification.
U.S. Appl. No. 11/152,562, Jan. 26, 2011, Issue Notification.
U.S. Appl. No. 13/017,636, filed Jan. 31, 2011, Carley et al.
U.S. Appl. No. 13/026,989, filed Feb. 14, 2011, Cummins.
U.S. Appl. No. 13/030,922, filed Feb. 18, 2011, Cummins.
U.S. Appl. No. 13/039,087, filed Mar. 2, 2011, Palermo et al.
U.S. Appl. No. 10/147,774, Apr. 6, 2011, Issue Notification.
U.S. Appl. No. 10/682,459, Apr. 1, 2011, Notice of Allowance.
U.S. Appl. No. 11/396,731, Mar. 22, 2011, Office Action.
U.S. Appl. No. 11/427,297, Mar. 21, 2011, Office Action.
U.S. Appl. No. 11/852,190, Mar. 2, 2011, Office Action.
U.S. Appl. No. 11/958,281, Mar. 10, 2011, Office Action.
U.S. Appl. No. 12/122,603, Mar. 3, 2011, Office Action.
U.S. Appl. No. 12/403,277, Mar. 31, 2011, Office Action.
U.S. Appl. No. 13/153,594, filed Jun. 6, 2011, Reyes et al.
U.S. Appl. No. 10/667,144, Jun. 6, 2011, Office Action.
U.S. Appl. No. 13/222,899, filed Aug. 31, 2011, Carley et al.
U.S. Appl. No. 12/143,020, Aug. 31, 2011, Office Action.
U.S. Appl. No. 12/897,358, Aug. 22, 2011, Office Action.
U.S. Appl. No. 12/114,091, Jul. 7, 2011, Office Action.
U.S. Appl. No. 12/945,646, Jul. 6, 2011, Office Action.
U.S. Appl. No. 10/682,459, Aug. 10, 2011, Issue Notification.
U.S. Appl. No. 12/113,851, Apr. 27, 2011, Office Action.
U.S. Appl. No. 12/114,031, May 11, 2011, Office Action.
U.S. Appl. No. 12/122,603, Apr. 22, 2011, Office Action.
U.S. Appl. No. 12/143,020, May 11, 2011, Office Action.
U.S. Appl. No. 12/481,377, Apr. 28, 2011, Office Action.
U.S. Appl. No. 13/112,618, filed May 20, 2011, Gianotti et al.
U.S. Appl. No. 13/112,631, filed May 20, 2011, Voss.
U.S. Appl. No. 12/955,859, May 26, 2011, Office Action.
U.S. Appl. No. 12/481,377, Jun. 21, 2011, Office Action.
U.S. Appl. No. 12/135,858, Jul. 13, 2011, Office Action.
U.S. Appl. No. 12/955,859, Jul. 21, 2011, Office Action.
U.S. Appl. No. 11/675,462, Aug. 3, 2011, Office Action.
U.S. Appl. No. 12/114,031, Aug. 2, 2011, Office Action.
U.S. Appl. No. 11/396,731, Sep. 1, 2011, Office Action.
U.S. Appl. No. 12/122,603, Sep. 23, 2011, Office Action.
U.S. Appl. No. 13/026,989, Sep. 16, 2011, Office Action.
U.S. Appl. No. 12/393,877, Sep. 29, 2011, Office Action.

U.S. Appl. No. 10/667,144, Oct. 28, 2011, Notice of Allowance.
U.S. Appl. No. 12/945,646, Oct. 26, 2011, Office Action.
U.S. Appl. No. 12/393,877, Dec. 13, 2011, Office Action.
U.S. Appl. No. 12/941,809, Dec. 13, 2011, Restriction Requirement.
U.S. Appl. No. 12/955,859, Dec. 15, 2011, Office Action.
U.S. Appl. No. 11/675,462, Dec. 22, 2011, Notice of Allowance.
U.S. Appl. No. 12/684,470, Dec. 20, 2011, Restriction Requirement.
U.S. Appl. No. 12/684,569, Dec. 20, 2011, Restriction Requirement.
U.S. Appl. No. 12/481,377, Jan. 3, 2012, Office Action.
U.S. Appl. No. 12/548,274, Dec. 28, 2011, Restriction Requirement.
U.S. Appl. No. 12/684,562, Dec. 28, 2011, Restriction Requirement.
U.S. Appl. No. 12/897,358, Jan. 12, 2012, Notice of Allowance.
U.S. Appl. No. 12/338,977, Jan. 19, 2012, Office Action.
U.S. Appl. No. 12/684,569, Jan. 27, 2012, Office Action.
U.S. Appl. No. 12/684,542, Jan. 30, 2012, Restriction Requirement.
U.S. Appl. No. 12/966,923, Feb. 3, 2012, Notice of Allowance.
U.S. Appl. No. 12/403,256, Dec. 16, 2009, Restriction Requirement.
U.S. Appl. No. 12/403,256, Mar. 30, 2010, Office Action.
U.S. Appl. No. 29/296,370, Aug. 18, 2008, Office Action.
U.S. Appl. No. 29/296,370, Dec. 2, 2008, Notice of Allowance.
U.S. Appl. No. 29/296,370, Apr. 1, 2009, Notice of Allowance.
U.S. Appl. No. 29/296,370, Feb. 10, 2010, Issue Notification.
U.S. Appl. No. 10/147,774, Dec. 2, 2010, Notice of Allowance.
U.S. Appl. No. 10/264,306, Oct. 29, 2010, Notice of Allowance.
U.S. Appl. No. 10/356,214, Sep. 3, 2010, Notice of Allowance.
U.S. Appl. No. 10/435,104, Oct. 5, 2010, Notice of Allowance.
U.S. Appl. No. 10/435,104, Jan. 12, 2011, Issue Notification.
U.S. Appl. No. 10/517,004, Nov. 23, 2010, Issue Notification.
U.S. Appl. No. 10/541,083, Dec. 1, 2010, Issue Notification.
U.S. Appl. No. 10/616,832, Sep. 20, 2010, Notice of Allowance.
U.S. Appl. No. 10/638,115, Dec. 22, 2010, Issue Notification.
U.S. Appl. No. 10/682,459, Oct. 12, 2010, Office Action.
U.S. Appl. No. 10/787,073, Sep. 15, 2010, Issue Notification.
U.S. Appl. No. 11/048,503, Dec. 8, 2010, Issue Notification.
U.S. Appl. No. 11/113,549, Jan. 4, 2011, Office Action.
U.S. Appl. No. 11/152,562, Sep. 16, 2010, Notice of Allowance.
U.S. Appl. No. 11/198,811, Oct. 20, 2010, Issue Notification.
U.S. Appl. No. 11/406,203, Oct. 6, 2010, Issue Notification.
U.S. Appl. No. 12/113,851, Mar. 29, 2012, Office Action.
U.S. Appl. No. 12/114,091, Apr. 5, 2012, Office Action.
U.S. Appl. No. 12/688,065, Mar. 13, 2012, Office Action.
U.S. Appl. No. 12/987,792, Mar. 13, 2012, Office Action.

* cited by examiner

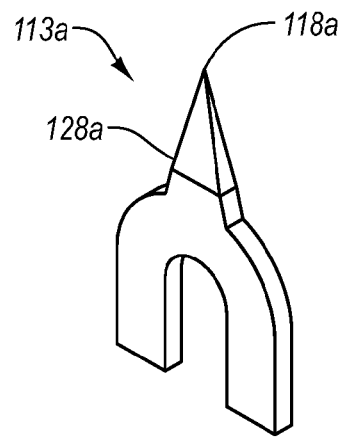 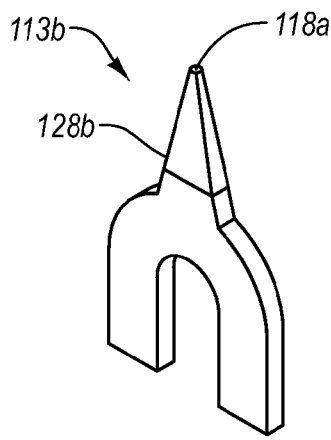 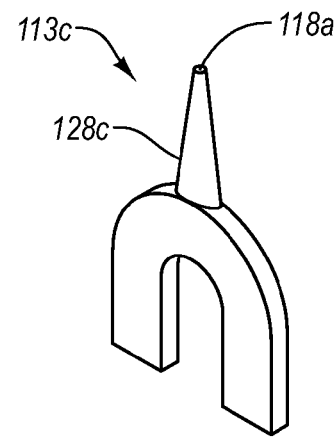
*Fig. 2A*  *Fig. 2B*  *Fig. 2C*
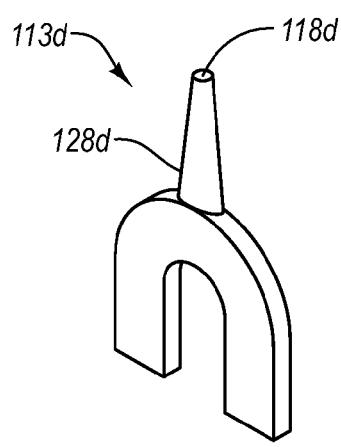 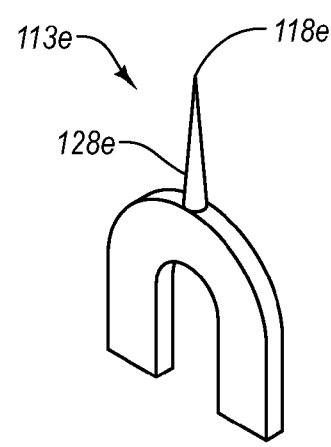 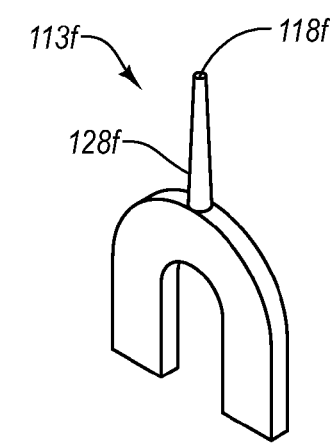
*Fig. 2D*  *Fig. 2E*  *Fig. 2F*

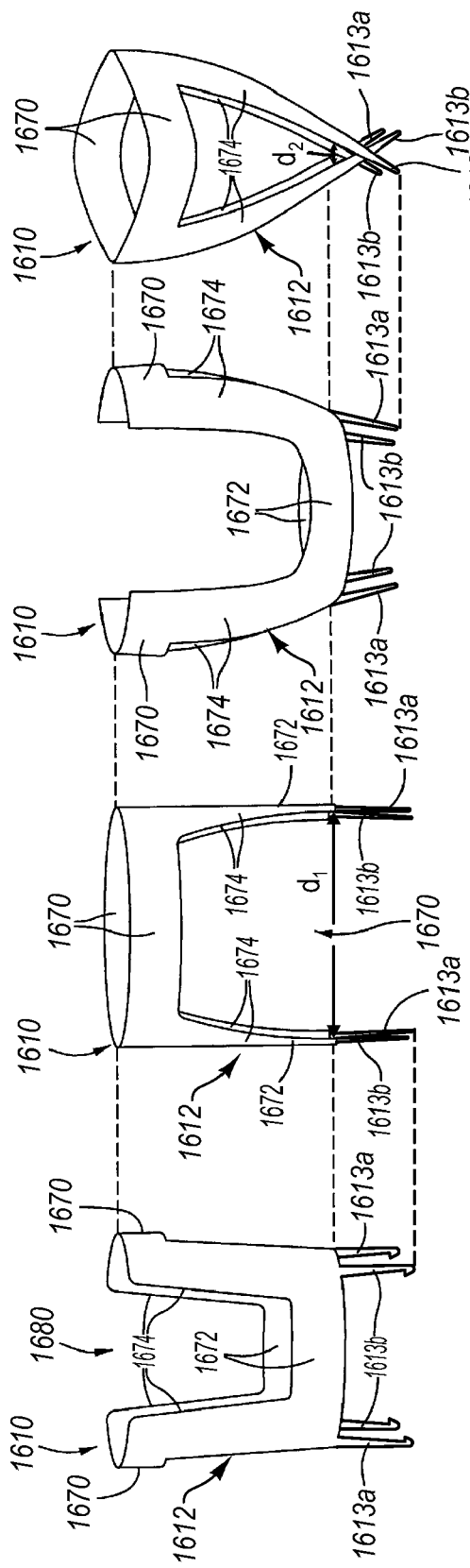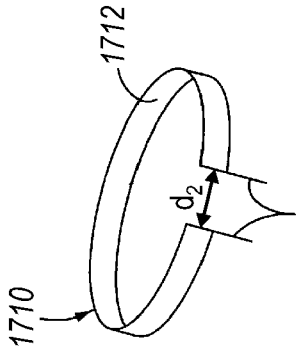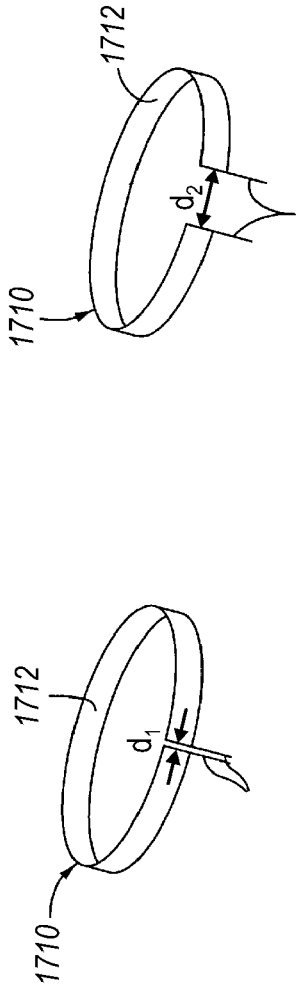

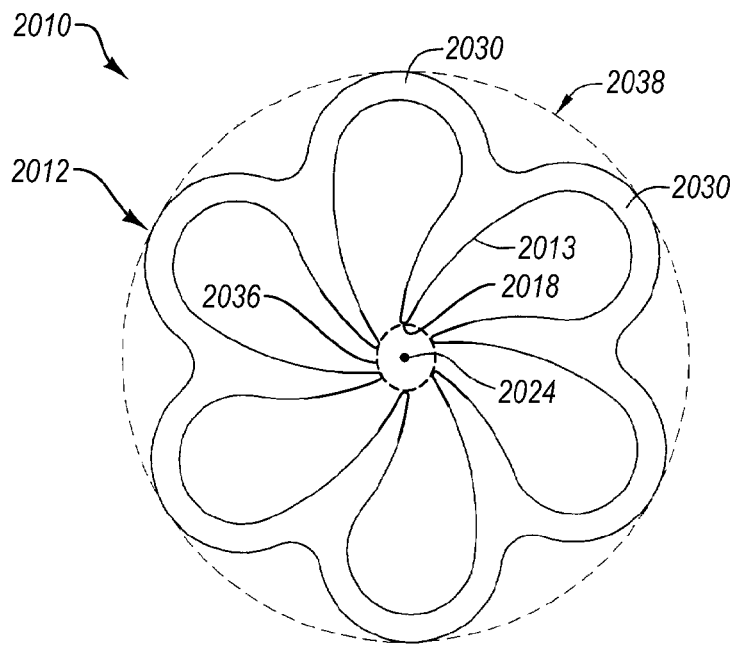
Fig. 21
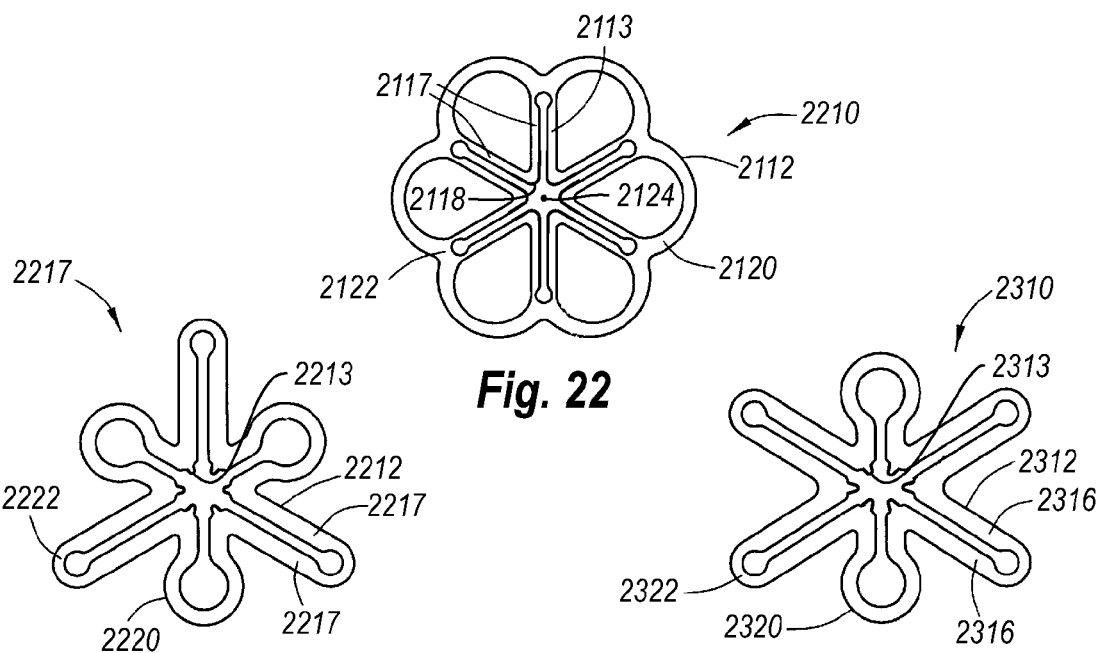
Fig. 22
Fig. 23
Fig. 24

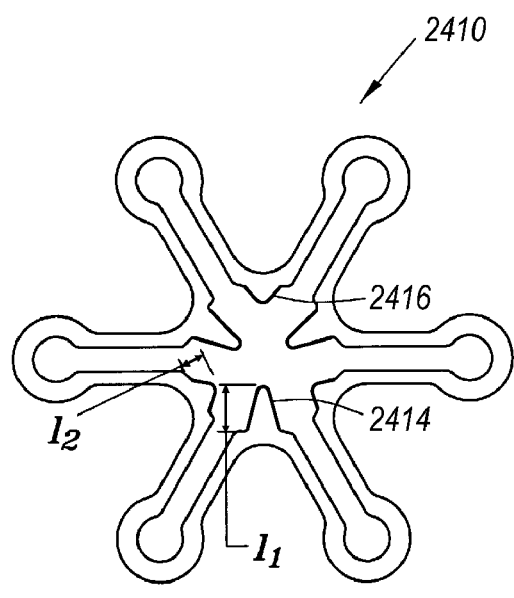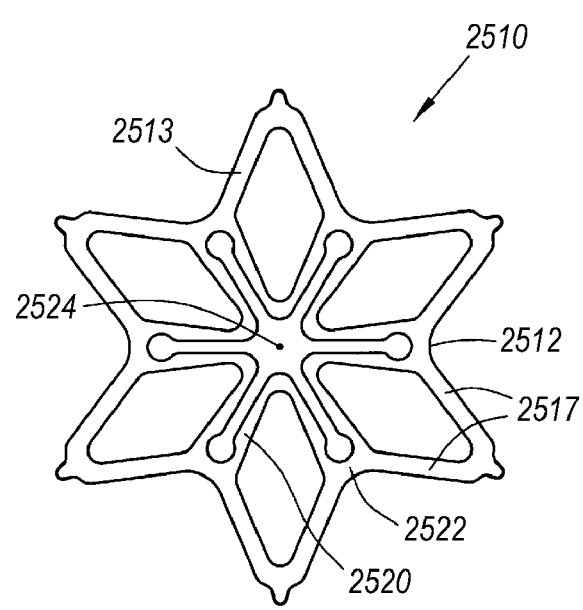
*Fig. 25*  *Fig. 26*

METHODS, DEVICES, AND APPARATUS FOR MANAGING ACCESS THROUGH TISSUE

CROSS-REFERENCE TO RELATED APPLICATIONS

This application incorporates U.S. patent application, Ser. No. 11/427,297, entitled "Clip Applier and Methods of Use", and filed Jun. 28, 2006 in its entirety.

FIELD OF THE INVENTION

The present invention relates generally to medical devices, and more particular to device, apparatus, and methods for managing access through tissue.

BACKGROUND OF THE INVENTION

Catheterization and interventional procedures, such as angioplasty or stenting, generally are performed by inserting a hollow needle through a patient's skin and tissue into the vascular system. A guide wire may be advanced through the needle and into the patients blood vessel accessed by the needle. The needle is then removed, enabling an introducer sheath to be advanced over the guide wire into the vessel, e.g., in conjunction with or subsequent to a dilator.

A catheter or other device may then be advanced through a lumen of the introducer sheath and over the guide wire into a position for performing a medical procedure. Thus, the introducer sheath may facilitate introducing various devices into the vessel, while minimizing trauma to the vessel wall and/or minimizing blood loss during a procedure.

Upon completing the procedure, the devices and introducer sheath would be removed, leaving a puncture site in the vessel wall. Traditionally, external pressure would be applied to the puncture site until clotting and wound sealing occur; however, the patient must remain bedridden for a substantial period of time after clotting to ensure closure of the wound. This procedure, however, may be time consuming and expensive, requiring as much as an hour of a physician's or nurse's time. It is also uncomfortable for the patient, and requires that the patient remain immobilized in the operating room, catheter lab, or holding area. In addition, a risk of hematoma exists from bleeding before hemostasis occurs.

Various apparatus have been suggested for percutaneously sealing a vascular puncture by occluding the puncture site. For example, U.S. Pat. Nos. 5,192,302 and 5,222,974, issued to Kensey et al., describe the use of a biodegradable plug that may be delivered through an introducer sheath into a puncture site. Another technique has been suggested that involves percutaneously suturing the puncture site, such as that disclosed in U.S. Pat. No. 5,304,184, issued to Hathaway et al.

For many patients, the puncture location may be frequently accessed. Frequent access may result in structural changes that may limit access to that point over time. Accordingly, devices, apparatus, and methods for managing access through tissue would be considered useful.

BRIEF SUMMARY

An embodiment device for managing access through tissue is described. The device includes a body movable from a pre-deployed configuration towards a deployed configuration. The device includes a plurality of tissue engaging portions extending from the body. At least a portion of the tissue engaging portions are obtuse. At least two of the tissue engaging portions are separated by a first distance in the deployed configuration and a second distance in the pre-deployed configuration. The first distance is smaller than the second distance.

In some embodiments, the body further defines a plane. The body is disposed about a central axis extending substantially normal to the plane in the deployed configuration. The body is disposed out of the plane in the pre-deployed configuration. The tissue engaging portions are oriented generally towards the central axis in the deployed configuration. The tissue engaging portions are generally parallel to the central axis in the pre-deployed configuration.

At least one tissue engaging portion, in some embodiments, includes an obtuse tip portion. In further embodiments, the tissue engaging portions include an edge that is obtuse.

The body, in some embodiments, is biased towards the deployed configuration for biasing at least one of the tissue engaging portions towards another tissue engaging portion.

In some embodiments, at least a portion of a surface of the device includes a bioactive agent to reduce scar tissue response, structural tissue response, restenosis, thrombosis, or combinations thereof.

The first and second set of tissue engaging portions, in some embodiments, are disposed symmetrically alternatively about a central axis and such that each of the first set of tissue engaging portions is located adjacent to two of the second set of tissue engaging portions. In other embodiments, adjacent tissue engaging portions have a first curved region disposed between them.

In some embodiments, at least one of the tissue engaging portions includes a stop member disposed between a tip of the tissue engaging portion and the respective first curved region. In further embodiments, the stop member includes a blunt base that is substantially wider than the tissue engaging portion and the tissue engaging portions are obtuse from the blunt base to the tip.

In some embodiments, the plurality of tissue engaging elements include a first primary tissue engaging portion having a first length and a second primary tissue engaging portion having a second length. The first and second primary tissue engaging portions are disposed on opposing first curved regions and oriented towards one another in the deployed configuration. The first and second lengths cause the first and second primary tissue engaging portions to at least partially overlap one another in the deployed configuration.

An embodiment of a method for managing access through tissue is described. The method includes deploying a closure element to tissue adjacent a tissue opening to substantially close the opening following a first procedure. The opening in the tissue is selectively opened by advancing a distal end of a medical device through the deployed closure element as a part of or before a second procedure.

Another embodiment of a method for managing access to a body lumen is described. The method includes deploying a closure element to tissue adjacent a tissue opening to substantially close the opening following a first procedure. The closure element includes a body movable from a pre-deployed configuration towards a deployed configuration. The body includes a plurality of tissue engaging portions extending from the body. At least a portion of the tissue engaging portions are obtuse. At least two of the tissue engaging portions are separated by a first distance in the deployed configuration and a second distance in the pre-deployed configuration. The first distance is smaller than the second distance. The method includes locating the deployed closure element. The opening in the tissue is selectively opened by advancing a distal end of a medical device through the deployed closure element as a part of or before a second procedure. The distal end of the medical device is removed through the opening in the tissue and through the closure element thereby redeploying the closure element to the tissue adjacent the opening in the tissue to substantially close the opening.

In some embodiments, the tissue is skin. In other embodiments, the tissue is a wall of a body lumen.

The distal end of the medical device, in some embodiments, is removed through the opening in the tissue and through the closure element thereby redeploying the closure element to the tissue adjacent the opening in the tissue to substantially close the opening. In some embodiments, the medical device includes a cannula or other access device.

In some embodiments, the closure element includes a radiopaque marker. In further embodiments, the method includes locating the deployed closure element using the radiopaque marker. In other embodiments, the method includes locating the deployed closure element using skin marking.

In further embodiments, the closure element includes a body movable from a pre-deployed configuration towards a deployed configuration and a plurality of tissue engaging portions extending from the body. At least a portion of the tissue engaging portions are obtuse. At least two of the tissue engaging portions are separated by a first distance in the deployed configuration and a second distance in the pre-deployed configuration. The first distance is smaller than the second distance.

It is to be understood that both the foregoing general description and the following detailed description are exemplary and are intended to provide further explanation of the invention claimed.

The accompanying Figures, which are incorporated in and constitute part of this specification, are included to illustrate and provide a further understanding of the method and system of the invention. Together with the description, the Figures serve to explain the principles of the invention.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings.

FIGS. 2A-2F illustrate various tissue engaging portions according to the present invention.

FIGS. 17A-17D illustrate another embodiment of a device for managing access through tissue according to the present invention.

FIGS. 18A and 18B illustrate an alternative embodiment of a device for managing access through tissue according to the present invention.

FIG. 21 illustrates a further embodiment of a device for managing access through tissue according to the present invention.

FIG. 22 illustrates a still further embodiment of a device for managing access through tissue according to the present invention.

FIG. 23 illustrates an embodiment of a device for managing access through tissue according to the present invention.

FIG. 24 illustrates another embodiment of a device for managing access through tissue according to the present invention.

FIG. 25 illustrates a further embodiment of a device for managing access through tissue according to the present invention.

FIG. 26 illustrates a still further embodiment of a device for managing access through tissue according to the present invention.

Figure 1A:
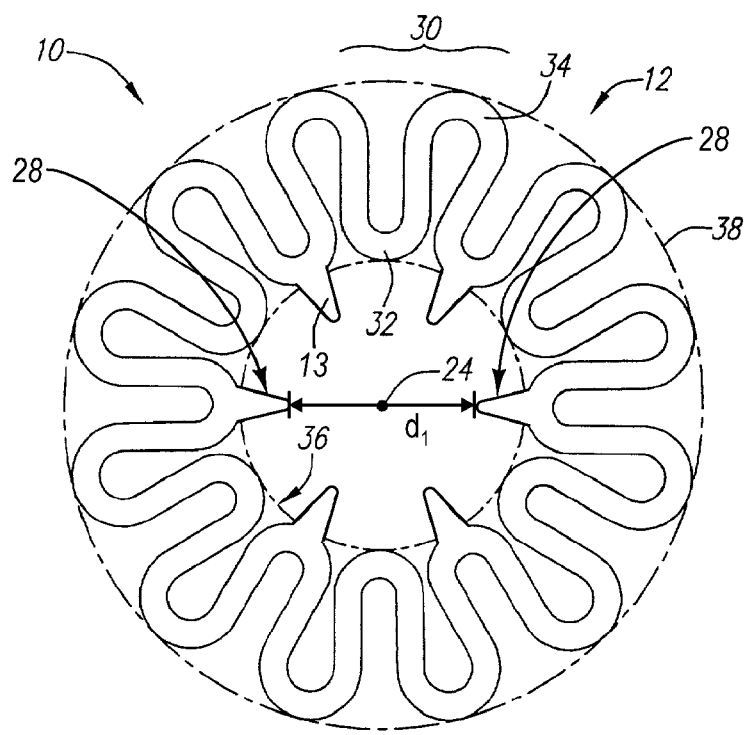
FIG. 1A is a top view of an embodiment of a device for managing access through tissue in a deployed configuration, in accordance with the present invention.

It should be noted that the figures are not drawn to scale and that elements of similar structures or functions are generally represented by like reference numerals for illustrative purposes throughout the figures. It also should be noted that the figures are only intended to facilitate the description of embodiments of the present invention.

DETAILED DESCRIPTION

The embodiments described herein extend to methods, systems, and apparatus for managing access through tissue. Some of the apparatuses of the present invention are configured to deliver a device for managing access through tissue into an opening formed in and/or adjacent to tissue.

One of the challenges of cannulation of vessels may include the need to achieve hemostasis post procedure. For many patients, this access may be frequent, with the potential for complications of vascular access, such as structural changes that may limit access to that point over time. For example, a hemodialysis patient may require vascular access up to six times per week. By having a device that could allow access through tissue and repeatedly provide hemostasis post access, some of these issues may be resolved. Furthermore, the ability to visualize the device with X-ray, may increase access at that site and provide a reduction in complications.

In order to reduce the risk of infection at or near the opening, silver and/or alloys of silver may be used. The silver and/or alloys of silver may be incorporated into at least a portion of the closure element and/or components of the locator and/or carrier assemblies. For example, at least a portion of the closure element and/or components of the locator and/or carrier assemblies may include silver and/or alloys of silver as a component of a coating over and/or a mixture with their respective materials. The use of silver and/or silver alloys may reduce the risk of infection because silver and silver alloys are generally known to possess antimicrobial properties.

These results, whether individually or collectively, can be achieved, according to one embodiment of the present invention, by employing methods, systems, and/or apparatus as shown in the figures and described in detail below.

Turning now to the drawings, FIGS. 1A-1D show a first embodiment of a device 10 for managing access through tissue. The device 10 may be used for closing an incision, puncture, or other passage through tissue. In some embodiments, the device 10 may close communication with a blood vessel or other body lumen (not shown). The device 10 may include a body 12. In the present embodiment, the body 12 may be generally annular in shape and/or may surround a central axis 24. As used herein, an "annular-shaped body" may include any hollow body, e.g., including one or more structures surrounding an opening, whether the body is substantially flat or has a significant thickness or depth. Thus, although an annular-shaped body may be circular, it may include other noncircular shapes as well, such as elliptical or other shapes that are asymmetrical about a central axis. In other embodiments, the body 12 may include other shapes and/or may not have a central axis 24.

The device 10 for managing access through tissue may include a plurality of tissue engaging portions 13 extending from the body 12. The tissue engaging portions 13 may include edges 28 and/or tip portions 18. Portions of the tissue engaging portions 13 may include edges 28 and/or tip portions 18 that are sharp and/or obtuse. In some embodiments, the tissue engaging portions 13 may not have edges such that they are generally rounded.

In the present embodiment, the tip portions 18 may be obtuse to facilitate engaging the tissue. In some embodiments where the tip portion 18 is obtuse, the tip portion 18 may not substantially penetrate the tissue, but rather may engage the tissue to manage access through the tissue. For example, if the device 10 for managing access through tissue were used with an opening in a body lumen, the tip portions 18 may not penetrate through the tissue into the body lumen, but rather may engage the tissue near the opening (although in some embodiments, the tip portions 18 may partially penetrate the tissue). Engaging tissue may include using frictional forces and/or other forces to manipulate the tissue. For example, in an embodiment where the tissue engaging portions 13 have tip portions 18 that are obtuse, the tip portions 18 may engage the tissue such that, as the device 10 moves back toward the deployed configuration, the tissue is pulled closed. In other embodiments, the tip portion 18 may substantially penetrate the tissue. In further embodiments, the tip portions 18 of primary tissue engaging portions (not shown) may substantially penetrate the tissue while the tip portions 18 of secondary tissue engaging portions (not shown) may not substantially penetrate the tissue. Other configurations of the tissue engaging portions 13 and their tip portions 18 may be used.

In the present embodiment, the body 12 may include a plurality of looped or curved elements 30 that may be connected to one another to form the body 12. Each looped element 30 may include an inner or first curved region 32 and an outer or second curved region 34. The first and second curved regions 32, 34 may be out of phase with one another and/or may be connected alternately to one another, thereby defining an endless sinusoidal pattern. Alternatively, other generally zigzag patterns may be provided that repeat periodically, e.g., saw tooth or square tooth patterns (not shown), instead of a sinusoidal pattern, thereby defining inner and outer regions that may alternate about the body 12.

FIG. 1A shows the device 10 in a deployed configuration. In the present embodiment, when the device 10 is in the deployed configuration, the first curved regions 32 may define an inner periphery 36 of the body 12 and the device 10, and the second curved regions 34 may define an outer periphery 38. The deployed configuration, in the present embodiment, may be a substantially planar configuration. In other embodiments, the deployed configuration may be another type of configuration, as shown, for example, by the embodiments shown in FIGS. 17-18.

The plurality of tissue engaging portions 13 may be biased to extend towards one another. In the present embodiment, the tissue engaging portions 13 may be biased generally inwardly into the space bounded by the inner periphery 36. In other configurations, the tissue engaging portions 13 may be biased toward the central axis 24 the central axis 24. In other embodiments, at least two of the tissue engaging portions 13 may be biased to extend towards each other.

In the present embodiment, the tissue engaging portions 13 may be disposed on the first curved regions 32 and/or oriented toward the central axis 24 when the device 10 is in the deployed configuration. The tissue engaging portions 13 may be provided in pairs opposite from one another, as in the present embodiment. The tissue engaging portions 13 may be provided symmetrically with respect to the central axis 24 or may not be provided symmetrically.

Additionally, as shown in FIGS. 1A-1D, the tissue engaging portions 13 may be disposed on alternating first curved regions 32. Thus, at least one period of a zigzag pattern may be disposed between adjacent tissue engaging portions 13, which may enhance flexibility of the device 10, as explained further below.

In the deployed configuration, shown in FIG. 1A, the tissue engaging portions 13 may be separated by a first distance, i.e. $d_1$. In a pre-deployed configuration, shown in FIG. 1B, the tissue engaging portions 13 may be separated by a second distance, i.e. $d_2$. In the present embodiment, the first and second distances $d_1$, $d_2$ may be measured from the tip portion 18 of two tissue engaging portions 13. In other embodiments, the first and second distances $d_1$, $d_2$ may be measured from another portion of the tissue engaging portions 13, for example from the base (not shown) of the tissue engaging portions 13. The first distance $d_1$, in the present embodiment, may be smaller than the second distance $d_2$, such that the distance $d_1$ in the deployed configuration may be smaller than the distance $d_2$ in the pre-deployed configuration.

The distances $d_1$, $d_2$ may vary before deployment, pre-deployment, and/or when providing access through the tissue post deployment. In the present embodiment, before being deployed in tissue, the device 10 for managing access through tissue may be substantially in the pre-deployed configuration such that two tissue engaging portions 13 may be separated by about the second distance $d_2$. When deployed in tissue, the device 10 may be substantially in the deployed configuration such that the two tissue engaging portions 13 may be separated by about the first distance $d_1$. When providing access to the tissue after being deployed in tissue, the device 10 may be moved from substantially the deployed configuration substantially toward and/or to the pre-deployed configuration.

Figure 1B:
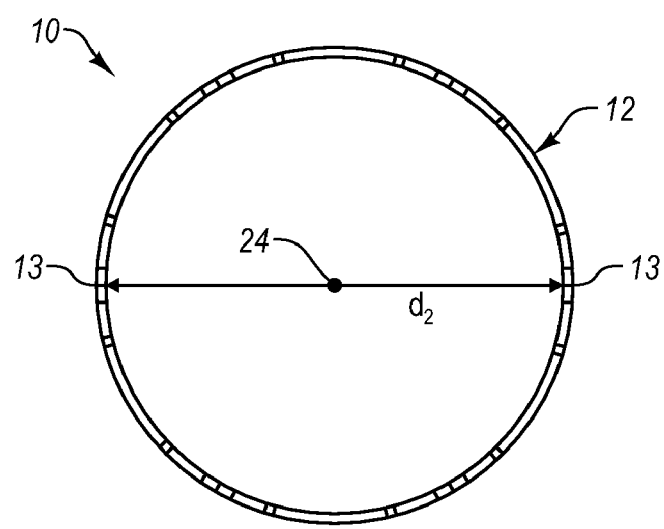
FIG. 1B is a top view of the embodiment shown in FIG. 1A of a device for managing access through tissue in a deployed configuration.

As shown in FIG. 1B, the body 12 and/or the tissue engaging portions 13 may be deflected into the pre-deployed configuration. In the present embodiment, the tissue engaging portions 13 may extend transversely with respect to a plane defined in the deployed configuration, thereby defining the pre-deployed configuration for the device 10. In other embodiments, the body 12 and/or the tissue engaging portions 13 in the pre-deployed configuration may not extend transversely with respect to a plane defined in the deployed configuration. For example, the body 12 and/or the tissue engaging portions 13 in the pre-deployed configuration may remain in a plane defined in the deployed configuration. In another example, the body 12 and/or the tissue engaging portions 13 in the pre-deployed configuration may move out of although not completely transverse to a plane defined in the deployed configuration.

Figure 1C:
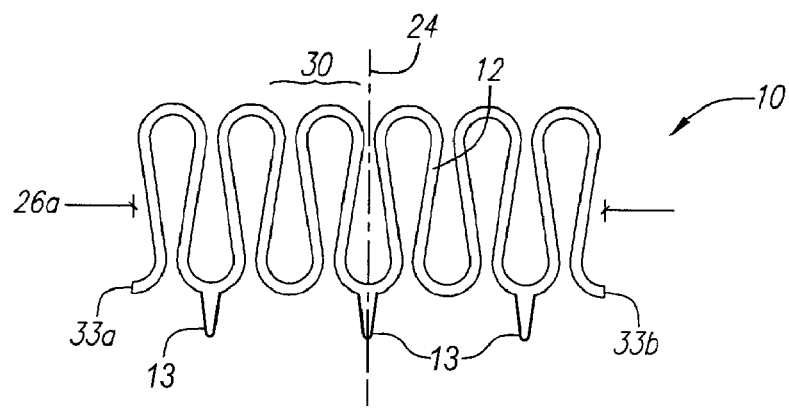
FIGS. 1C and 1D are side views of the embodiment of the device for managing access through tissue of FIG. 1A, with the tissue engaging portions oriented substantially transversely from the planar orientation, in compressed and expanded states, respectively.

In the present embodiment, the tissue engaging portions 13 may be oriented substantially parallel to the central axis 24 in the pre-deployed configuration, as shown in FIG. 1C. In this pre-deployed configuration, the body 12 may have a generally annular shape defining a length, $l_1$, which may extend generally parallel to the central axis 24, and may correspond generally to an amplitude of the zigzag pattern. The body 12 may be sufficiently flexible such that the device 10 may assume a generally circular or elliptical shape, as shown in FIG. 1B, e.g. substantially conforming to an exterior surface of a delivery device (not shown) used to deliver the device 10 for managing access through tissue.

The tissue engaging portions 13 and/or body 12 may be biased to move from the pre-deployed configuration towards the deployed configuration of FIG. 1A. Thus, with the tissue engaging portions 13 in the pre-deployed configuration, the tissue engaging portions 13 may penetrate and/or be engaged with tissue at a puncture site. When the device 10 is released, the tissue engaging portions 13 may attempt to return towards one another (i.e. the distance may decrease from the second distance $d_2$ toward the first distance $d_1$) as the device 10 moves towards the deployed configuration, thereby drawing the engaged tissue together and substantially closing and/or sealing the puncture site, as explained further below.

The looped elements 30 may distribute stresses in the device 10 for managing access through tissue as it is moved between the deployed and pre-deployed configurations, thereby generally minimizing localized stresses that may otherwise plastically deform, break, and/or otherwise damage the device 10 during delivery. In addition, when the device 10 is in the pre-deployed configuration, the looped elements 30 may be movable between a compressed state, such as that shown in FIG. 1C, and an expanded state, such as that shown in FIG. 1D (where opposite ends 33a, 33b are connected to one another). The body 12 may be biased towards the expanded state, but may be compressed to the compressed state, e.g., by constraining the device 10. Alternatively, only a portion of the body 12 may be biased towards the expanded state. For example, in the present embodiment, the first curved regions 32 and/or the looped elements 30 may be biased towards the compressed state. Furthermore, the looped elements 30 may reduce the force required to be exerted on the device 10 to transition the device 10 from the deployed configuration to the pre-deployed configuration before loading onto a delivery device (not shown).

With the device 10 in the pre-deployed configuration, the looped elements 30 may be circumferentially and/or radially compressed to the compressed state until the device 10 defines a first diameter or circumference 26a, such as that shown in FIG. 1C. The device 10 may be constrained in the compressed state, e.g., by loading the device 10 onto a carrier assembly of a delivery device (not shown), as described further below. When released from the constraint, e.g., when deployed from the carrier assembly, the device 10 may automatically expand towards the expanded state, such as that shown in FIG. 1D, thereby defining a second diameter or circumference 26b. Thus, the looped elements 30 may facilitate reducing the profile of the device 10 during delivery, e.g., to facilitate introducing the device 10 through a smaller puncture or passage. Once the device 10 is deployed entirely from the delivery device, the looped elements 30 may resiliently expand as the device 10 returns towards the deployed configuration, as explained further below.

FIGS. 2A-2F illustrate various tissue engaging portions 113. FIG. 2A illustrates a tissue engaging portion 113a with a sharp tip portion 118a and sharp edges 128a. FIG. 2B illustrates a tissue engaging portion 113b with an obtuse tip portion 118b and sharp edges 128b. In the embodiments of FIGS. 2A and 2B, the tissue engaging portions 113 are shown with four sharp edges 128a, 128b. In other embodiments, the tissue engaging portions 113 may include more or fewer sharp edges 128.

FIG. 2C illustrates a tissue engaging portion 113c with a smaller obtuse tip portion 118c and obtuse edges 128c. FIG. 2D illustrates a tissue engaging portion 113d with a larger obtuse tip portion 118d and obtuse edges 128d. FIG. 2E illustrates a thin tissue engaging portion 113e with a sharp tip portion 118e and obtuse edges 128e. FIG. 2F illustrates a thin tissue engaging portion 113f with an obtuse tip portion 118f and obtuse edges 128f.

Tissue engaging portions 113 with sharp tip portions 118, i.e. tissue engaging portions 113a, 113e, may more easily penetrate tissue compared to a tissue engaging portion 113 with an obtuse tip portion 118, i.e. tissue engaging portions 113b, 113c, 113d, 113f. Tissue engaging portions 113 with sharp edges 128, i.e. tissue engaging portions 113a, 113b, may more easily cut and/or damage the surrounding tissue if the device 10 moves after the device 10 is deployed compared to a tissue engaging portion 113 with an obtuse edge 128, i.e. tissue engaging portions 113c, 113d, 113e, 113f. For example, if a deployed device 10 that includes a tissue engaging portion 113 with at least one sharp edge 128 is moved while deployed, the device 10 may more easily cut and/or damage the surrounding tissue. While a deployed device 10 that includes a tissue engaging portion 128 with all obtuse edges 128 is moved while deployed, the device 10 may less easily cut and/or damage the surrounding tissue.

Figure 3A:
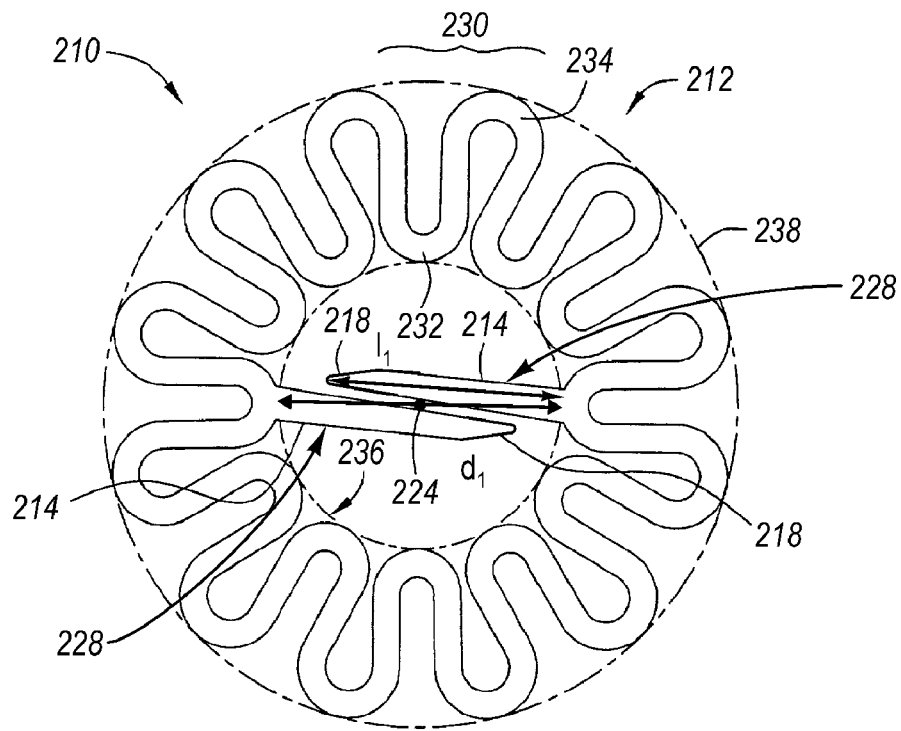
FIGS. 3A-3B illustrate another embodiment of a device for managing access through tissue including a pair of primary tissue engaging portions according to the present invention.
Figure 3B:
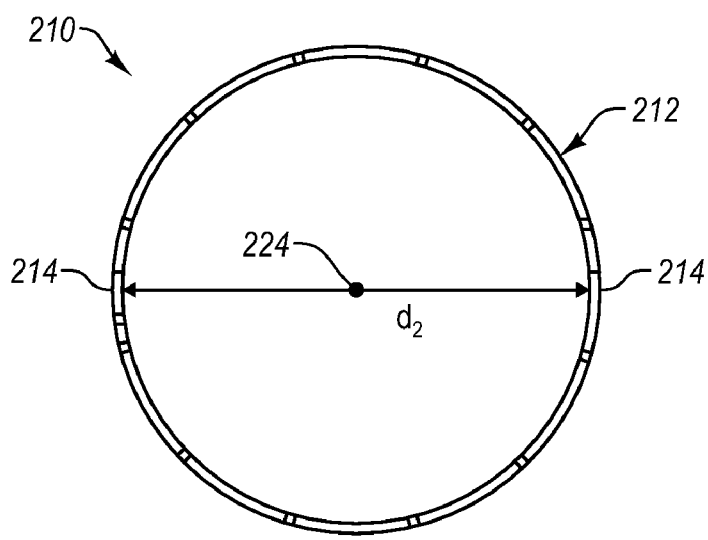

FIGS. 3A-3B illustrate another embodiment of a device 210 for managing access through tissue according to the present invention. The device 210 may include a generally annular shaped body 212 defining a plane and disposed about a central axis 224 extending through the plane. The body 212 may include a plurality of looped elements 230 that are connected to one another to form the body 212, similar to the embodiment of FIGS. 1A-1D. Each looped element 230 may include an inner or first curved region 232 and an outer or second curved region 234, in a deployed configuration (shown in FIG. 3A). Similar to the embodiment of FIGS. 1A-1D, the first and second curved regions 232, 234 may form an endless sinusoidal pattern or other generally zigzag pattern. When the device 210 is in the deployed configuration, which may be substantially planar in the present embodiment, as shown in FIG. 3A, the first curved regions 232 may define an inner periphery 236, and the second curved regions 234 may define an outer periphery 238.

Unlike the previous embodiment, the device 210 for managing access through tissue of the present embodiment may include only one pair of primary tissue engaging portions 214. The primary tissue engaging portions 214 may have a length $l_1$, although alternatively each of the primary tissue engaging portions 214 may have a different length than one another.

Although the length, $l_1$, is illustrated as extending from a curved region 232, 234, beyond the central axis 224, it may be possible for the length, $l_1$, to be less than this distance, such as a length defined from a curved region 232, 234 to the central axis 224 or a length defined from a curved region 232, 234 toward, but not passing the central axis 224. The primary tissue engaging portions 214 may be disposed in one or more opposing pairs, e.g., on opposing first curved regions 232, and may be oriented towards and/or across the central axis 224 in the planar configuration. In the deployed configuration, the primary tissue engaging portions 214 may be sufficiently long such that the primary tissue engaging portions 214 at least partially overlap one another, i.e., extend across the central axis 224 towards an opposing tissue engaging portion 214.

Therefore, the tip portions 218 of the primary tissue engaging portions 214 may extend past the central axis 224 and/or the primary tissue engaging portions 214 in each pair may lie substantially parallel to each other when the device 210 for managing access through tissue is in the deployed configuration. Each of the primary tissue engaging portions 214 may include a variety of tip portions 218 and/or edges 228 as described in connection with FIGS. 2A-2F.

In the deployed configuration, shown in FIG. 3A, the primary tissue engaging portions 214 may be separated by a first distance, i.e. $d_1$. In a pre-deployed configuration, shown in FIG. 3B, the primary tissue engaging portions 214 may be separated by a second distance, i.e. $d_2$. In the present embodiment, the first and second distances $d_1$, $d_2$ may be measured from the base (not shown) of the two primary tissue engaging portions 214. In other embodiments, the first and second distances $d_1$, $d_2$ may be measured from another portion of the primary tissue engaging portions 214, for example from tip portion 218 of the primary tissue engaging portions 214. The first distance $d_1$, in the present embodiment, may be smaller than the second distance $d_2$, such that the distance $d_1$ in the deployed configuration may be smaller than the distance $d_2$ in the pre-deployed configuration.

The distances $d_1$, $d_2$ may vary before deployment, pre-deployment, and/or when providing access through the tissue post deployment. In the present embodiment, before being deployed in tissue, the device 210 for managing access through tissue may be substantially in the pre-deployed configuration such that the two primary tissue engaging portions 214 may be separated by about the second distance $d_2$. When deployed in tissue, the device 210 may be substantially in the deployed configuration such that the two primary tissue engaging portions 214 may be separated by about the first distance $d_1$. When providing access to the tissue after being deployed in tissue, the device 210 may be moved from the substantially deployed configuration substantially toward and/or to the pre-deployed configuration.

As shown in FIG. 3B, the body 212 and/or the primary tissue engaging portions 214 may be deflected into the pre-deployed configuration, similar to the embodiment of FIGS. 1A-1D. In the present embodiment, the primary tissue engaging portions 214 may extend transversely with respect to a plane defined in the deployed configuration, thereby defining the pre-deployed configuration for the device 210.

The primary tissue engaging portions 214 and/or body 212 may be biased to move from the pre-deployed configuration towards the deployed configuration of FIG. 3A. Thus, with the primary tissue engaging portions 214 in the pre-deployed configuration, the primary tissue engaging portions 214 may penetrate and/or be engaged with tissue at a puncture site. When the device 210 is released, the primary tissue engaging portions 214 may attempt to return towards one another (i.e. the distance may decrease from the second distance $d_2$ toward the first distance $d_1$) as the device 210 moves towards the deployed configuration, thereby drawing the engaged tissue together and substantially closing and/or sealing the puncture site, as explained further below.

The primary tissue engaging portions 214 of the present embodiment may include the tip portions 218 and/or edges 228 described in connection with FIGS. 2A-2F. For example, the tip portions 218 and/or the edges 228 of the primary tissue engaging portions 214, in the present embodiment, may be obtuse.

FIGS. 4A-4G illustrate a further embodiment of a device 310 for managing access through tissue according the present invention. In the present embodiment, the device 310 may include a body 312. The body may include looped elements 330 and tissue engaging portions 13, similar to the previous embodiments. The reference numbers for elements of the device 310 are consistent with like elements used for the devices 10, 110.

The device 310 for managing access through tissue of the present embodiment may include a plurality of primary tissue engaging portions 314 and a plurality of secondary tissue engaging portions 316. Each of the primary and secondary tissue engaging portions 314, 316 may include a variety of tip portions 318 and/or edges 328 as described in connection with FIGS. 2A-2F.

The primary tissue engaging portions 314 may be similar to the primary tissue engaging portions 214 of the previous embodiment. However, each of the secondary tissue engaging portions 316 may be disposed on a first or inner curved region 332, e.g., such that one or more secondary tissue engaging portions 316 may be provided between opposing pairs of primary tissue engaging portions 314. Each of the secondary tissue engaging portions 316 may have a length $l_2$ that is substantially less than the length, $l_1$, of the primary tissue engaging portions 314.

Although the length, $l_1$, is illustrated as extending from a curved region 332, 334, beyond the central axis 324, it may be possible for the length, $l_1$, to be less than this distance, such as a length defined from a curved region 332, 334 to the central axis 324 or a length defined from a curved region 332, 334 toward, but not passing the central axis 324. A secondary tissue engaging portion 316 may be disposed on either side of each primary tissue engaging portion 314, in the present embodiment. For example, the device 310 for managing access through tissue may include first and second primary tissue engaging portions 314. Each of the first and second primary tissue engaging portions 314 may include a secondary tissue engaging portion 316 on either side of it. Thus, the device 310 may include a total of two primary tissue engaging portions 314 and four secondary tissue engaging portions 316. The secondary tissue engaging portions 316, in the present embodiment, may be disposed substantially symmetrically about the central axis 324. The tissue engaging portions 314, 316 may be provided on every other first curved regions 332. For example, a first curved region 332 having neither a primary tissue engaging portion 314 nor a secondary tissue engaging portion 316 may separate each adjacent tissue engaging portion, e.g., between two adjacent secondary tissue engaging portions 316, or between a secondary tissue engaging portion 316 and a primary tissue engaging portion 314. The primary and secondary tissue engaging portions 314, 316 may also include other orientations and arrangements.

Figure 4A:
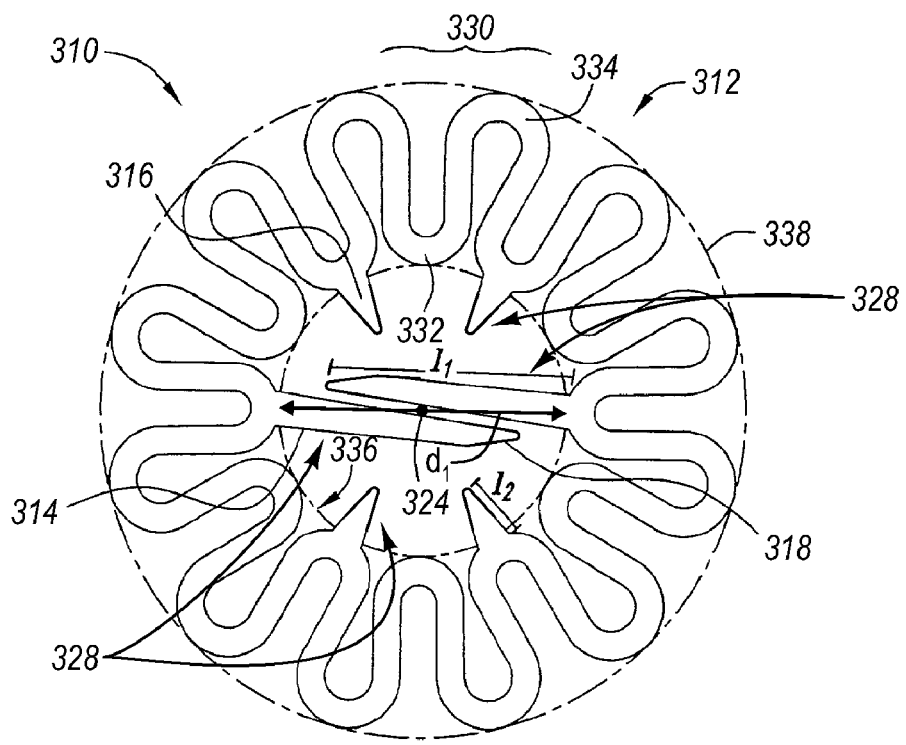
FIGS. 4A-4G illustrate further embodiments of a device for managing access through tissue including primary tissue engaging portions and secondary tissue engaging portions according the present invention.
Figure 4B:
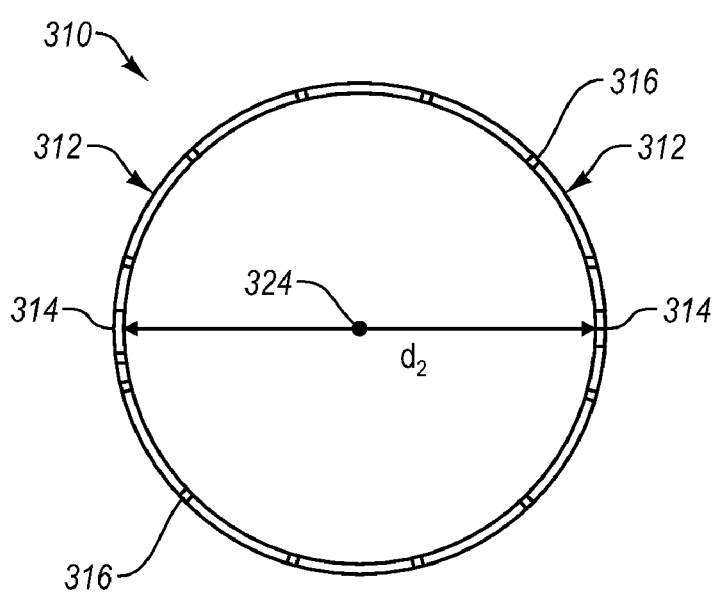
Figure 4C:
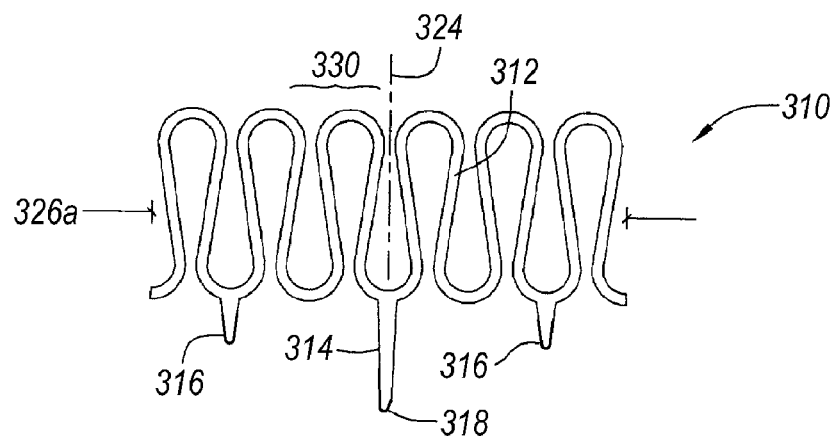
Figure 4D:
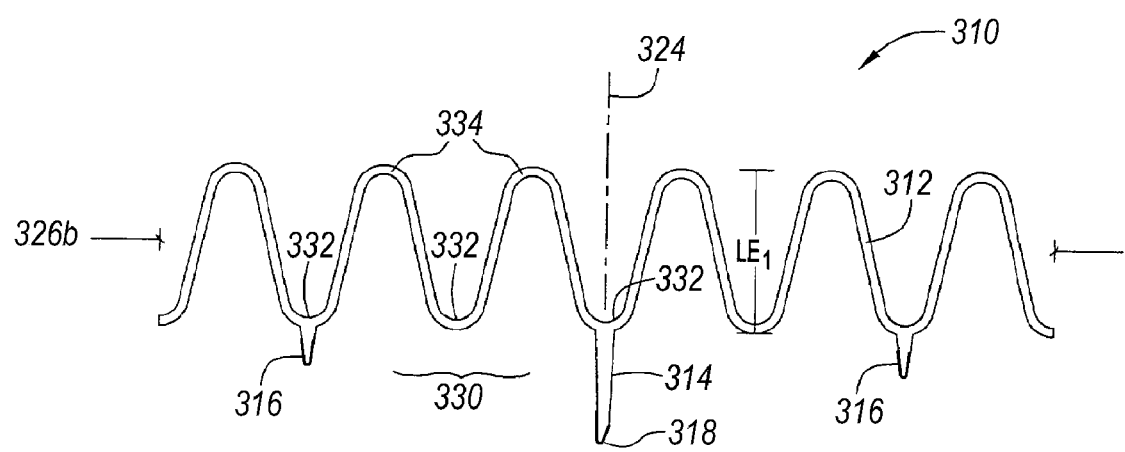

The device 310 may be moved from the deployed configuration of FIG. 4A to the pre-deployed configuration, as shown in FIGS. 4B-4D. In the present embodiment, the body 312 and/or the tissue engaging portions 314, 316 may be deflected into the pre-deployed configuration such that they extend transversely with respect to the plane defined in FIG. 4A. The primary tissue engaging portions 314 and/or secondary tissue engaging portions 316 may be oriented substantially parallel to the central axis 324 in the pre-deployed configuration, as shown in FIGS. 4B-4D. In the pre-deployed configuration of the present embodiment, the body 312 may have a generally annular shape defining a length, $LE_1$, which extends generally parallel to the central axis 24, and corresponds generally to an amplitude of the sinusoidal pattern. The body 312 may be sufficiently flexible such that the device 310 may assume a generally circular or elliptical shape, as shown in FIG. 4B, e.g., conforming to an exterior surface of a delivery device (not shown).

The tissue engaging portions 314, 316 may be biased towards one another and/or towards the central axis 324, i.e., due to the bias of the device 310 towards the deployed configuration of FIG. 4A. With the device 310 in the pre-deployed configuration, the device 310 may be delivered such that the primary tissue engaging portions 314, in the present embodiment, may entirely penetrate the wall of a blood vessel or other body lumen, while the secondary tissue engaging portions 316 may only partially penetrate and/or engage the wall due to their relative lengths. In other embodiments, the primary tissue engaging portions 314 may partially penetrate the wall of a blood vessel or other body lumen, while the secondary tissue engaging portions 316 may partially penetrate and/or engage the wall due to their relative lengths. In further embodiments, the primary tissue engaging portions 314 may engage the wall of a blood vessel or other body lumen, while the secondary tissue engaging portions 316 may penetrate and/or engage the wall due to their relative lengths.

In the deployed configuration, shown in FIG. 4A, the primary tissue engaging portions 314 may be separated by a first distance, i.e. $d_1$. In a pre-deployed configuration, shown in FIG. 4B, the primary tissue engaging portions 314 may be separated by a second distance, i.e. $d_2$. In the present embodiment, the first and second distances $d_1$, $d_2$ may be measured from the base (not shown) of the two primary tissue engaging portions 314. In other embodiments, the first and second distances $d_1$, $d_2$ may be measured from another portion of the primary tissue engaging portions 314, for example from the tip portions 318 of the primary tissue engaging portions 314. The first distance $d_1$, in the present embodiment, may be smaller than the second distance $d_2$, such that the distance $d_1$ in the deployed configuration may be smaller than the distance $d_2$ in the pre-deployed configuration.

The distances $d_1$, $d_2$ may vary before deployment, pre-deployment, and/or when providing access through the tissue post deployment. In the present embodiment, before being deployed in tissue, the device 310 for managing access through tissue may be substantially in the pre-deployed configuration such that the two primary tissue engaging portions 314 may be separated by about the second distance $d_2$. When deployed in tissue, the device 310 may be substantially in the deployed configuration such that the two primary tissue engaging portions 314 may be separated by about the first distance $d_1$. When providing access to the tissue after being deployed in tissue, the device 310 may be moved from the substantially deployed configuration substantially toward and/or to the pre-deployed configuration.

Figure 1D:
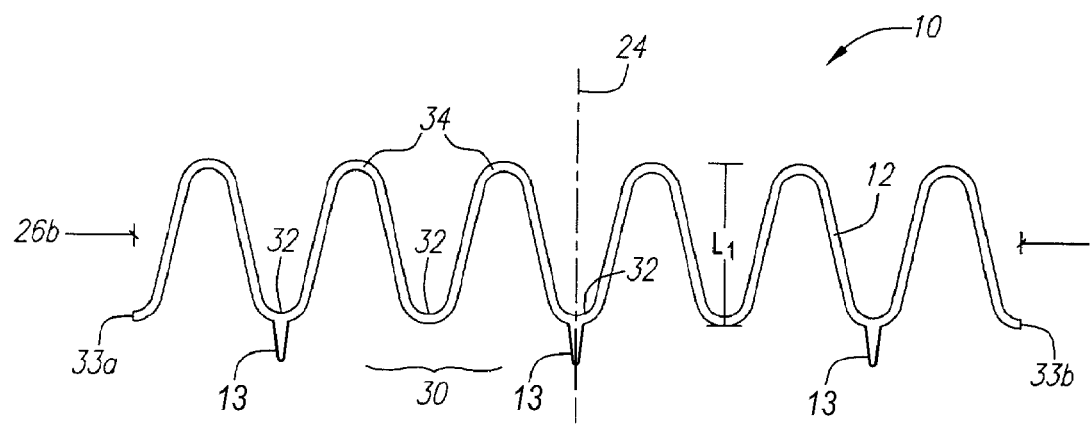

The looped elements 330 may be expandable between a compressed state, as shown in FIG. 4C, and an expanded state, as shown in FIG. 4D, similar to the embodiment of FIGS. 1C and 1D. The looped elements 330 may be biased to the expanded state, but may be resiliently compressed to the compressed state, e.g., by constraining the device 310.

Figure 4E:
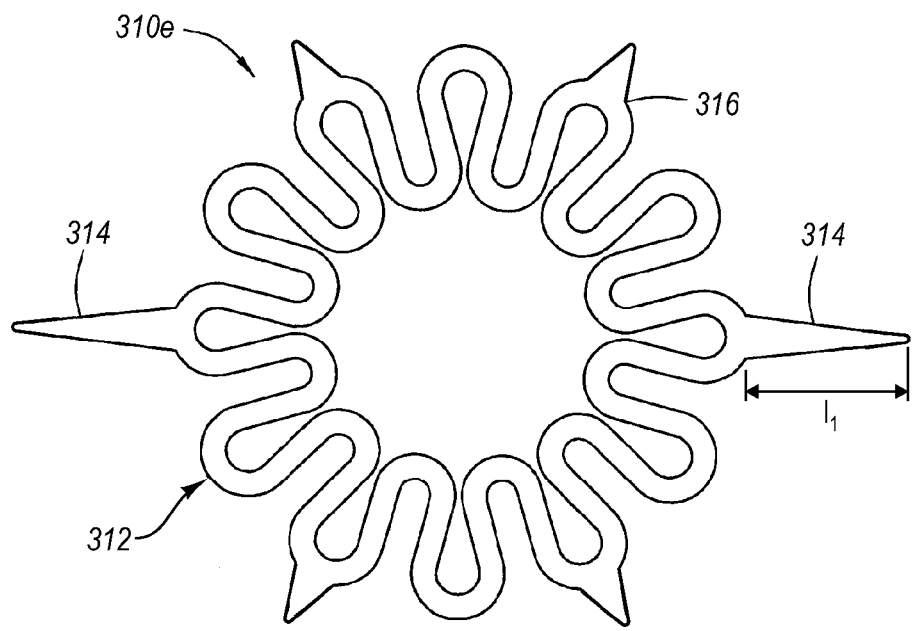

FIG. 4E illustrates a manufacturing precursor 310e of a device 10 for managing access through tissue according to the present invention. The described embodiments of a device 10 for managing access through tissue may be manufactured using various manufacturing processes. One exemplary process will be described below. In the present embodiment, a precursor 310e may be formed from a sheet of material. In some embodiments, the sheet of material may be a superelastic alloy, such as a nickel-titanium alloy (NITINOL®). The property of superelasticity and of certain alloys that possess that property is disclosed in U.S. Pat. No. 4,665,906 which is incorporated by reference herein. This forming can be done by removing portions of the material by cutting, chemical etching, laser cutting, photochemical etching, stamping, electrical discharge machining, or other forming processes to produce a precursor such as that shown in FIG. 4E which may include radially outward extending tissue engaging portions 314, 316. Although the length, $l_1$, is illustrated as extending from a curved region (not shown), beyond the central axis (not shown), it may be possible for the length, $l_1$, to be less than this distance, such as a length defined from a curved region to the central axis or a length defined from a curved region toward, but not passing the central axis.

The precursor 310e can then be polished using one or more polishing processes such as electropolishing, tumbling, sand blasting, sanding, or other polishing processes. In some embodiments, polishing may be done as a final step after the device 10 for managing access through tissue is formed. Forming of a precursor 310e in this manner may not require working to tolerances as close as those which would be required if the device 10 was to be manufactured in its final configuration shown in FIG. 4A because the radially outwardly extending tissue engaging portions 314, 316 of the precursor 310e shown in FIG. 4E are easily accessible by the forming tool whereas attempting to directly form the device 10 with radially inwardly extending tissue engaging portions 13 which are closely spaced typically requires difficult high precision metal cutting. Thus, manufacture of a precursor 310e that is then reconfigured to a final shape may permit the achievement of closer spacing between the elements of the final device 310 than would otherwise be generally achievable with conventional methods.

The tissue engaging portions 13 may be formed or given a shape, e.g., pointed, rounded, edged, chamfered, etc., while the device 10 is in the precursor state. For example, the tip portions 18 and/or edges 28 (shown in FIG. 1A) may be formed such that they are sharp, obtuse and/or otherwise formed. The precursor 310e may be inverted to reconfigure it into the shape of the device 10. When the precursor 310e is formed from a sheet of nickel-titanium alloy, the inverted precursor 310e may then heat set, e.g., by heating to a temperature of about 510° C., and then quenched to cool to about room temperature. The device 10 may now be in the austenitic state.

Heat setting and quenching are typically essential to successful practice of the invention with superelastic alloys. As explained in more detail in U.S. Pat. No. 4,665,906, a superelastic alloy such as nickel-titanium generally exists in two states, the austenitic state and the martensitic state. Such alloys will initially be in the austenitic state, e.g., when the precursor 310e is formed. However, when the precursor 310e is inverted to take the shape of the final device 310, the stress experienced by the alloy during the inversion will cause the alloy to be partially or wholly converted to the martensitic state. Such a martensitic state is commonly referred to as stress-induced martensite. Such martensite structure generally has the property of superelasticity and the inverted precursor would typically revert to its original shape if not held in the inverted configuration.

Since, if the inverted precursor 310e were left in the martensitic state, it would want to elastically revert to its original uninverted state, it must be converted back to austenite. Thus, heating and quenching are generally required to convert the inverted precursor 310e from the martensitic state to the austenitic state such that the device 310 for managing access through tissue is stable in its deployed configuration as shown in FIG. 4A and will retain that configuration.

The times and temperatures for heat setting of superelastic alloys of various compositions may be determined from existing literature or may be determined empirically without any difficulty. The devices 10 are typically small in size and the heating and quenching may be done with any conventional heating and quenching equipment. For example, once inverted, the inverted precursor 310e may be held in that configuration and placed in a fixture that will hold it in the inverted configuration during heat setting.

Figure 9:
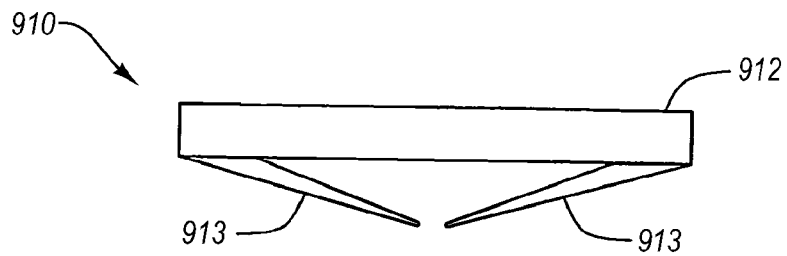
FIG. 9 illustrates an embodiment of an inverted manufacturing precursor of devices for managing access to tissue including tissue engaging portions extending at an acute angle to the plane defined by the body according to the present invention.

When devices 10 are manufactured according to this process, the space between the tissue engaging portions 13 may actually be substantially eliminated, i.e., after inverting the precursor, the tissue engaging portions 13 may be in contact with each other, in either a side-by-side or an over-and-under relationship. The number, length, and spacing of the tissue engaging portions may be varied according to the desires of the manufacturer. Furthermore, while use of a planar precursor is a convenience in manufacturing, planar precursors may not be required. For example, the precursor 310e could be bent along a diameter or major or minor axis of the precursor 310e and could be heat set in such a bent configuration. Alternatively, the device 910, in generally planar embodiments, may have the tissue engaging portions 913 extending at an acute angle to the plane defined by the body 912 as shown in FIG. 9. Furthermore, manufacturing from a sheet of material may be convenient, but other manufacturing techniques, including joining of components, such as the tissue engaging portions 13 to the body 12, may be accomplished by welding, brazing, or other known methods of joining materials. In such cases, one or more of such components may be circular in cross-section or tubular in configuration. Examples of devices 10 for managing access through tissue that may be joined are shown in FIGS. 14-16B.

Still further, the device 310 for managing access through tissue need not be fabricated from a single material, e.g., the tissue engaging portions 13 may be manufactured from a different material than the body 312. In such cases, a portion of the device 310 such as the tissue engaging portions 314, 316 may be bioabsorbable if the final device 310 is capable of elastic recovery after being deformed. Forming a precursor 310e may permit the production of devices 10 with tissue engaging portions 13 that are longer by about 30 to 40% or more than those that could be made with prior direct cutting methods, because there is typically no limit on the length of the tissue engaging portion 13 that may be formed on the precursor 310e. Thus, after the precursor 310e is inverted, the tissue engaging portions 314, 316 may overlap the body 312.

In some embodiments, the devices 10 may include a bioactive agent. The bioactive agent may be associated with a base coat and/or top coat and/or incorporated or otherwise applied to a supporting structure of the device 10.

The bioactive agent may have any therapeutic effect. Examples of suitable therapeutic properties may include anti-proliferative, anti-inflammatory, antissue engaging portionoplastic, antiplatelet, anti-coagulant, anti-fibrin, antithrombonic, antimitotic, antibiotic, antiallergic, antioxidant properties, and/or other therapeutic properties.

Examples of suitable bioactive agents include synthetic inorganic and organic compounds, proteins and peptides, polysaccharides and other sugars, lipids, DNA and RNA nucleic acid sequences, antisense oligonucleotides, antibodies, receptor ligands, enzymes, adhesion peptides, blood clot agents, including streptokinase and tissue plasminogen activator, antigens, hormones, growth factors, ribozymes, retroviral vectors, anti-proliferative agents including rapamycin (sirolimus), 40-O-(2-hydroxyethyl)rapamycin (everolimus), 40-O-(3-hydroxypropyl)rapamycin, 40-O-(2-hydroxyethoxy)ethylrapamycin, 40-O-tetrazolylrapamycin (zotarolimus, ABT-578), paclitaxel, docetaxel, methotrexate, azathioprine, vincristissue engaging portion, vinblastissue engaging portion, fluorouracil, doxorubicin hydrochloride, mitomycin, antiplatelet compounds, anticoagulants, antifibrin, antithrombins including sodium heparin, low molecular weight heparins, heparinoids, hirudin, argatroban, forskolin, vapiprost, prostacyclin, prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors including Angiomax ä, calcium channel blockers including nifedipine, colchicine, fibroblast growth factor (FGF) antagonists, fish oil (omega 3-fatty acid), histamine antagonists, lovastatin, monoclonal antibodies, nitroprusside, phosphodiesterase inhibitors, prostaglandin inhibitors, suramin, serotonin blockers, steroids, thioprotease inhibitors, triazolopyrimidine, nitric oxide or nitric oxide donors, super oxide dismutases, super oxide dismutase mimetic, estradiol, anticancer agents, dietary supplements including vitamins, anti-inflammatory agents including aspirin, tacrolimus, dexamethasone and clobetasol, cytostatic substances including angiopeptin, angiotensin converting enzyme inhibitors including captopril, cilazapril or lisinopril, antiallergic agents such as permirolast potassium, alpha-interferon, bioactive RGD, and genetically engineered epithelial cells. Other bioactive agents, which are currently available or that may be developed in the future for use with medical devices, may likewise be used and all are within the scope of this invention.

For example, a bioactive agent may be used to reduce scar tissue response when the device 10 is deployed in tissue. Reducing scar tissue response, structural tissue response, restenosis, and/or thrombosis may facilitate access to the tissue after the device 10 is deployed. For example, if a device did not use a beneficial agent to reduce scar tissue response, structural tissue response, restenosis, and/or thrombosis after deployment, these and/or other tissue responses may hinder future access to the tissue.

After a device 10 for managing access through tissue is deployed, it may be desirable to provide access through the deployed device 10. Locating a deployed device 10 may be necessary to provide future access through the device 10. Radiopaque markers, skin marking and/or other location techniques may be used to facilitate location of a deployed device 10.

Any of the devices of the present invention may include one or more radiopaque markers or other markers visible using external imaging, such as fluoroscopy. For example, using the device 310 of FIGS. 4A-4D as an example, the entire device 310 may be coated with radiopaque material, which may be a high density material such as gold, platinum, platinum/iridium, and the like.

Alternatively, a device 10 may be partially coated with radiopaque material by using masking techniques. For example, the entire device 10 may first be coated with radiopaque material. The device 10 may then be masked at locations where the radiopaque coating is desired. For example, the looped elements 30 of the device 10 may be left unmasked during this process if it is desired to leave the looped elements 30 uncoated by radiopaque material. This may be desirable, e.g., to prevent radiopaque material from adversely affecting the flexibility of the body 12. The device 10 may then be treated to remove the radiopaque material from the unmasked areas, in this example, the body 12. The masking may then be removed using conventional processes, leaving the rest of the device 10 coated with radiopaque material.

In some embodiments, silver and/or alloys of silver may be incorporated into at least a portion of the device 10. For example, silver and/or alloys of silver may be included as a component of a mixture that may be incorporated into the material of the device 10. In embodiments where the device 10 is formed from a sheet of material, the sheet of material may include silver and/or alloys of silver as a component of the material. In embodiments where the device 10 is formed from a wire as described in U.S. Pat. No. 6,719,777, the wire may include silver and/or alloys of silver as a component of the wire.

In other embodiments, at least a portion of the device 10 may include a coating that includes silver and/or alloys of silver as a component of the coating. For example, a coating of silver and/or alloys of silver may be applied to a portion of the surface of the device 10. Coatings may be applied using various coating methods. Coating methods may include physical vapor deposition, chemical vapor deposition, ion beam assisted deposition, electroplating and/or other coating methods. Physical vapor deposition may include sputter deposition and/or other physical vapor deposition methods.

Figure 4F:
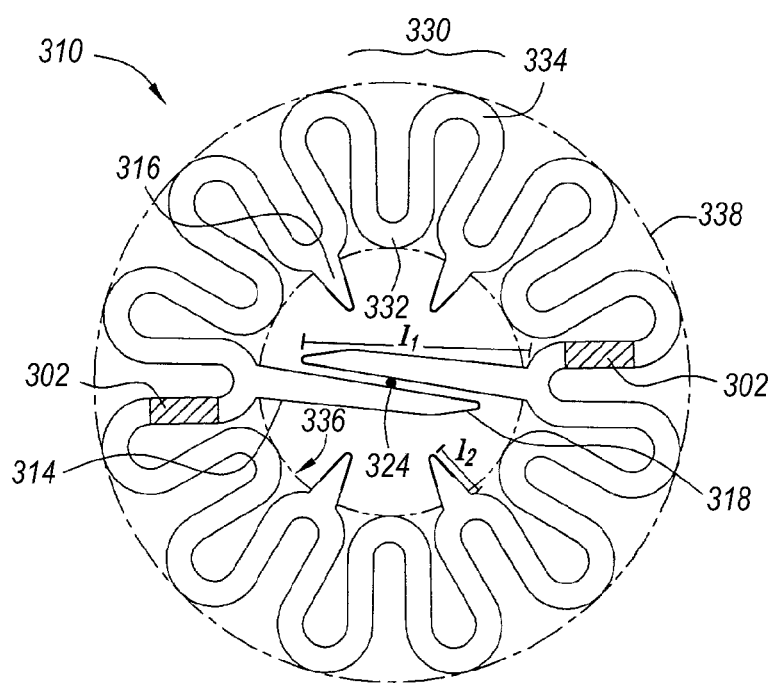

Turning to FIG. 4F, one or more discrete markers 302 may be provided at predetermined locations on the device 310. For example, high density or radiopaque material 302 may be crimped or otherwise secured onto opposing portions of the body 312. In another embodiment, shown in FIG. 4G, a plurality of pockets 304 may be provided on the looped elements 330 into which high density plugs (not shown) may be bonded or otherwise secured. These various radiopaque markers may also be incorporated in any of the embodiments described herein.

Figure 4G:
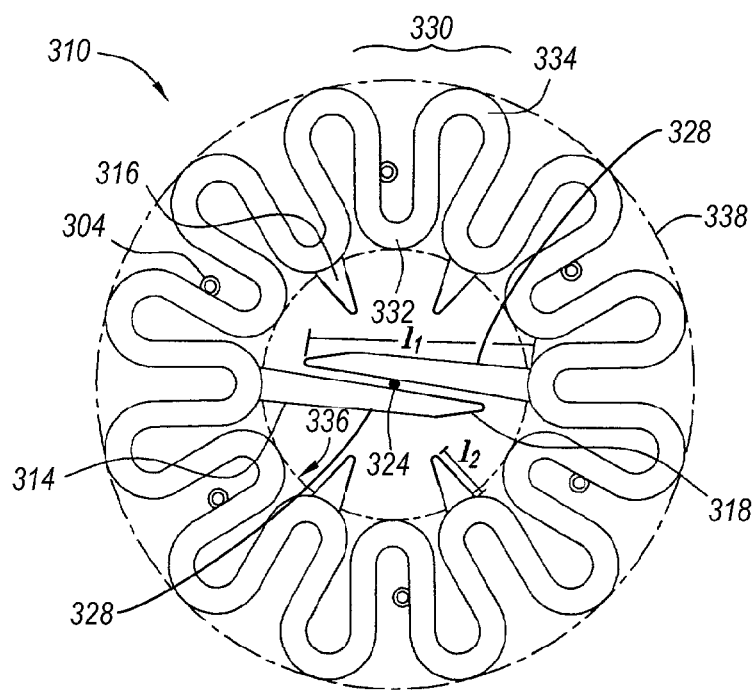

As described in connection with FIG. 4A, each of the secondary tissue engaging portions 316 may have a length $l_2$ that is substantially less than the length, $l_1$, of the primary tissue engaging portions 314. Although the length, $l_1$, in FIG. 4G is illustrated as extending from a curved region 332, 334, beyond the central axis 324, it may be possible for the length, $l_1$, to be less than this distance, such as a length defined from a curved region 332, 334 to the central axis 324 or a length defined from a curved region 332, 334 toward, but not passing the central axis 324, as described in connection with FIGS. 4A and 4E.

Figure 5:
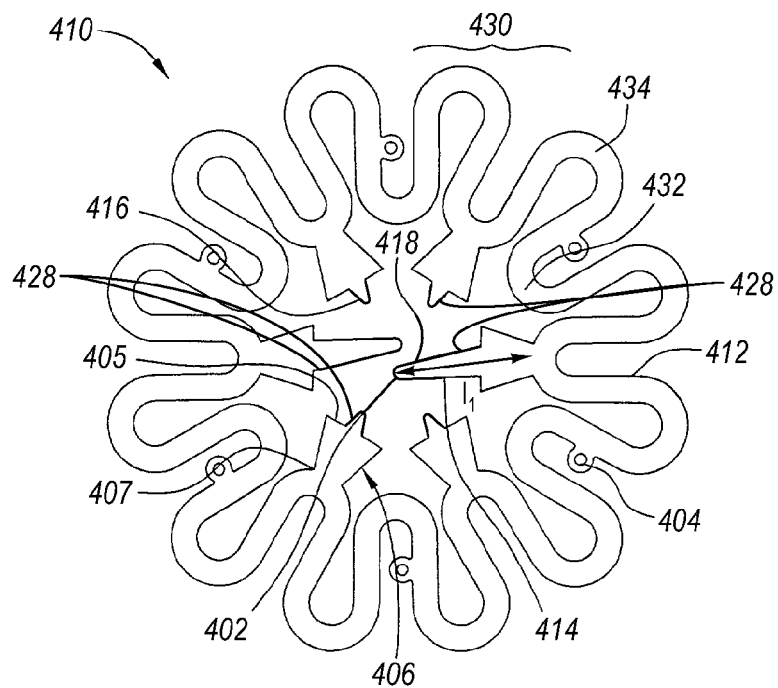
FIG. 5 illustrates another embodiment of a device for managing access through tissue including stop members according to the present invention.

Turning to FIG. 5, another embodiment of a device 410 is shown that, similar to devices 10, 110, 210, 310, may include a plurality of looped elements 430 that interconnect to form a body 412. Each looped element 430 may have a first or inner curved region 432 and a second or outer curved region 434. Primary tissue engaging portions 414 may be disposed on opposing first curved regions 432. Secondary tissue engaging portions 416 may be provided on first curved regions 432 on either side of each primary tissue engaging portion 414. In addition, a first curved region 432 without a tissue engaging portion 414, 416 may separate adjacent tissue engaging portions. Although the length, $l_1$, is illustrated as extending from a curved region 432, 434, beyond the central axis 424, it may be possible for the length, $l_1$, to be less than this distance, such as a length defined from a curved region 432, 434 to the central axis 424 or a length defined from a curved region 432, 434 toward, but not passing the central axis 424.

The device 410 may also include stop members 406 on one or more of the tissue engaging portions 414, 416, e.g., adjacent the respective first curved region 432. Each stop member 406 may be blunt-shaped. For example, the stop members 406 may be shaped generally triangularly with an apex 407 of the stop member 406 extending from the first curved region 432, and the tissue engaging portion 414, 416 extending from a wide or blunt base 407 of the stop member 406. During use, the blunt bases 407 may limit penetration of the respective tissue engaging portions 414, 416 into tissue by reducing an effective length of the respective tissue engaging portion 414, 416. For example, when the tissue engaging portions 414, 416 are driven into tissue, the tissue engaging portions 414, 416 may penetrate the tissue until the blunt bases 407 contact the tissue, whereupon the tissue engaging portions 414, 416 may be prevented from penetrating further into the tissue. Stop members 406 may be used in other embodiments to decrease the amount of the tissue engaging portion 414, 416 that penetrates and/or engages surrounding tissue.

Each of the tissue engaging portions 414, 416 may include a variety of tip portions 418 and/or edges 428 as described in connection with FIGS. 2A-2F. In addition, the device 410 for managing access through tissue may include a deployed configuration (shown, for example, in FIG. 5) and a pre-deployed configuration (not shown). In the deployed configuration, shown in FIG. 5, the primary tissue engaging portions 414 may be separated by a first distance, i.e. $d_1$. In a pre-deployed configuration (not shown), the primary tissue engaging portions 414 may be separated by a second distance, i.e. $d_2$.

The tissue engaging portions 414, 416 and/or body 412 may be biased to move from the pre-deployed configuration towards the deployed configuration of FIG. 5. Thus, with the tissue engaging portions 414, 416 in the pre-deployed configuration, the tissue engaging portions 414, 416 may penetrate and/or be engaged with tissue at a puncture site. When the device 410 is released, the tissue engaging portions 414, 416 may attempt to return towards one another (i.e. the distance may decrease from the second distance $d_2$ toward the first distance $d_1$) as the device 410 moves towards the deployed configuration, thereby drawing the engaged tissue together and substantially closing and/or sealing the puncture site.

FIGS. 6A-6E show a further embodiment of a device 510 for managing access through tissue according to the present invention. The device 510 may include a peripheral body 512 and a plurality of tissue engaging portions 513. Each tissue engaging portion 513 may include a pair of legs 517 terminating in a tip portion 518. In the present embodiment, the tissue engaging portions 513 may be configured for penetrating and/or otherwise engaging tissue. Each of the tissue engaging portions 513 may include a variety of tip portions 518 and/or edges 528 as described in connection with FIGS. 2A-2F. The tissue engaging portions 513 may be disposed substantially symmetrically about a central axis 524. The body 512 may include a plurality of expandable elements 520 that may be connected by hinged regions 522. The hinged regions 522 may also connect adjacent tissue engaging portions 513.

Figure 6A:
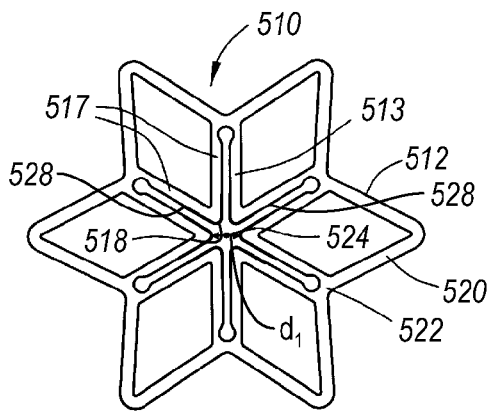
FIGS. 6A-6E illustrate a further embodiment of a device for managing access through tissue according to the present invention.

FIG. 6A shows the device 510 in a deployed configuration. In the present embodiment, the deployed configuration may be a substantially planar configuration. In other embodiments, the deployed configuration may be another type of configuration, as shown, for example, by the embodiments shown in FIGS. 17-18.

Figure 6B:
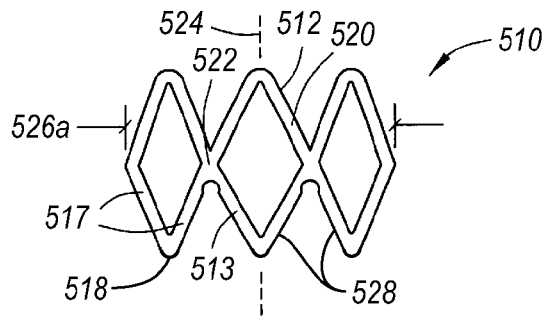
Figure 6C:
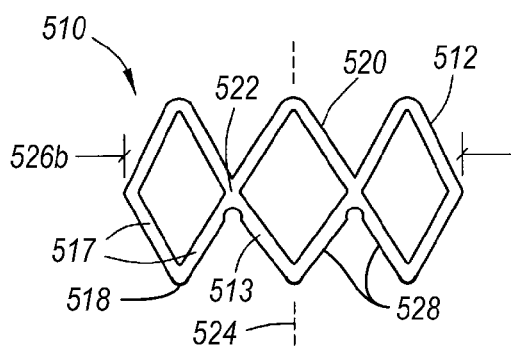
Figure 6D:
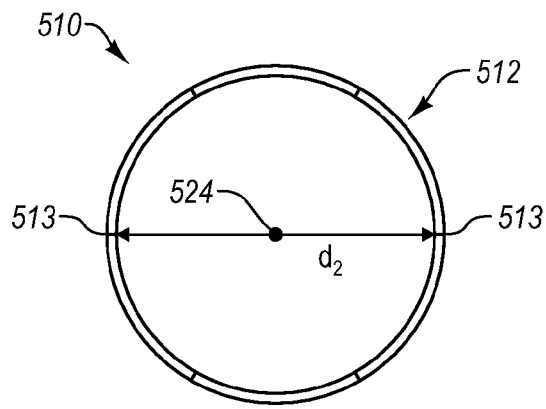

As shown in FIGS. 6B and 6D, the tissue engaging portions 513 may be deflected such that they extend from the body 512 substantially transversely with respect the plane defined by the device 510. In the embodiments of FIG. 6B-6D, the tissue engaging portions 513 may be oriented substantially parallel to the axis 524 to define a pre-deployed configuration.

In the deployed configuration, shown in FIG. 6A, the tissue engaging portions 516 may be separated by a first distance, i.e. $d_1$. In the pre-deployed configuration, shown in FIG. 6D, the tissue engaging portions 516 may be separated by a second distance, i.e. $d_2$. In the present embodiment, the first and second distances $d_1$, $d_2$ may be measured from a tip portion 518 of the tissue engaging portions 513. In other embodiments, the first and second distances $d_1$, $d_2$ may be measured from another portion of the tissue engaging portions 513, for example from the base (not shown) of the tissue engaging portions 513. The first distance $d_1$, in the present embodiment, may be smaller than the second distance $d_2$, such that the distance $d_1$ in the deployed configuration may be smaller than the distance $d_2$ in the pre-deployed configuration.

Figure 6E:
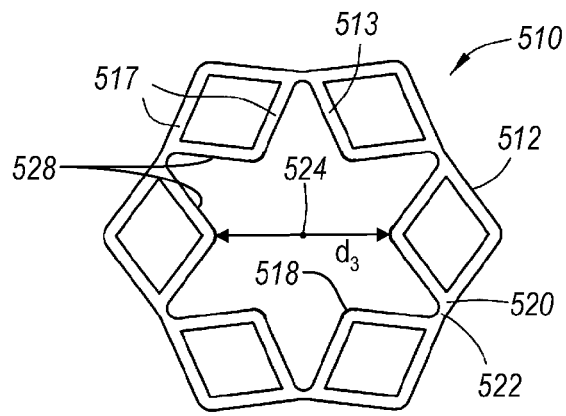

The tissue engaging portions 513 may define an angle with respect to the axis 524, as shown in FIG. 6E, to define an access configuration. The device 510 may move substantially toward an access configuration after the device 510 has been deployed while providing access through the device 510. In the present embodiment, while in the access configuration, the body 512 may have a generally annular shape, e.g., a hexagonal shape as shown in FIG. 6E. In other embodiments, the device 510 may take other shapes in the access configuration.

In the access configuration, the tissue engaging portions 516 may be separated by a third distance, i.e. $d_3$. In the present embodiment, the first and third distances $d_1$, $d_3$ may be measured from a tip portion 518 of the tissue engaging portions 513. In other embodiments, the first and third distances $d_1$, $d_3$ may be measured from another portion of the tissue engaging portions 513, for example from the base (not shown) of the tissue engaging portions 513. The first distance $d_1$, in the present embodiment, may be smaller than the third distance $d_3$, such that the distance $d_1$ in the deployed configuration may be smaller than the distance $d_3$ in the access configuration.

The access configuration shown in FIG. 6E may provide an example of an access configuration and/or pre-deployed that may be within the same plane as the deployed configuration. In other embodiments, an access configuration and/or pre-deployed may extend away from a plane in the deployed configuration, though the pre-deployed configuration may not be transverse to the plane. In further embodiments, an access configuration and/or pre-deployed configuration may both extend away from a plane in the deployed configuration, though the access and/or pre-deployed configuration may not be transverse to the plane, and away from a central axis 524.

The body 512 may be sufficiently flexible such that the device 510 may assume a generally circular or elliptical shape, as shown in FIG. 6D, e.g., conforming to an exterior surface of a delivery device (not shown) used to deliver the device 510.

The tissue engaging portions 513 may be biased from the pre-deployed and/or access configurations towards one another, i.e., towards the deployed configuration of FIG. 6A. Thus, with the tissue engaging portions 513 in the pre-deployed and/or access configurations, the tip portions 518 may be engaged with tissue, e.g. adjacent to a puncture site. When the device 510 is released, the tissue engaging portions 513 may attempt to return to the deployed configuration, thereby drawing the engaged tissue together and substantially closing and/or sealing the puncture site.

In addition, the expandable elements 520 may be expandable from a compressed state, shown in FIG. 6B, to an expanded state, shown in FIG. 6C. The expandable elements 520 may be biased to the expanded state, but may be compressed to the compressed state, e.g., by constraining the device 510. In some embodiments, the device 510 may be formed with the expandable elements 520 in the expanded state. With the device 10 in its pre-deployed configuration, the expandable elements 520 may be circumferentially and/or radially compressed to the compressed state such that the device 510 defines a first diameter 526a, shown in FIG. 6B. The device 510 may be constrained at the first diameter 526a, e.g., by loading the device 510 into a delivery device (not shown), as described further below. When released from the constraint, e.g., when deployed from the delivery device, the device 510 may automatically expand to a second diameter 526b, shown in FIG. 6C. Thus, the expandable elements 520 may reduce the profile of the device 510 for managing access through tissue during delivery, e.g., to facilitate introduction of the device 510 through a smaller puncture or other passage.

Figure 7A:
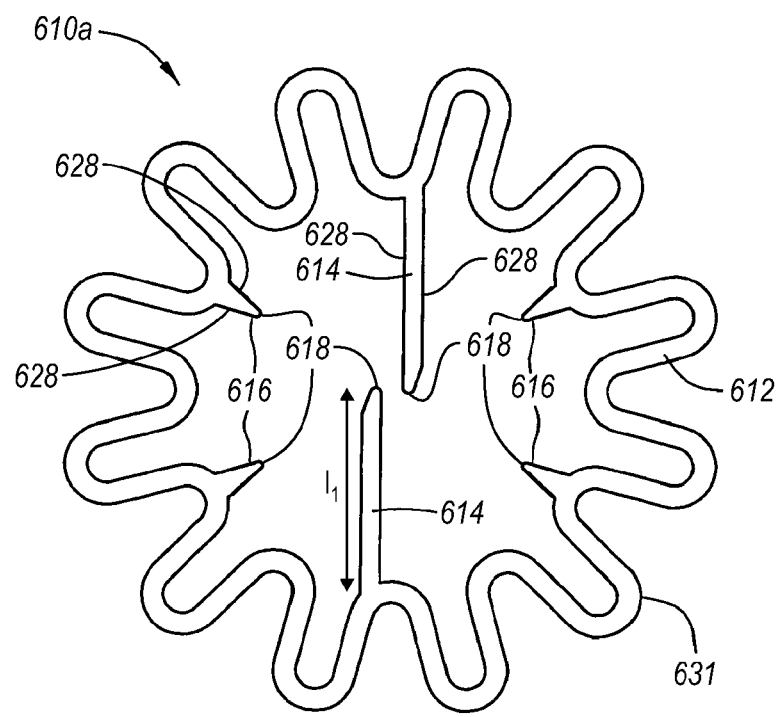
FIGS. 7A-7B illustrate an embodiment of a manufacturing precursor of devices for managing access to tissue according to the present invention.

Using the manufacturing processes generally described in connection with FIG. 4E, FIGS. 7-13 generally illustrate alternative embodiments of manufacturing precursors of devices for managing access to tissue according to the present invention. In the embodiment illustrated in FIGS. 7A and 7B, the precursor 610 may be manufactured in an expanded oversize configuration, as shown in FIG. 7A, to provide space for removing material from a sheet of material, i.e. a superelastic alloy such as nickel-titanium, by conventional methods such as cutting, chemical etching, photochemical etching, stamping, electric discharge machining, laser cutting or the like.

Figure 7B:
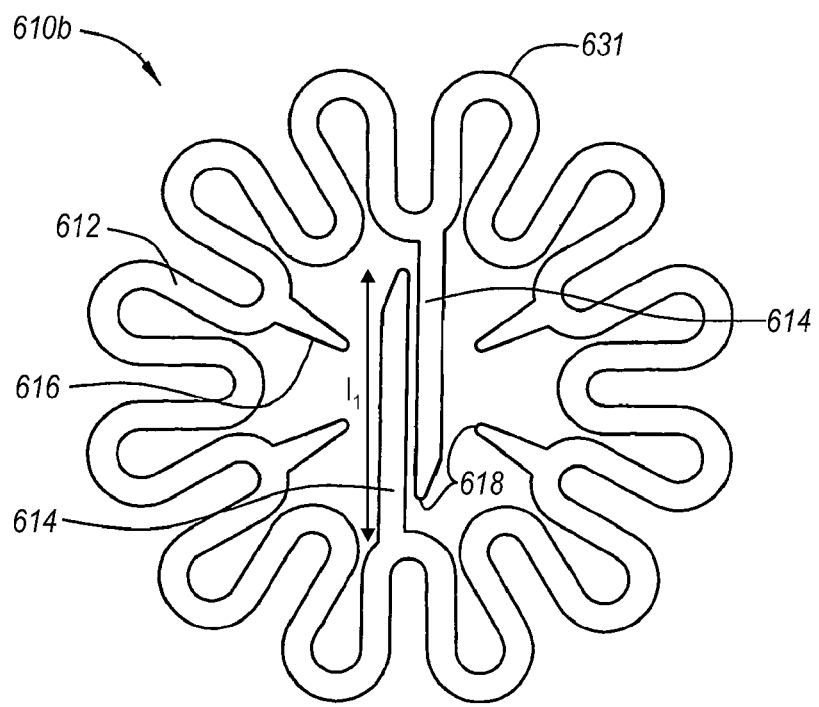

The precursor 610 may be reconfigured by imposing a radially inwardly directed force on body 612 such that precursor 610 may take a smaller planar shape such as one of those shown in FIG. 7B. The precursor 610 may include a planar body 612, primary and secondary tissue engaging portions 614, 616 having tip portions 618, and curved regions 631 that may connect the tissue engaging portions 614, 616 as previously described with regard to FIG. 4E. Furthermore, as previously described with regard to FIG. 4E, although the length, $l_1$, of the preconfigured precursor 610a in FIG. 7A is illustrated as extending from a curved region (not shown), to the central axis (not shown), it may be possible for the length, $l_1$, to be less than this distance, such as a length defined from a curved region to the central axis or a length defined from a curved region past the central axis, as shown in reconfigured precursor 610b shown in FIG. 7B.

After reconfiguring the precursor 610, the reconfigured precursor 610 may be heat set and quenched as described above to complete the manufacture of the device 610 for managing access through tissue.

Figure 8A:
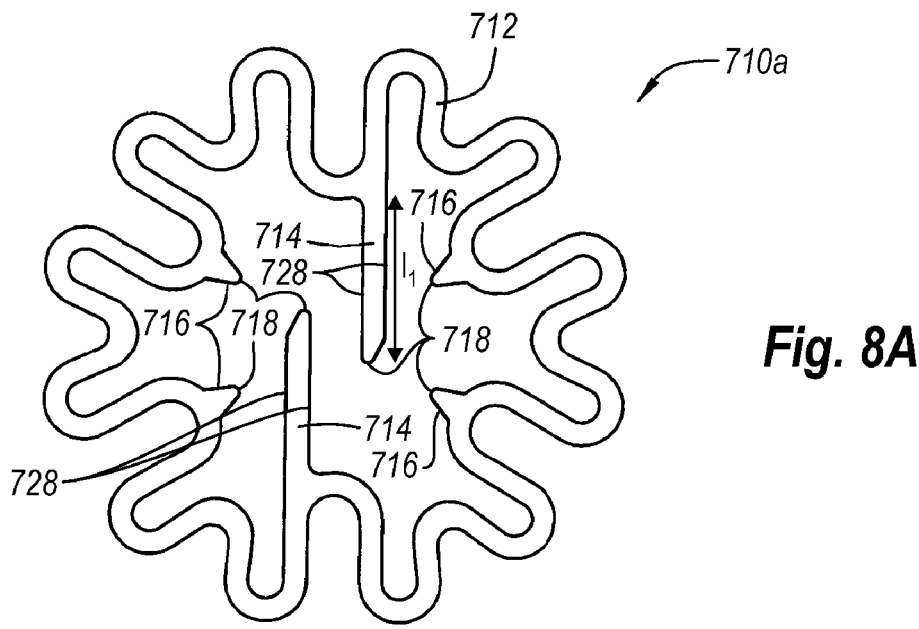
FIGS. 8A-8C illustrate another embodiment of a manufacturing precursor of devices for managing access to tissue according to the present invention.
Figure 8B:
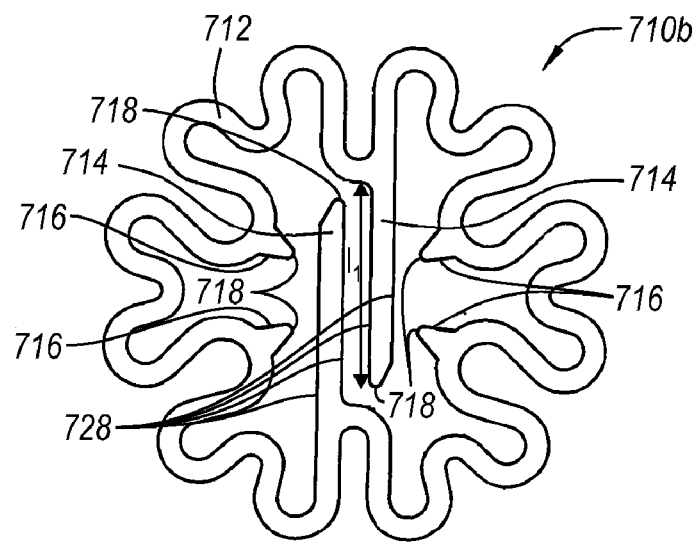
Figure 8C:
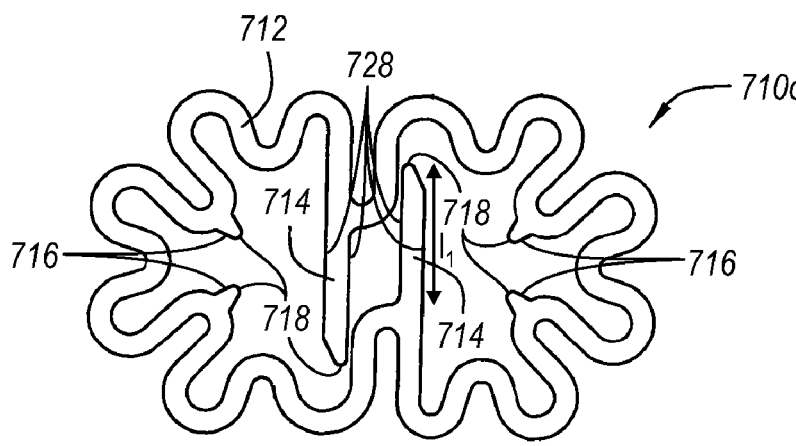

Devices 10 of still other configurations can be manufactured in the manner of device 710 for managing access through tissue by starting with a differently shaped precursor such as precursor 710a shown in FIG. 8A. The precursor 710 may a body 712 having tissue engaging portions 714, 716 with tip portions 718 and/or edges 728. Precursor 710a may be reconfigured by being subjected to radially inward deforming forces as shown in FIG. 8B or by opposed laterally inward forces as shown in FIG. 8C. In each case, the body 712 may be caused to take a smaller dimension and may be heat set as described above to form devices 710b and 710c.

Although the lengths, $l_1$, are illustrated in FIGS. 8A-8C as extending from a curved region (not shown), beyond the central axis (not shown), it may be possible for the length, $l_1$, to be less than this distance, such as a length defined from a curved region to the central axis or a length defined from a curved region toward, but not passing the central axis.

Figure 12:
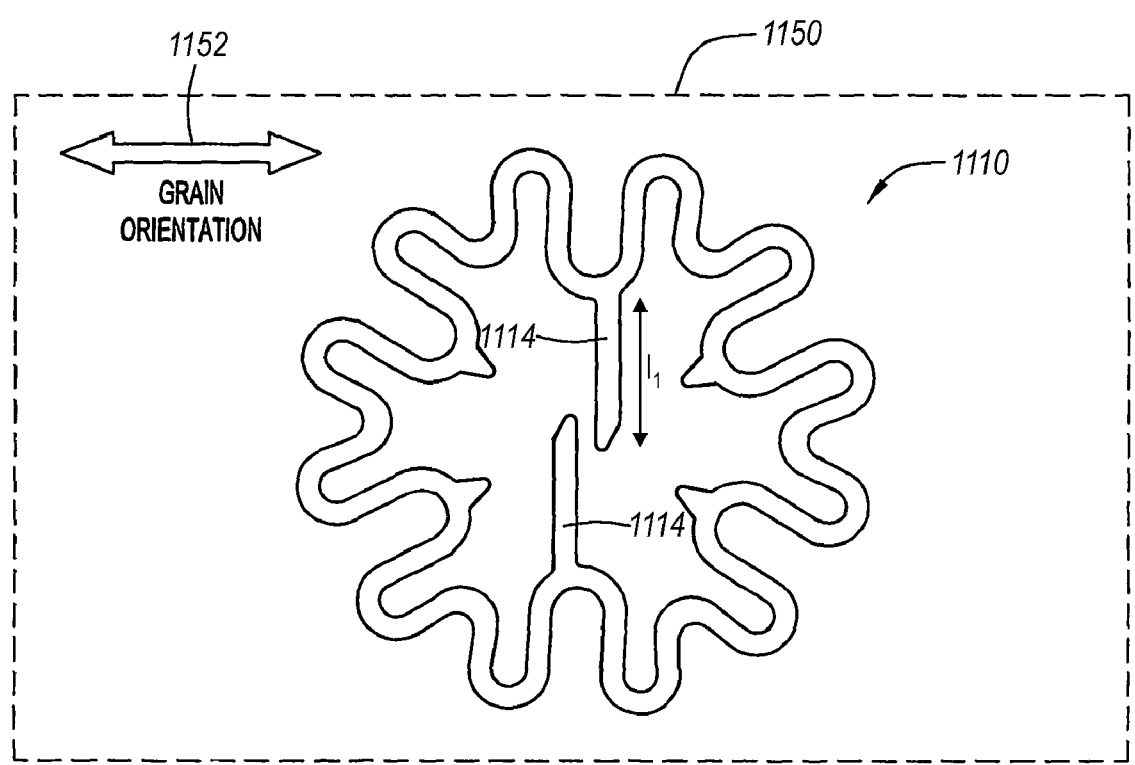
FIG. 12 illustrates a relationship between the grain orientation of a sheet and the primary tines of a precursor of a device for managing access through tissue.

It has been found that NITINOL® sheet is typically stronger in one direction than in others, which may be the result of crystal orientation in the NITINOL®. The device precursors 310e, 610, 710 may be formed such that the primary tissue engaging portions 214 are aligned with the strongest orientation of the NITINOL®. It has been found, as shown in FIG. 12, that the greatest strength of the primary tissue engaging portions 1114 typically may be achieved if those tissue engaging portions 1114 are transverse to the grain orientation of the NITINOL®. Thus, FIG. 12 illustrates a device precursor 1110 having primary tissue engaging portions 1114 as the precursor would be cut from sheet 1150. The grain orientation of sheet 1150 is shown by the double-headed arrow 1152. Typically, a plurality of precursors 310e, 610, 710, 1110 would be cut from the same sheet 1150, each with its primary tissue engaging portions 214 transverse to the grain orientation of the sheet 1150. In addition, even if devices 10 are formed directly without using precursors, it may be desirable that their primary tissue engaging portions 214 be transverse to the grain orientation 1152.

Although the length, $l_1$, is illustrated as extending from a curved region (not shown), beyond the central axis (not shown), it may be possible for the length, $l_1$, to be less than this distance, such as a length defined from a curved region to the central axis or a length defined from a curved region toward, but not passing the central axis.

Figure 10:
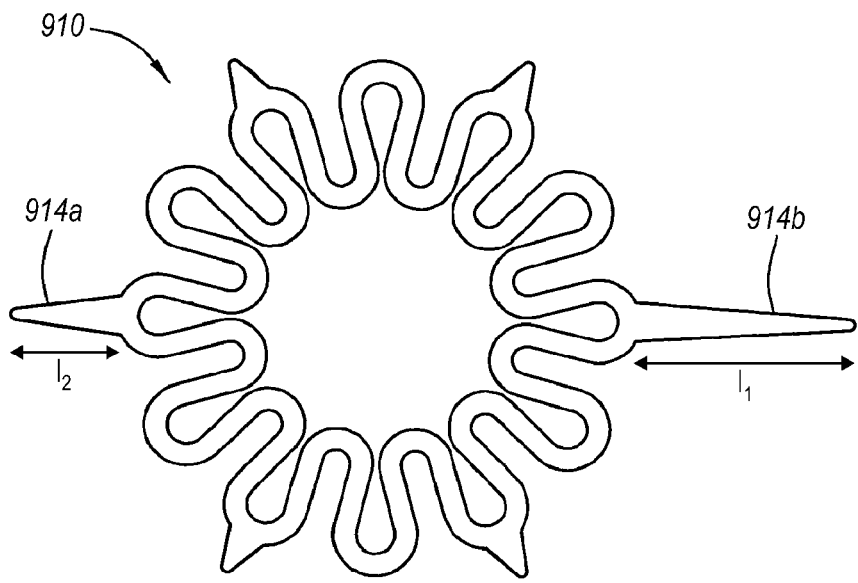
FIG. 10 illustrates another embodiment of a manufacturing precursor of devices for managing access to tissue including a primary tissue engaging portion that is shorter than primary tissue engaging portion according to the present invention.
Figure 11:
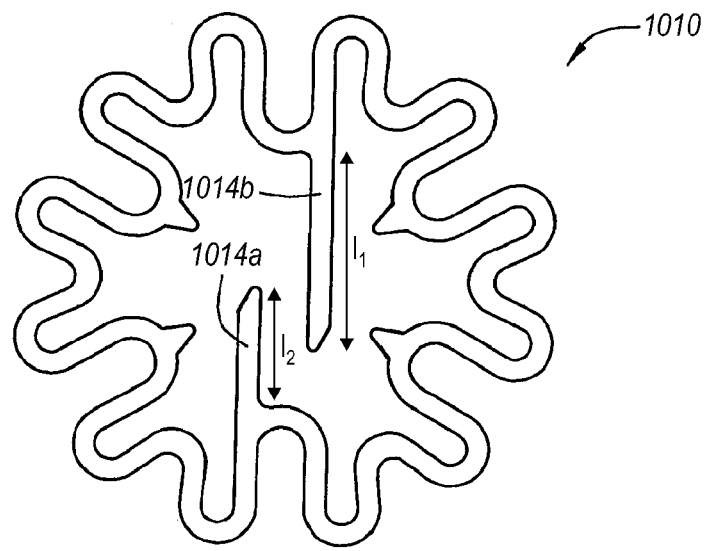
FIG. 11 illustrates a further embodiment of a manufacturing precursor of devices for managing access to tissue including a primary tissue engaging portion that is shorter than primary tissue engaging portion according to the present invention.

The devices 10 for managing access through tissue of the present invention may have primary or secondary tissue engaging portions 214, 216 that may have the same or different lengths and the tissue engaging portions 13 may be straight and/or curved. For example, radially opposed tissue engaging portions 13 may have one tissue engaging portion at "12 o'clock" which is longer than the opposing tissue engaging portion at "6 o'clock." Exemplary configurations of device 910, 1010 for managing access through tissue precursors with primary tissue engaging portions of different length are shown in FIGS. 10 and 11. In FIG. 10, the device precursor 910 is shown with a primary tissue engaging portion 914a that is shorter than primary tissue engaging portion 914b. Similarly, in FIG. 11, a device precursor 1010 is shown which has a primary tissue engaging portion 1014a that is shorter than primary tissue engaging portion 1014b. Furthermore, although the lengths, $l_1$ and $l_2$, are illustrated in FIGS. 10 and 11 as extending from a curved region (not shown), beyond the central axis (not shown), it may be possible for the lengths, $l_1$ and $l_2$, to be less than this distance, such as a length defined from a curved region to the central axis or a length defined from a curved region toward, but not passing the central axis (as shown by the first primary tines 914a, 1014a in FIGS. 10 and 11).

Figure 13:
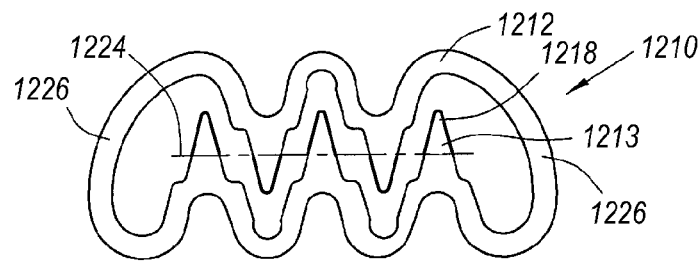
FIG. 13 illustrates an embodiment of a device for managing access through tissue according to the present invention.

FIG. 13 is another embodiment of a device 1210 for managing access through tissue according to the present invention. The device 1210 may include a peripheral body 1212 and a plurality of tissue engaging portions 1213 terminating in tip portions 1218. The device 1210 may be formed from a single sheet of material, such as NITINOL®, similar to embodiments described above. Furthermore, the device 1210 may include edges (not shown) as described in connection with FIGS. 2A-2F.

Figure 14:
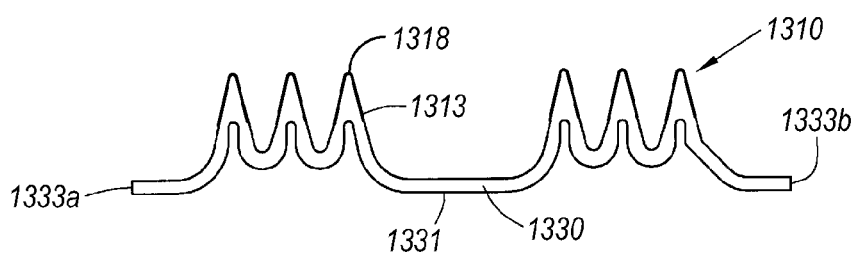
FIG. 14 illustrates another embodiment of a device for managing access through tissue including an elongate wire according to the present invention.

FIG. 14 illustrates another embodiment of a device 1310 for managing access through tissue according to the present invention. In the present embodiment, the device 1310 may be formed from an elongate wire, e.g., a solid rod or hollow tube, such as a length of hypotube. The tube may be semi-rigid or flexible, thereby accommodating deflection of the device 1310 between its deployed, pre-deployed, and/or access configurations. The tube may be bent to form tissue engaging portions 1313 using conventional methods. Alternatively, tissue engaging portions 1313 may be formed separately and attached to the tube, for example, by welding. The tube 1360 may then be wound into an enclosed loop and the ends 1333a, 1333b may be connected together, e.g., by welding, to provide a device 1310 for managing access through tissue, such as that shown in FIG. 13.

In the present embodiment, the tissue engaging regions 1313 may be disposed in opposing sets along an axis of symmetry (not shown) extending between looped regions 1331, defining a substantially planar deployed configuration. The tissue engaging portions 1313 may be directed substantially transversely, in a pre-deployed configuration (not shown), with respect to a plane defined by the deployed configuration. The tissue engaging portions 1313 may be biased to return towards the deployed configuration. Furthermore, the device 1310 may include edges (not shown) as described in connection with FIGS. 2A-2F.

Figure 15A:
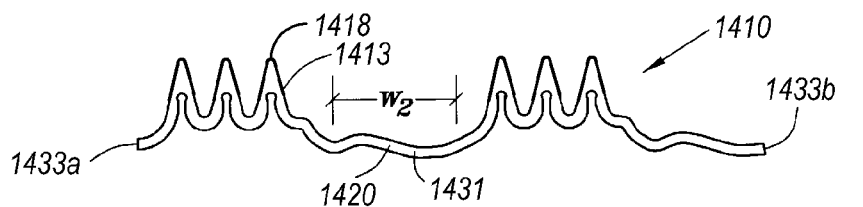
FIGS. 15A-15B illustrate a further embodiment of a device for managing access through tissue according to the present invention.
Figure 15B:
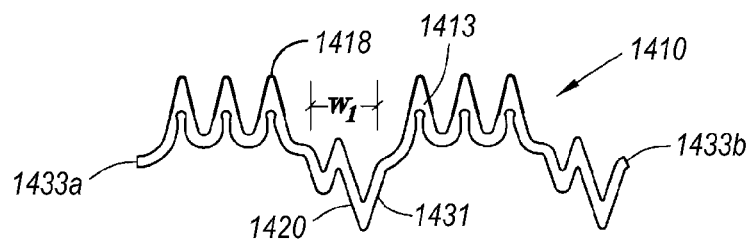
Figure 16A:
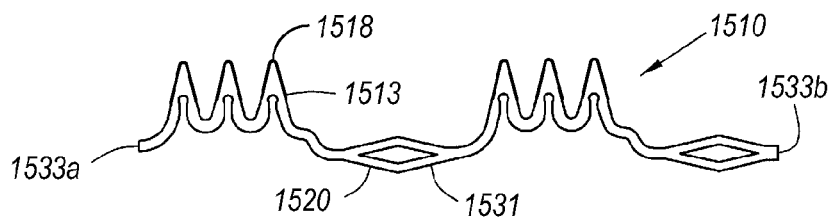
FIGS. 16A-16B illustrate a still further embodiment of a device for managing access through tissue according to the present invention.
Figure 16B:
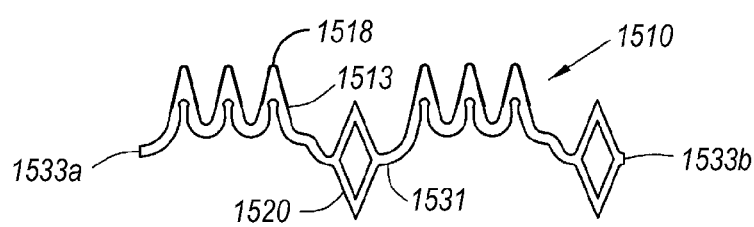

In an alternative embodiment, shown in FIGS. 15A and 15B, the regions 1431 between the tissue engaging portions 1413 may include expandable elements 1420, having a zigzag shape, that are expandable between a compressed state and an expanded state. Thus, when the tube is wound to form a device 1410 for managing access through tissue, the zigzag elements 1420 may be disposed at the looped regions 1331 of the device. The zigzag elements 1420 may include a first width $w_1$ in the compressed state (FIG. 15B) and a second width $w_2$ gin the expanded state that is larger than the first width (FIG. 15A). In a further alternative embodiment, shown in FIGS. 16A and 16B, the expandable elements may be substantially enclosed cells 1520. The substantially enclosed cells 1520 may have a diamond shape. Thus, the expandable elements or cells may allow the device 1510 to assume first and second diameters. Furthermore, the devices 1410, 1510 may include edges (not shown) as described in connection with FIGS. 2A-2F.

Referring now to FIGS. 17A-17D, an illustrative device 1610 for managing access through tissue is shown. FIG. 17B is a side view of the device 1610 of FIG. 17A rotated 90 degrees, wherein device 1610 is in a pre-deployed configuration. The device 1610 may comprise an annular body 1612 having upper members 1670 joined to lower members 1672 by legs 1674 to form lumen 1680. Outer tissue engaging portions 1613a and/or inner tissue engaging portions 1613b may be connected to lower members 1672. The device 1610 may be elastically expanded by advancing an introducer sheath (not shown) or expander (not shown) through lumen 1680. In the pre-deployed configuration, the lower members 1672 may be separated by a distance, $d_2$.

Upon removal of the introducer sheath, the device 1610 may resiliently return to the deployed configuration, illustrated in FIGS. 17C and 17D, where FIG. 17C corresponds to the view of FIG. 17A and FIG. 17D corresponds to the view of FIG. 17B. When removed from the exterior of the introducer sheath, the device 1610 may resume its deployed shape, in which the opposing sides of the device 1610 may come together until lower members 1672 contact one another (i.e. the distance $d_1$ between the lower members 1672 is zero), and outer tissue engaging portions 1613a cross inner tissue engaging portions 1613b.

As depicted in FIG. 17A, the device 1610 also may include tip portions 1618. Each of the tissue engaging portions 1613 may include a variety of tip portions 118 and/or edges 128 as described in connection with FIGS. 2A-2F.

FIGS. 18A and 18B illustrate another embodiment of a device 1710 for managing access through tissue according to the present invention. The device 1710 may comprise a body 1712 and tissue engaging portions 1713. In the present embodiment, the body 1712 may comprise a hoop. The tissue engaging portions 1713 may include tip portions (not shown) and/or edges (not shown). For example, each of the tissue engaging portions 1713 may include a variety of tip portions and/or edges as described in connection with FIGS. 2A-2F.

In FIG. 18A, the device 1710 is depicted in the deployed configuration, in which opposing tissue engaging portions 1713 may approach and/or contact one another, such that the tissue engaging portions 1713 may be separated by a first distance $d_1$ (which may be zero when the tissue engaging portions 1713 touch). In FIG. 18B the device 1710 is depicted in a pre-deployed configuration, in which opposing tissue engaging portions 1713 are separated by a distance $d_2$. The device 1710 may be elastically expanded in a manner similar to the device 1610 of the previous embodiment by advancement over an introducer sheath (not shown).

Figure 19:
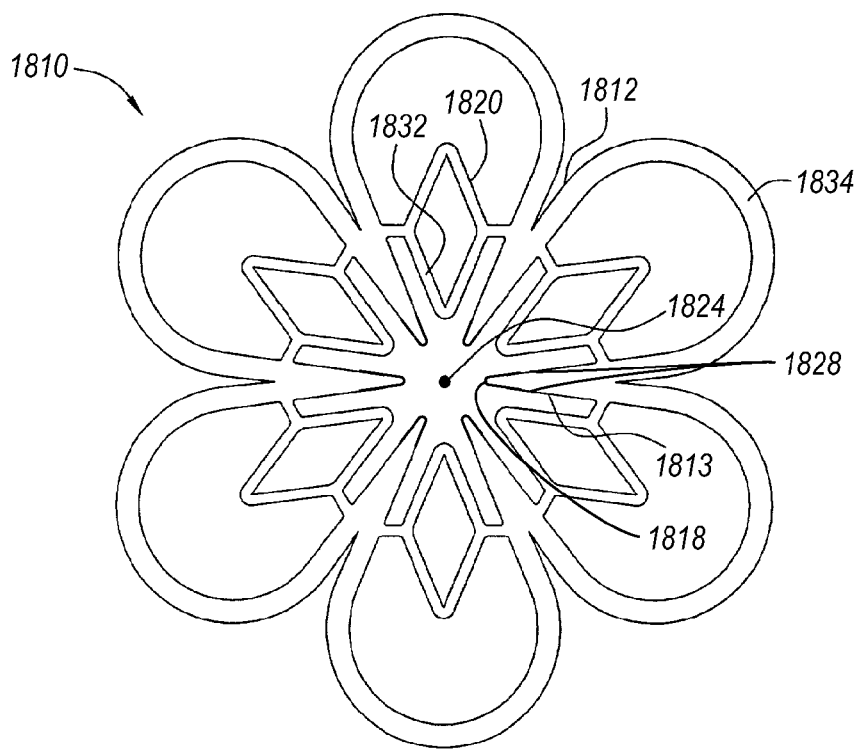
FIG. 19 illustrates an embodiment of a device for managing access through tissue according to the present invention.

Turning to FIG. 19, another embodiment of a device 1810 for managing access through tissue according to the present invention is shown. The device 1810 may include a body 1812, a plurality of tissue engaging portions 1813, and/or a plurality of expandable elements 1820 that may interconnect adjacent tissue engaging portions 1813. The body 1812 may include outer curved regions 1834 that may extend between adjacent tissue engaging portions 1813, thereby defining an outer periphery (not shown) for the device 1810. The expandable elements 1820, in the present embodiment, may be spring elements.

The device 1810 may be moveable between a deployed configuration, which is substantially planar in the present embodiment, such as that shown in FIG. 19, and a pre-deployed configuration, which is substantially transverse to the deployed configuration in the present embodiment. The device 1810 may be biased towards the deployed configuration.

In the present embodiment, the expandable elements 1820 may generally be hollow diamond shaped elements, including curved inner regions 1832 oriented towards the central axis 1824 of the body 1812 when the device 1810 is in the deployed configuration. The expandable elements 1820 may serve multiple purposes. One purpose may include biasing the device 1810, e.g., allowing the device 1810 to at least partially expand resiliently. For example, when the device 1810 is deflected into the pre-deployed configuration (not shown), the expandable elements 1820 may allow the tissue engaging portions 1813 to be moved away from the central axis 1824 and/or one radially outwardly or otherwise expanded to engage a larger area of tissue.

As the tissue engaging portions 1813 are expanded, the expandable elements 1820 may deform to become wider (along a dimension extending generally between the adjacent tissue engaging portions 1813) and shorter (along a dimension extending generally parallel to the tissue engaging portions 1813). Once a force causing the tissue engaging portions 1813 to expand is removed, the expandable elements 1820 may resiliently try to return towards their original shape, thereby pulling the tissue engaging portions 1813 substantially closer towards one another towards the deployed configuration.

In addition, the curved inner regions 1832 of the expandable elements 1820 may provide stops limiting penetration of the tissue engaging portions 1813 into tissue, similar to the stop members described above. For example, when the device 1810 is in the pre-deployed configuration and the expandable elements 1820 are expanded, the curved inner regions 1832 may be become more oblique, possibly becoming generally linear. Thus, in embodiments where the tissue engaging portions 1813 penetrate the tissue, the curved inner regions 1832 may limit penetration of the tissue engaging portions 1813.

Finally, after the device 1810 is deployed, e.g., the tissue engaging portions 1813 have penetrated and/or engaged the tissue, the curved inner regions 1832 may return towards the deployed configuration, and may pinch or otherwise engage tissue between the inner curved regions 1832 and the adjacent tissue engaging portions 1813. Thus, contracting the expandable elements 1820 may enhance the ability of the device 1810 to seal a puncture site, e.g., by pulling engaged tissue inwardly towards the central axis 1824 of the device 1810.

Figure 20:
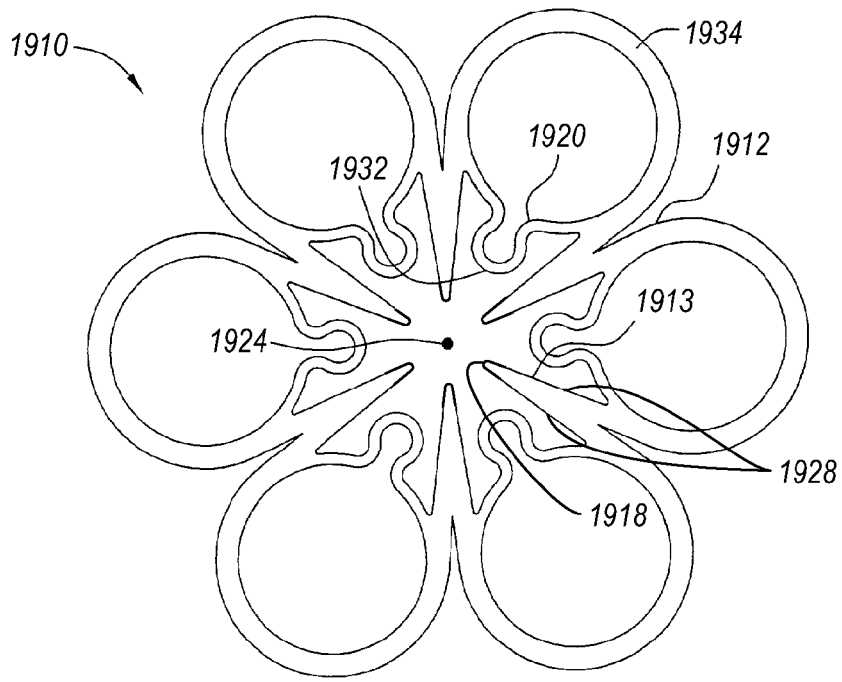
FIG. 20 illustrates another embodiment of a device for managing access through tissue according to the present invention.

Turning to FIG. 20, a further embodiment of a device 1910 for managing access through tissue is shown. The device 1910 may be substantially similar to the device 1810 shown in FIG. 19, with the exception of the shape of the expandable elements 1820. In the present embodiment, rather than diamond shaped elements 1820, the expandable elements 1920 may be looped elements generally defining a circular shape.

Turning now to FIG. 21, another embodiment of a device 2010 for managing access through tissue according to the present invention is illustrated. The device 2010 may include a body 2012 that may be generally annular-shaped and/or may define a plane. In the present embodiment, the body 2012 may be disposed about a central axis 2024 that may extend through the plane. The body 2012 may include a plurality of outer curved elements 2030 that may extend between adjacent tissue engaging portions 2013 and may be connected to each other to form the body 2012. When the device 2010 is in the deployed configuration, a substantially planar configuration in the present embodiment as shown in FIG. 21, the curved elements 2030 may define an outer periphery 2038 of the device 2010.

The tissue engaging portions 2013 may be curved or arcuately shaped and may include tip portions 2018 that may extend toward the central axis 2024 when the device 2010 is in a deployed configuration. The curves of the tissue engaging portions 2013 may all be in phase with one another such that the tissue engaging portions 2013 spiral about the central axis 2024. This may allow a length of the tissue engaging portions 2013 to be maximized for a given diameter of the body 2012.

For example, the tissue engaging portions 2013 may have a length that is greater than a radius of the body 2012 without the tip portions 2018 of the tissue engaging portions 2013 touching one another. Thus, due to the arcuate shape of each tissue engaging portion 2013, the tissue engaging portions 2013 of device 2010 may be generally longer than the straight tissue engaging portions of the previous devices having comparable diameters. The tissue engaging portions 2013 may, therefore, penetrate deeper into and/or apply pressure to tissue than the tissue engaging portions of the other devices.

The body 2012 and/or the tissue engaging portions 2013 of device 2010 may be deflected until the tissue engaging portions 2013 extend transversely with respect to the deployed configuration, thereby defining a pre-deployed configuration (not shown), which may be transverse in the present embodiments. In the pre-deployed configuration, the tissue engaging portions 2013 may be oriented substantially parallel to the central axis 2024. Additionally, the tissue engaging portions 2013 and/or body 2012 may be biased to move from the pre-deployed configuration towards the deployed configuration. The device 2010 may be delivered in substantially the same manner as will be described with respect to other devices of the present invention.

Turning to FIG. 22, another embodiment of a device 2110 for managing access through tissue according to the present embodiment is shown. The device 2110 may include a peripheral body 2112 and a plurality of tissue engaging portions 2113. Each tissue engaging portion 2113 may include a pair of legs 2117 terminating in a tissue engaging portion 2118. The tissue engaging portions 2114 may be disposed substantially symmetrically about a central axis 2124. The body 2112 may include a plurality of expandable elements 2120. The expandable elements 2120 may be connected by hinged regions 2122 that may also connect adjacent tissue engaging portions 2113.

The tissue engaging portions 2113 may be deflected from a deployed configuration, shown in FIG. 22, to a pre-deployed configuration (not shown). In the present embodiment, the tissue engaging portions 2113 may be deflected such that they extend substantially transversely from the body 2112 to the pre-deployed configuration. In this pre-deployed configuration, the tissue engaging portions 2113 may be oriented substantially parallel to the axis 2124 such that the body 2112 has a generally annular shape (not shown). The tissue engaging portions 2113 may be biased from the pre-configured configuration towards the deployed configuration shown in FIG. 22.

The expandable elements 2120 may have a generally arcuate shape that may be expandable from a first width to a second wider width (not shown), behaving similarly to the diamond-shaped cells of the embodiment shown in FIGS. 6A-6E. Thus, the expandable elements 2120 may be biased to the expanded state, but may be compressed to the compressed state, as described above.

Turning to FIG. 23, another embodiment of a device 2210 for managing access through tissue according to the present invention is shown. The device 2210 may include a peripheral body 2212 including a plurality of legs 2217 extending between tissue engaging portions 2213, expandable elements 2220, and/or hinged regions 2222. The device 2210 may be formed from a single sheet of material, similar to embodiments described above. The tissue engaging portions 2213 may be biased to a deployed configuration, as shown. The body 2212 may be deflectable to a pre-deployed configuration (not shown). In the present embodiment, the tissue engaging portions 2212 may be oriented substantially transversely with respect to the plane of the sheet in the pre-deployed configuration. The body 2212, and particularly the arms 2216 in the present embodiment, may be sufficiently flexible such that the device 2210 may assume a generally annular shape in the pre-deployed configuration, e.g., to facilitate loading of the device 2210 for managing access through tissue onto a delivery device (not shown).

The expandable elements 2220 may be substantially enclosed loops that may at least partially open from a compressed state (shown in FIG. 23), to an expanded state (not shown). The loops may be biased to the expanded state, similar to embodiments described above, thereby allowing the device 2210 for managing access through tissue to assume a reduced diameter and an expanded diameter.

Turning to FIG. 24, a further embodiment of a device 2310 for managing access through tissue according to the present invention is shown. The device 2310, in the present embodiment, may include two expandable elements 2320. The expandable elements 2320 may be disposed in a substantially symmetrical arrangement to facilitate expansion of the device 2310 in a generally uniform manner. A device 10 for managing access through tissue in accordance with the present invention may have a variety of configurations, including two or more tissue engaging portions or tissue engaging portions, and including one or more expandable elements (or optionally no expandable elements). The tissue engaging portions and/or expandable elements may be arranged in a substantially symmetrical configuration, for example, about a central axis.

In a further embodiment of a device 2410 for managing access through tissue according to the present invention, shown in FIG. 25, the device 2410 may include primary tissue engaging portions 2414 having a first length $l_1$, and secondary tissue engaging portions 2414 having a second length $l_2$ that may be substantially shorter than the first length $l_1$. In the present embodiment, the device 2410 may be deployed such that the primary tissue engaging portions 2414 penetrate into and/or engage tissue, i.e. the wall of a blood vessel, body lumen, and/or other tissue, while the secondary tissue engaging portions 2416 may engage extra-vascular tissue, i.e., tissue between the vessel wall and the patient's skin. Thus, the device 2410 may simultaneously close both the opening in the vessel wall and the passage through the intervening tissue.

Turning to FIG. 26, another embodiment of a device 2510 for managing access through tissue is shown, in accordance with the present invention. The device 2510 may include a peripheral body 2512 and a plurality of tissue engaging portions 2513. Each tissue engaging portion 2513 may include a pair of legs 2517 terminating in a tip portion 2518 configured for penetrating and/or otherwise engaging tissue. The tissue engaging portions 2513, in the present embodiment, may be disposed substantially symmetrically about a central axis 2524. The body 2512 may include a plurality of expandable elements 2520 that are connected by hinged regions 2522 that also connect adjacent tissue engaging portions 2513. The cells 2520 may behave similar to embodiments described above.

The device 2510 for managing access through tissue is shown in a deployed configuration. In the present embodiment, the tissue engaging portions 2513 may be disposed radially outward in a substantially planar configuration in the deployed configuration. The tissue engaging portions 2513 may be deflected such that they extend from the body 2512 in a pre-deployed configuration. In the present embodiment, the tissue engaging portions 2513 may be deflected such that they extend from the body 2512 substantially transversely with respect the plane defined by the sheet (similar to FIG. 6C), in a pre-deployed configuration (not shown).

The tissue engaging portions 2513 may be biased from the pre-deployed configuration away from one another, i.e., towards the deployed configuration. Thus, with the tissue engaging portions 2513 in the pre-deployed configuration, the tip portions 2518 may penetrate into and/or be engaged with tissue. When the device 2510 for managing access through tissue is released, e.g., from within a delivery device (not shown), the tissue engaging portions 2513 may be biased to return to the deployed configuration, thereby securing the tissue with respect to the device 2510 for managing access through tissue.

In addition, the device 2510 for managing access through tissue may include expandable elements 2520 that may be expandable from a compressed state to an expanded state (similar to FIG. 6C), similar to some of the previous embodiments. The expandable elements 2520 may be biased to the expanded state, but may be compressed to the compressed state, e.g., by constraining the device 2510. Alternatively, any of the devices described herein may be biased to the compressed state but may be expanded to the expanded state, e.g., by constraining the device for managing access through tissue over a sheath or other elongate member.

Figure 27:
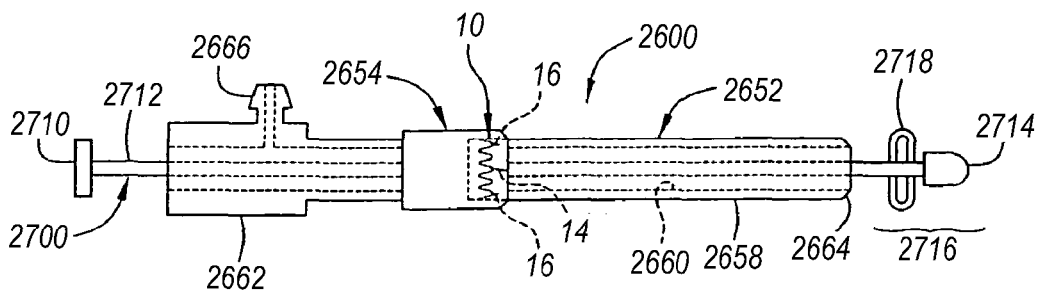
FIG. 27 illustrates an embodiment of an apparatus suitable for delivering a device for managing access through tissue according to the present invention.

The devices 10 for managing access through tissue of the present invention may be delivered using various apparatus and methods. An exemplary apparatus 2600 suitable for delivering a device 10 of the present invention is shown in FIG. 27. Other suitable apparatus that may be used to deliver a device 10 of the present invention are disclosed in co-pending U.S. patent application, Ser. No. 11/427,297, entitled "Clip Applier and Methods of Use", filed Jun. 28, 2006, which is incorporated herein by reference in its entirety and which is assigned to the assignee of the present application. The disclosures of this application and any references cited therein are expressly incorporated by reference.

The apparatus 2600 may include an introducer sheath 2652 and/or a housing or carrier assembly 2654 slidably disposed on the sheath 2652. The sheath 2652 may include a substantially flexible or semi-rigid tubular body 2658 including a lumen 2660 extending between its proximal and distal ends 2662, 2664. In some embodiments, the distal end 2664 may have a size and/or shape configured to facilitate insertion into a blood vessel, e.g., having a tapered tip for facilitating substantially atraumatic introduction through the passage and at least partially into the vessel. In other embodiments, the distal end 2664 may have other sizes and/or shapes. The lumen 2660 may have a size and/or shape for inserting one or more devices therethrough. In the present embodiment, the lumen 2660 may be configured to receive one or more medical devices, such as a catheter, guide wire, and/or other medical devices (not shown). The sheath 2652 may include one or more seals (not shown), such as a hemostatic valve, within the lumen 2660 at or near the proximal end 2662 that may provide a fluid-tight seal, while yet accommodating the insertion of one or more devices into the lumen 2660 without fluid passing proximally from the sheath 2652.

Optionally, the sheath 2652 may include a side port 2666 that may communicate with the lumen 2660, for example, to deliver fluids into the lumen 2660. Alternatively, or in addition, the side port 2666 may be used to provide a "bleed back" indicator.

The apparatus 2600 may also include a mechanical locator or obturator 2700 that may be part of an actuator assembly (not shown) that may be attachable to the proximal end of the sheath 2652. Alternatively, the mechanical locator or obturator 2700 may be a separate device that is insertable into the lumen 2660, e.g., through the actuator assembly. Generally, the obturator 2700 may be an elongate member including a distal tip 2714 and a distal portion 2716. The distal tip 2714 may be substantially soft and/or flexible such that the distal tip 2714 may substantially atraumatically enter tissue. The distal portion 2716 generally includes one or more wings or other expandable elements 2718 for providing tactile feedback, as described further below.

The carrier assembly 2654 may be slidably disposed on an exterior of the sheath 2652. The carrier assembly 2654 may be configured for releasably carrying a device 10 for managing access through tissue (shown in phantom), which may incorporate elements of the various embodiments of the devices described herein. The carrier assembly 2654 may be substantially permanently attached to the sheath 2652 and/or may be actuated from the proximal end 2662 of the sheath 2652, for example, by the actuator assembly (not shown), to advance the device 10 distally during deployment. Alternatively, the device 10 may be carried by an actuator assembly.

Turning to FIGS. 28A-28F, the apparatus 2600 may be used to deliver the device 10 for managing access through tissue. In the present example, the device 10 may be used to substantially close and/or seal an incision, puncture, or other passage 2692 that extends from a patient's skin 2694, through intervening tissue 2696, and into a wall 2698 of a vessel 2690 or other body lumen. Alternatively, the apparatus 2600 may be used to deliver the device 10 to engage tissue in other procedures, e.g., to connect tissue segments together or otherwise to secure tissue structures with respect to one another. For example, the apparatus 2600 and device 10 may be used to attach an anastomosis during a bypass procedure. In another example, the apparatus 2600 and device 10 may be used to close an aperture (i.e. a puncture, cut, tear, and/or other aperture) on the surface of the patient's skin 2694. Although the device 10 and/or apparatus 2600 may be useful in a variety of procedures, the following example illustrates the usefulness of the device 10 and/or apparatus 2600 to substantially close and/or seal an incision, puncture, or other passage 2692 that extends from a patient's skin 2694, through intervening tissue 2696, and into a wall 2698 of a vessel 2690 or other body lumen.

Figure 28A:
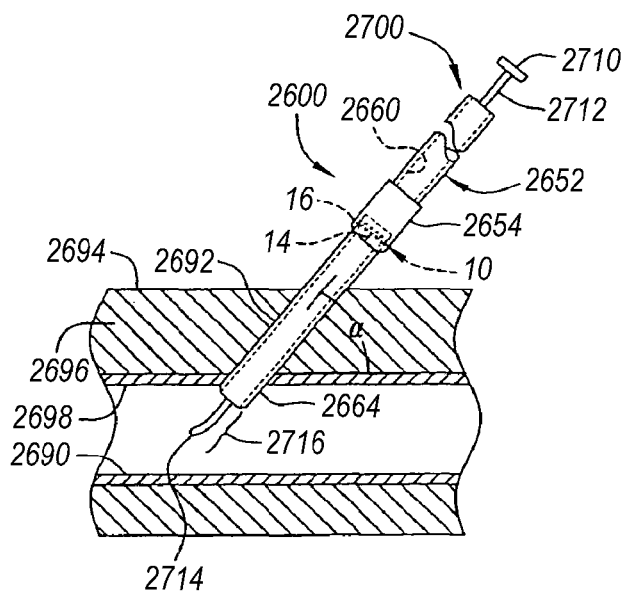
FIGS. 28A-28F are cross-sectional views of a blood vessel, showing a method for delivering a device for managing access through tissue into a passage communicating with the vessel using the apparatus of FIG. 27.

As shown in FIG. 28A, the sheath 2652 may be inserted or otherwise positioned within the vessel 2690, i.e., through the passage 2692. The sheath 2652 may be advanced over a guide wire or other rail (not shown) previously positioned through the passage 2692 into the vessel 2690 or advanced in conjunction with a pointed stylet directly through tissue using conventional procedures. The vessel 2690, in the present example, may be a peripheral vessel, such as a femoral, radial, or carotid artery, although other body lumens may be accessed using the sheath 2652.

The passage 2692, and consequently the sheath 2652, may be oriented at an angle "alpha" with respect to the vessel 2690, thereby facilitating introducing devices through the lumen 2660 of the sheath 2652 into the vessel 2690 with minimal risk of damage to the vessel 2690. One or more devices, such as a guide wire, a catheter, and the like (not shown), may be inserted through the sheath 2652 and advanced to a desired location within the patient's body. In the present example, the devices may be used to perform a first therapeutic or diagnostic procedure, such as angioplasty, atherectomy, stent implantation, and/or other procedure, within the patient's vasculature. In other examples, other procedures may be performed.

After the first procedure is complete, any devices used during the procedure may be removed from the sheath 2652, and the obturator 2700 may be inserted into the lumen 2660. For example, the obturator 2700 may be part of an actuator assembly (not shown), and may be advanced through the lumen when the actuator assembly is attached to the proximal end of the sheath 2652. Alternatively, the actuator assembly and obturator 2700 may be coupled separately to the sheath 2652.

When the obturator 2700 is fully inserted within the sheath 2652, the distal portion 2716 of the obturator 2700 may extend beyond the distal end 2664 of the sheath 2652. In an alternative embodiment, the obturator 2700 may be attached to an exterior surface (not shown) of the sheath 2652, for example, along a track, e.g., including cooperating slots, grooves, and the like (not shown) in the sheath 2652 and obturator 2700.

Figure 28B:
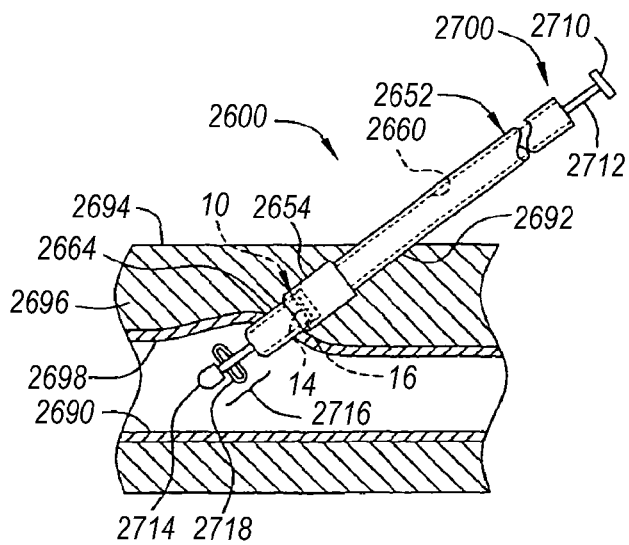

Turning to FIG. 28B, the expandable elements 2718 on the distal portion of the obturator 2700 may then be directed to their expanded configuration, for example, by activating a switch on the proximal end (not shown) of the obturator 2700. In some embodiments, the sheath 2652 and obturator 2700 may be coupled to one another, such that the sheath 2652 and obturator 2700 may be moved in conjunction with one another.

Figure 28C:
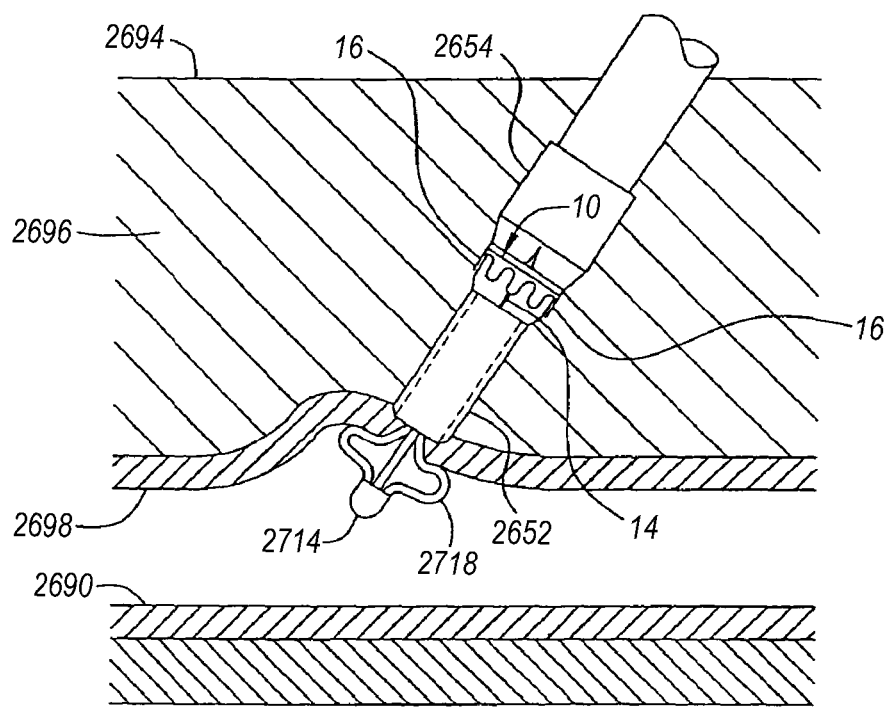

As shown in FIG. 28C, the sheath 2652 may be partially withdrawn from the vessel 2690, until the expandable elements 2718 contact the wall 2698 of the vessel 2690. Thus, the expandable elements 2718 may provide a tactile indication of the position of the sheath 2652 with respect to the wall 2698 of the vessel 2690. In addition, the expandable elements 2718 may assist in "presenting" the wall 2698 of the vessel 2690, e.g., for receiving the device 10.

Generally, the device 10 may be carried by the carrier assembly 2654 before the first procedure. The device 10 may be constrained in its pre-deployed configuration on the carrier assembly 2654, and the carrier assembly 2654 may be provided on and/or adjacent to the proximal end of the sheath 2652. Because the tissue engaging portions, which may include primary and secondary tissue engaging portions 314, 316 may be biased towards one another, the tissue engaging portions 314, 316 may slidably contact an inner surface (not shown) of the carrier assembly 2654 or an outer surface of the sheath 2652, thereby constraining the device 10 in its pre-deployed configuration.

Figure 28D:
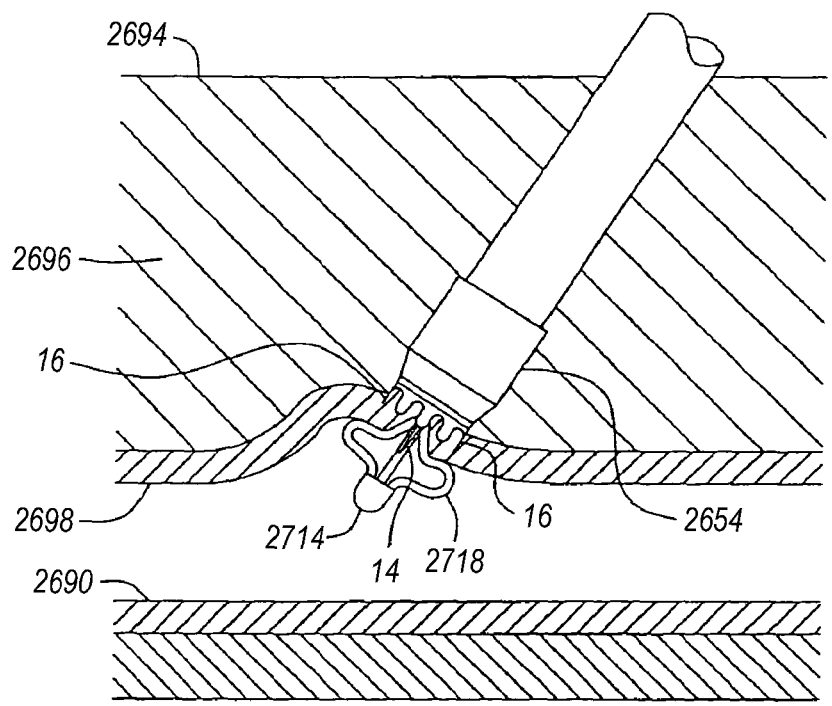

Turning to FIG. 28D, with the sheath 2652 properly positioned, the carrier assembly 2654 may then be actuated, for example, to advance the carrier assembly 2654 distally over the sheath 2652 to deliver the device 10. The carrier assembly 2654 may only be advanced a predetermined fixed distance relative to the distal end of the sheath 2652, and consequently, the expandable elements 2718 of the obturator 2700, such that the device 10 may substantially engage the wall 2698 of the blood vessel 2690. This predetermined distance may facilitate properly deploying the device 10 with respect to the wall 2698 of the vessel 2690, e.g., to prevent advancing the device 10 too far, i.e., into the vessel 2690.

As the device 10 is deployed from the carrier assembly 2654, the device 10 may be expanded to an enlarged diameter, as described, for example, in connection with FIGS. 1A-1D. In the present embodiment, a distal end of the carrier assembly 2654 may include a ramped region (not shown) that may deflect the tissue engaging portions 314, 316, and/or the body of the device 10 radially outwardly. As the device 10 is advanced over the ramped region, the tissue engaging portions 314, 316 may be deflected radially outwardly as they are being driven into the surrounding tissue, thereby engaging a larger region of tissue than if the tissue engaging portions 314, 316 had been maintained substantially axially.

Alternatively, the device 10 may include expandable looped elements and/or spring elements (not shown), such as those described above, that may facilitate expanding the device 10 as it is deployed from the carrier assembly 2654 and/or the sheath 2652. For example, the looped elements of the device 10 may be compressed when the device 10 is loaded into the carrier assembly 2654, e.g., thereby allowing a relatively smaller profile carrier assembly 2654 to be used. The device 10 may automatically expand upon deployment from the carrier assembly 2654 to engage a larger region of tissue surrounding the opening, such as an arteriotomy 2691 in the wall 2698 of the vessel 2690 (see FIG. 29A).

Figure 29A:
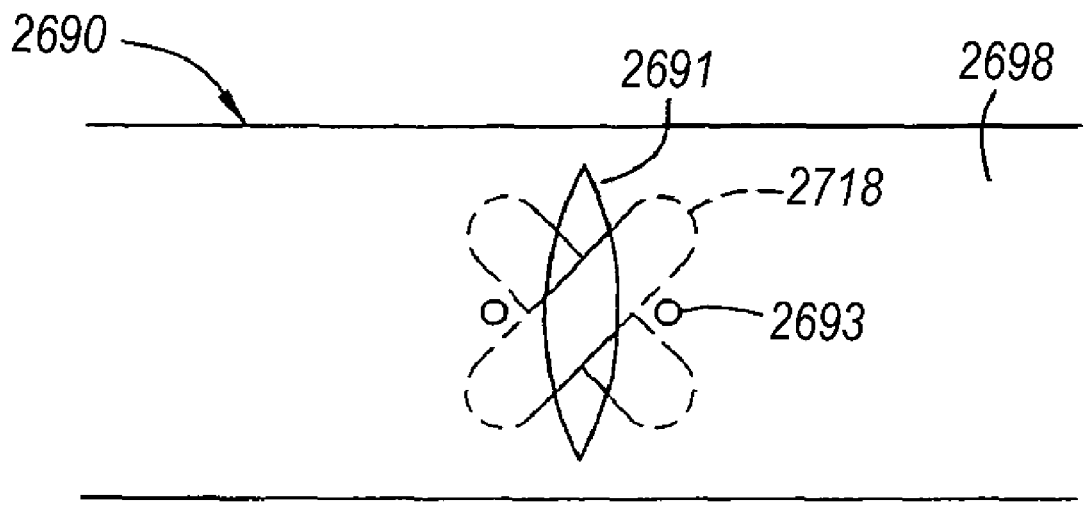
FIG. 29A is a top view of the blood vessel of FIGS. 28A-28F, showing the orientation of the expandable elements of the obturator and openings produced by primary tines of the device for managing access through tissue relative to an arteriotomy in the vessel.
Figure 29B:
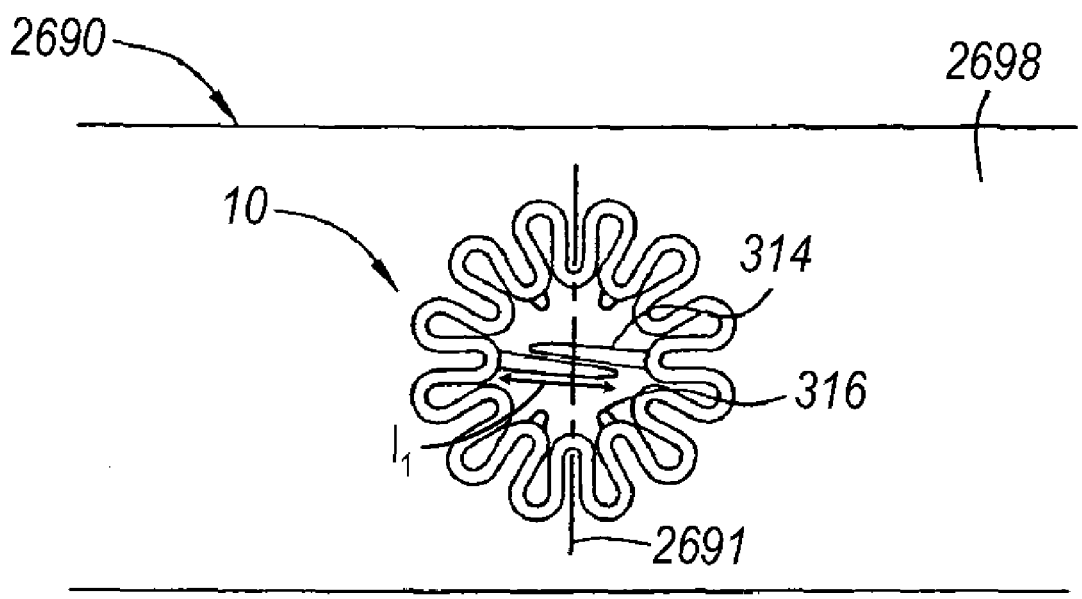
FIG. 29B is a top view of the blood vessel of FIG. 29A, showing the arteriotomy being closed by the device for managing access through tissue.

Once the device 10 is deployed entirely or otherwise released from the sheath 2652, the device 10 may resiliently move towards its deployed configuration, such as the substantially planar configuration shown in FIG. 29B. Although the length, $l_1$, in FIG. 29B is illustrated as extending from a curved region (not shown), beyond the central axis (not shown), it may be possible for the length, $l_1$, to be less than this distance, such as a length defined from a curved region to the central axis or a length defined from a curved region toward, but not passing the central axis, as discussed previously.

During delivery of the device 10, radiopaque markers (not shown) on the device 10, the carrier assembly 2654, and/or the expandable members 2718 may be monitored, e.g., using fluoroscopy, to facilitate observing and/or positioning the apparatus 2600. Thus, a relative position of the device 10 with respect to the expandable elements 2718, and consequently to the wall 2698 of the vessel 2690, may be ascertained before the device 10 is deployed from the carrier assembly 2654. Markings may also assist in locating a deployed device 10.

Turning to FIGS. 28A and 28B, in some embodiments, the expandable elements 2718 of the obturator 2700 may be rotationally offset from the one or more tissue engaging portions 314 on the device 10. For example, if the device 10 includes primary tissue engaging portions (such as those shown in FIGS. 2A-2D), the obturator 2700 and device 10 may have a predetermined relative angular orientation about the central axis 24. In the present example, the device 10 may be loaded onto the carrier assembly 2654 in a predetermined angular orientation and the obturator 2700 may be receivable in the sheath 2652 only in a predetermined angular orientation that is offset such that the tissue engaging portions 314, 316 are out of axial alignment with the expandable elements 2718, as shown in FIG. 29A.

This predetermined rotational orientation may substantially minimize the possibility of the primary tissue engaging portions 314 contacting and/or damaging the expandable elements 2718. For example, with particular reference to FIG. 29A, a relative angular orientation of the device 10 and obturator 2700 is shown relative to an arteriotomy 2691 in the wall 2698 of the vessel 2690. Here, the expandable elements 2718 may be oriented to crisscross diagonally the arteriotomy 2691 within the interior of the vessel 2690. Because of the natural structure of the tissue in the wall of a vessel, an arteriotomy generally tends to adopt an elongate shape that extends transversely to the direction of flow (i.e., across the circumference of the vessel wall).

The primary tissue engaging portions 314 may be oriented such that the primary tissue engaging portions 314 pierce and/or engage the wall 2698 of the vessel 2690 on either side of the arteriotomy 2691, as shown. With the expandable elements 2718 crisscrossing diagonally, risk of contact with the primary tissue engaging portions may be substantially reduced. Thus, in some embodiments, the primary tissue engaging portions 314 may be sufficiently long to extend entirely through the wall 2698 of the vessel 2690 while avoiding the expandable elements 2718.

The expandable elements 2718 may then be collapsed and/or withdrawn into the distal end 2664 of the sheath 2652. As the device 10 is released entirely from the sheath 2652, the primary tissue engaging portions 314 may partially overlap, as shown in FIG. 4A, thereby pulling the arteriotomy 2691 closed, similar to a single-thread suture. For example, the expandable elements 2718 may be automatically collapsed immediately before or after the device 10 is deployed from the carrier assembly 2654 or when the carrier assembly 2654 reaches its extreme distal position. In the present embodiment, the distal portion 2716 of the obturator 2700 may be collapsed and retracted into the sheath 2654 after the primary and/or secondary tissue engaging portions 314, 316 have pierced and/or engaged the wall 2698 of the vessel 2690, but before the device 10 is entirely released from the sheath 2652.

In addition, if the device 10 includes secondary tissue engaging portions 316 (such as those shown in FIG. 29B), the secondary tissue engaging portions 316 may penetrate (partially in the present example) and/or engage the wall 2698 of the vessel 2690 during deployment of the device 10. In the present example, the lengths of the secondary tissue engaging portions 316 may be relatively short or stop members (not shown) may be provided that may prevent the primary and/or secondary tissue engaging portions 314, 316 from piercing entirely through the wall 2698. When the device 10 is released, the primary and/or secondary tissue engaging portions 314, 316 may pull the tissue inwardly, behaving somewhat similarly to a purse-string suture, to enhance closing the arteriotomy 2691.

Once the device 10 is successfully deployed into the wall 2698 of the vessel 2690, e.g., on either side of an arteriotomy 2691, the apparatus 2600 may be withdrawn from the passage 2692. The entire apparatus 2600 may be removed in one step, or alternatively, the obturator 2700 may first be withdrawn from the sheath 2652 before withdrawing the sheath 2652, thereby leaving the device 10 in place to close the arteriotomy 2691 and/or seal the passage 2692.

In the deployed configuration, the device 10 for managing access through tissue may substantially close and/or seal the incision, puncture, or other passage 2692 that extends from a patient's skin 2694, through intervening tissue 2696, and into a wall 2698 of a vessel 2690 or other body lumen; engage tissue in other procedures, e.g., to connect tissue segments together or otherwise to secure tissue structures with respect to one another (i.e. attach an anastomosis during a bypass procedure); and/or close an aperture (i.e. a puncture, cut, tear, and/or other aperture) on the surface of the patient's skin 2694. After the device 10 is deployed, it may be desirable to perform a second procedure. The location of the second procedure may be through the device 10. For example, it may be desirable to provide access through the tissue and through the device 10 for performing a second therapeutic or diagnostic procedure.

Figure 28E:
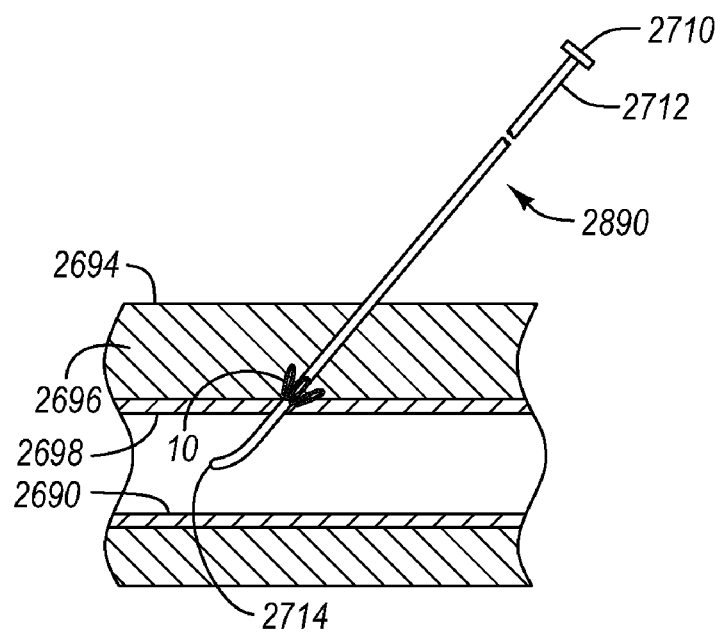

To perform the second procedure, as shown in FIG. 28E, a guide wire 2890, rail, stylet, and/or other device may be inserted into or otherwise positioned within the vessel 2690, i.e., through the device 10 for managing access through tissue and/or the passage 2692. Inserting a guide wire 2890 and/or other device may move the device 10 for managing access through the tissue from the deployed configuration into another configuration. In the present embodiment, the guide wire 2890 or other device may have a diameter that is larger than the first distance $d_1$ between two tissue engaging portions 13 in the deployed configuration but is smaller than the second distance $d_2$ between the two tissue engaging portions 13 in the pre-deployed configuration, such that the device 10 for managing access through tissue may be moved from the deployed configuration toward the pre-deployed configuration, though may not move to the pre-deployed configuration. In other embodiments, the guide wire 2890 or other device may have a diameter that is larger than the first distance $d_1$ but substantially the same size as the second distance $d_2$ such that the device 10 may be moved from the deployed configuration to the pre-deployed configuration. In further embodiments, the device 10 may move toward and/or to an access configuration, such as the access configuration shown in FIG. 6D. The movement of the device 10 for managing access through tissue may depend on the size of the device inserted through the device 10 for managing access through tissue, the characteristics of the device 10 (i.e. the stiffness in different directions), and/or other factors.

Figure 28F:
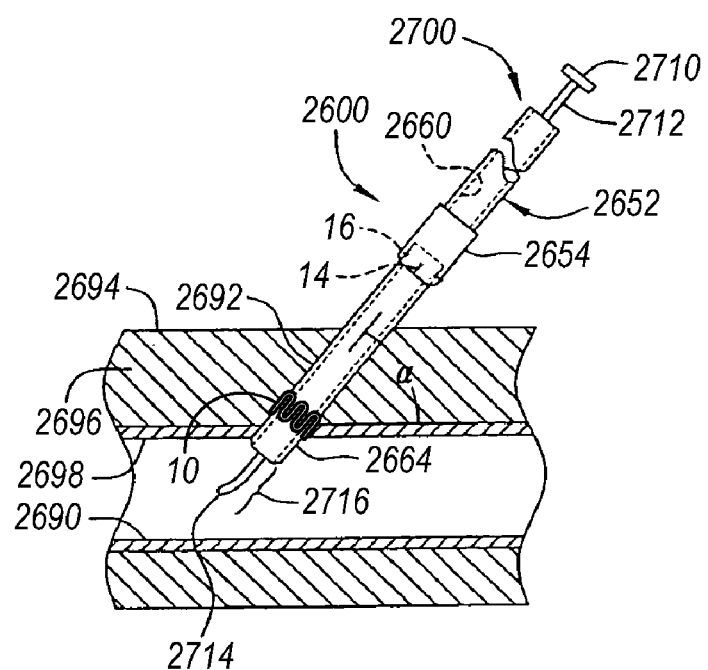

To perform the second procedure, as shown in FIG. 28F, the sheath 2652 may be reinserted into or otherwise positioned within the vessel 2690, i.e., through the device 10 for managing access through tissue and/or the passage 2692. The sheath 2652 may be advanced over the guide wire 2890, rail, stylet, and/or other device positioned through the device 10 for managing access through tissue and/or passage 2692 into the vessel 2690. As shown in FIG. 28F, the sheath may have a diameter that is larger than a first distance $d_1$ and substantially the same size as a second distance $d_2$, such that the device 10 may move from the deployed configuration towards and/or to the pre-deployed configuration.

The invention is susceptible to various modifications and alternative means, and specific examples thereof have been shown by way of example in the drawings and are herein described in detail. It should be understood, however, that the invention is not to be limited to the particular devices or methods disclosed, but to the contrary, the invention is to cover all modifications, equivalents, and alternatives falling within the spirit and scope of the claims.

What is claimed is:

1. A method for managing access through tissue, comprising:

deploying a closure element, having a plurality of tissue engaging portions, to tissue adjacent a tissue opening to bring the plurality of tissue engaging portions of the closure element toward one another to bring tissue together to substantially close the opening following a first procedure; and following closing of the tissue opening and following the first procedure and removal of any devices used during the first procedure and removal of a delivery device for deploying the closure element, advancing a distal end of a medical device through the deployed closure element as a part of or before a second procedure to selectively open the tissue opening and transition the deployed closure element from a deployed configuration towards a pre-deployed configuration and move the plurality of tissue engaging portions away from each other.

2. The method as in claim 1, wherein the tissue is skin.

3. The method as in claim 1, wherein the tissue is a wall of a body lumen.

4. The method as in claim 1, further comprising:

removing the distal end of the medical device through the opening in the tissue and through the closure element thereby redeploying the closure element to the tissue adjacent the opening in the tissue to substantially close the opening.

5. The method as in claim 1, wherein the closure element further comprises a radiopaque marker and wherein the method further comprises locating the deployed closure element using the radiopaque marker.

6. The method as in claim 1, wherein the method further comprises locating the deployed closure element using skin marking.

7. The method as in claim 1, wherein the medical device includes a cannula or other access device.

8. The method as in claim 1, wherein the closure element further comprises:

a body movable from a pre-deployed configuration towards a deployed configuration; and the plurality of tissue engaging portions extending from the body, at least a portion of the tissue engaging portions being obtuse, at least two of the tissue engaging portions being separated by a first distance in the deployed configuration and a second distance in the pre-deployed configuration, wherein the first distance is smaller than the second distance.

9. A method for managing access to a body lumen, comprising:

deploying a closure element to tissue adjacent a tissue opening to substantially close the opening following a first procedure with a plurality of non-penetrating tissue engaging portions, the closure element comprising:

a body movable from a pre-deployed configuration towards a deployed configuration; and the plurality of non-penetrating tissue engaging portions extending from the body, at least a portion of the non-penetrating tissue engaging portions being obtuse, at least two of the non-penetrating tissue engaging portions being separated by a first distance in the deployed configuration and a second distance in the pre-deployed configuration, wherein the first distance is smaller than the second distance; and wherein deploying the closure element brings the plurality of non-penetrating tissue engaging portions of the closure element towards one another to bring tissue together to substantially close the opening following the first procedure;

following closing of the tissue opening and following the first procedure and removal of any devices used during the first procedure and removal of a delivery device for deploying the closure element, locating the deployed closure element at the closed tissue opening;

following locating the deployed closure element, selectively opening the opening in the tissue by advancing a distal end of a medical device through the deployed closure element as a part of or before a second procedure to selectively open the tissue opening and transition the deployed closure element from a deployed configuration towards a pre-deployed configuration and move the plurality of tissue engaging portions away from each other; and removing the distal end of the medical device through the opening in the tissue and through the closure element thereby redeploying the closure element to the tissue adjacent the opening in the tissue to substantially close the opening.

10. The method as in claim 9, wherein the tissue is skin.

11. The method as in claim 9, wherein the tissue is a wall of a body lumen.

12. The method as in claim 9, wherein the closure element further comprises a radiopaque marker and wherein the method further comprises locating the deployed closure element using the radiopaque marker.

13. The method as in claim 9, wherein the locating the deployed closure element further comprises locating the deployed closure element using skin marking.

14. The method as in claim 9, wherein the medical device includes a cannula or other access device.

* * * * *